US008076329B2

(12) United States Patent
Bertrand et al.

(10) Patent No.: US 8,076,329 B2
(45) Date of Patent: Dec. 13, 2011

(54) HISTAMINE H3-RECEPTOR LIGANDS AND THEIR THERAPEUTIC APPLICATIONS

(75) Inventors: Isabelle Bertrand, Pace (FR); Marc Capet, Melesse (FR); Jeanne-Marie Lecomte, Paris (FR); Nicolas Levoin, Mordelles (FR); Xavier Ligneau, Saint Gregoire (FR); Olivia Poupardin-Olivier, Varois Et Chaignot (FR); Philippe Robert, Pace (FR); Jean-Charles Schwartz, Paris (FR); Olivier Labeeuw, Rennes (FR)

(73) Assignee: Bioprojet, Paris (FR)

( * ) Notice: Subject to any disclaimer, the term of this patent is extended or adjusted under 35 U.S.C. 154(b) by 70 days.

(21) Appl. No.: 11/912,816

(22) PCT Filed: Apr. 25, 2006

(86) PCT No.: PCT/IB2006/000991
§ 371 (c)(1),
(2), (4) Date: Oct. 26, 2007

(87) PCT Pub. No.: WO2006/117609
PCT Pub. Date: Nov. 9, 2006

(65) Prior Publication Data
US 2009/0111808 A1 Apr. 30, 2009

Related U.S. Application Data

(60) Provisional application No. 60/678,243, filed on May 6, 2005.

(30) Foreign Application Priority Data

Apr. 29, 2005 (EP) .................................... 05290950
Aug. 26, 2005 (EP) .................................... 05291793

(51) Int. Cl.
*A61K 31/4418* (2006.01)
*A61K 31/4453* (2006.01)
*A61K 31/4545* (2006.01)
*A61K 31/5355* (2006.01)
*C07D 213/30* (2006.01)
*C07D 211/14* (2006.01)
*C07D 413/12* (2006.01)

(52) U.S. Cl. .................... 514/235.5; 514/299; 514/318; 544/129; 546/194; 546/236

(58) Field of Classification Search ........................ None
See application file for complete search history.

(56) References Cited

U.S. PATENT DOCUMENTS

| 4,707,487 A | 11/1987 | Arrang et al. |
| 5,290,790 A | 3/1994 | Arrang et al. |
| 5,356,916 A | 10/1994 | Toyofuku et al. |
| 5,463,074 A | 10/1995 | Shih et al. |
| 5,486,526 A | 1/1996 | Durant et al. |
| 5,559,113 A | 9/1996 | Schwartz et al. |
| 5,578,616 A | 11/1996 | Aslanian et al. |
| 5,639,775 A | 6/1997 | Durant et al. |
| 5,663,350 A | 9/1997 | Durant et al. |
| 5,990,317 A | 11/1999 | Phillips et al. |
| 6,080,871 A | 6/2000 | Kalindjian et al. |
| 6,166,060 A | 12/2000 | Phillips et al. |
| 6,248,765 B1 | 6/2001 | Schwartz et al. |
| 2005/0113435 A1 | 5/2005 | Hancock et al. |
| 2005/0182045 A1 | 8/2005 | Nagase et al. |
| 2006/0235049 A1 | 10/2006 | Apodaca et al. |

FOREIGN PATENT DOCUMENTS

| DE | 21 42 563 | 5/1973 |
| EP | 680 960 | 11/1995 |
| JP | 2004262890 | 9/2004 |
| WO | WO-92/15567 | 9/1992 |
| WO | WO-93/12107 | 6/1993 |
| WO | WO-95/06037 | 3/1995 |
| WO | WO-95/11894 | 5/1995 |
| WO | WO-96/40126 | 12/1996 |
| WO | WO-00/06254 | 2/2000 |
| WO | WO-01/19821 | 3/2001 |
| WO | WO-01/74773 | 10/2001 |
| WO | WO-01/74814 | 10/2001 |
| WO | WO-01/74815 | 10/2001 |
| WO | WO 02/12214 | * 2/2002 |
| WO | WO-03/097047 | 11/2003 |
| WO | WO 2004/089373 | * 10/2004 |
| WO | WO-2005/070900 | 8/2005 |
| WO | WO-2005/077953 | 8/2005 |
| WO | WO-2005/089747 | 9/2005 |
| WO | WO 2006/004937 | * 1/2006 |

(Continued)

OTHER PUBLICATIONS

Brittain et al. "Polymorphism in Pharmaceutical Dosage Forms." Polymorphism in Pharmaceutical Solids XX (Jan. 1999). pp. 235-238, 348-361.*
Morissette et al. "High-throughput crystallization: polymorphs, salts, co-crystals and solvates of pharmaceutical solids." Advanced Drug Delivery Reviews 2004, 56, 275-300.*
Vippagunta, Sudha R. "Crystalline Solids." Advanced Drug Delivery Reviews 48(2001): 3-26.*
Shah et al. Bioorg. Med. Chem. Lett. 12 (2002), pp. 3309-3312.*
Faghih et al, "Aminoalkoxybiphenylnitriles as histamine-3 receptor ligands" Nov. 4, 2002, pp. 3077-3079, vol. 12, No. 21, Bioorganic & Medicinal Chemistry Letters, Oxford, Great Britain.
Apelt et al, "Seach for histamine H3 receptor antagonists with combined inhibitory potency at N-Methyltransferase: Ether Derivatives" 2005, pp. 97-106, vol. 60, No. 2, Pharmazie, Die, GOVI Verlag, Eschborn, DE.
Peschke et al, "Cinnamic amides of (S)-2-(aminomethyl)pyrrolidines are potent H3 antagonists", 2004, pp. 2603-2616, vol. 12, Bioorganic & Medicinal Chemistry.

(Continued)

*Primary Examiner* — Rebecca Anderson
*Assistant Examiner* — Alicia L Otton
(74) *Attorney, Agent, or Firm* — B. Aaron Schulman, Esq.; Terry L. Wright, Esq.; Stites & Harbison PLLC

(57) ABSTRACT

The present patent application concerns compounds of formula (I) with R1 and R2 taken together with the nitrogen atom to which they are attached, form a mono or bicyclic saturated nitrogen-containing ring; their preparation and their use as a H3 receptor ligand for treating e.g. CNS disorders like Alzheimer's disease.

12 Claims, No Drawings

FOREIGN PATENT DOCUMENTS

WO    WO-2006/004937      1/2006

OTHER PUBLICATIONS

Hiltmann et al, "Synthese von trans-3,5-Dimethyl-piperidin", 1971, pp. 213-214, Synthesis.

Arrang et al, "Actions of Betahistine at Histamine Receptors in the Brain", 1985, pp. 73-84, vol. 111, European Journal of Pharmacology.

Arrang et al, "Phencyclidine blocks histamine $H_3$-receptors in rat brain", 1988, pp. 31-35, vo. 157, European Journal of Pharmacology.

Clitherow et al, "Novel 1, 2, 4-Oxadiazoles as Potent and Selective Histamine $H_3$ Receptor Antagonists", 1996, pp. 833-838, vol. 6, No. 7, Bioorganic & Medicinal Chemistry Letters.

Ganellin et al,. "Structure-activity studies with histamine $H_3$-receptor ligands", 1995, pp. 455-468, vol. 36. No. 3, Ars. Pharmaceutica.

Kathmann et al, "Intermediate affinity and potency of clozapine and low affinity of other neuroleptics and of antidepressants at $H_3$ receptors", 1994, pp. 464-468, vol. 116, Psychopharmacology.

Plazzi et al, "Heteroarylaminoethyl and heteroarylthioethyl imidazoles. Synthesis and $H_3$-receptor affinity", 1995, pp. 881-889, vol. 30, Eur. J. Med. Chem.

Schwartz et al, "A third histamine receptor subtype: Characterisation, localization and functions of the $H_3$-receptor", 1990, pp. 13-23, vol. 30, Agents and Actions.

Schwartz et al, "Histaminergic Transmission in the Mammalian Brain", Jan. 1991, pp. 1-51, vol. 71, No. 1, Physiological Reviews.

Stark et al, "Developments of histamine $H_3$-receptor antagonists", 1996, pp. 507-520, vol. 21, No. 5, Drugs of the Future.

Wolin et al, "Novel $H_3$ Receptor Antagonists Sulfonamide Homologs of Histamine", 1998, pp. 2157-2162, Bioorganic & Medicinal Chemistry Letters 8.

* cited by examiner

HISTAMINE H3-RECEPTOR LIGANDS AND THEIR THERAPEUTIC APPLICATIONS

This application is a national stage entry of PCT/IB2006/000991, filed Apr. 25, 2006, which claims the benefit of U.S. Provisional Application Ser. No. 60/678,243 filed May 6, 2005, incorporated herein by reference.

The present patent application concerns new ligands of the $H_3$-receptor, their process of preparation and their therapeutic use.

Antagonists of histamine $H_3$-receptor are known especially to increase synthesis and release of cerebral histamine. Through this mechanism, they induce an extended wakefulness, an improvement in cognitive processes, a reduction in food intake and a normalization of vestibular reflexes (Schwartz et al., *Physiol. Rev.*, 1991, 71: 1-51).

Histamine $H_3$-receptor agonists are known to inhibit the release of several neurotransmitters including histamine, monoamines and neuropeptides and thereby exert sedative and sleep-promoting effects in brain. In peripheral tissues, $H_3$-receptor agonists exert namely anti-inflammatory, antinociceptive, gastro-intestinal, antisecretory smooth muscle decontracting activities.

$H_3$ receptor antagonist or agonist compounds previously known resemble histamine in possessing an imidazole ring generally monosubstituted in 4(5)-position (Ganellin et al., *Ars Pharmaceutica*, 1995, 36:3, 455-468; Stark et al., *Drug of the Future*, 1996, 21(5), 507-520).

Numerous patents and patent applications are directed to antagonist and/or agonist compounds having such structure, in particular EP 197 840, EP 494 010, WO 93/14070, WO 96/29315, WO 92/15567, WO 93/20061, WO 93/20062, WO 95/11894, U.S. Pat. No. 5,486,526, WO 93/12107, WO 93/12108, WO 95/14007, WO 95/06037, WO 97/29092, EP 680 960, WO 96/38141, WO 96/38142, WO 96/40126.

In the literature, Plazzi et al., *Eur. J. Med. Chem.*, 1995, 30, 881, Clitherow et al., *Bioorg. & Med. Chem. Lett.*, 6 (7), 833-838 (1996) Wolin et al., *Bioorg. & Med. Chem. Lett*, 8, 2157 (1998) can be cited also in this respect.

Nevertheless, such imidazole derivatives may show drawbacks such as poor blood-brain barrier penetration, interaction with cytochrome P-450 proteins and/or some hepatic and ocular toxicities.

Non-imidazole known neuro-active compounds such as betahistine (J-M. Arrang et al., *Eur. J. Pharmacol.*, 1985, 111: 72-84), phencyclidine (J-M. Arrang et al., *Eur. J. Pharmacol.*, 1988, 157: 31-35), dimaprit (J-C Schwartz et al., *Agents Actions*, 1990, 30: 13-23), clozapine (M. Kathmann et al., *Psychopharmacology* 1994, 116: 464-468), and sesquiterpenes (M. Takigawa et al., JP 06 345 642 (20 Dec. 1994)) were suggested to display $H_3$-receptor antagonism but all these compounds have only very low potency.

These compounds were previously known as therapeutic agent before the discovery and characterization of the histamine $H_3$-receptor, in particular as neuro-active agents for example as neuroleptic (clozapine) or psychotomimetic (Phencyclidine) agent.

When tested at the $H_3$-receptor, these compounds were shown to display much lower potency than the imidazole-containing compounds described in patent applications quoted above.

Contrary to previous attempts, the inventors succeeded at developing potent $H_3$-receptor ligands not containing imidazole ring that reduced the above-mentioned drawbacks. These compounds, their preparation and therapeutical applications thereof have been described in the international patent application WO 00/06254.

More specifically, WO 00/06254 discloses, inter allia, compounds of formula (IIa):

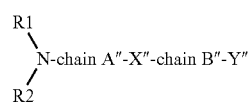

More precisely, formula (IIa) depicts a general pharmacophore that is furthermore widely exemplified in the above-mentioned patent.

For pharmaceutical use, it is desirable to have compounds that are metabolically stable. A general way for metabolising aromatics is the para oxidation. So it is wise to focus on compounds having a substituent in this position.

However, the inventors have found that compounds of WO 00/06254 exhibiting a para-substituted phenyl group generally inhibit cytochromes 2D6 or 3A4. This is particularly deleterious for pharmaceuticals as these cytochromes are both involved in metabolisation of xenobiotics and biotransformation of endogenous products.

Surprisingly, the inventors have now discovered that some specific modifications on these structures both afford compounds displaying a very good affinity for the human H3 receptor (Ki<10 nM) together with a dramatically reduced inhibition of cytochromes 2D6 and 3A4. This is expressed by an IC50 largely over the micromolar range.

The present invention is directed to these novel compounds which fulfill these requirements.

Additionally, preferred compounds of the invention exhibit a low HERG activity. Those showing a good bioavailability are particularly preferred.

According to a first object, the present invention concerns new compounds of formula (I):

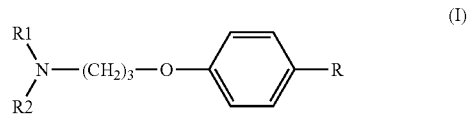

with R1 and R2 taken together with the nitrogen atom to which they are attached, form a mono or bicyclic saturated nitrogen-containing ring; preferably, said ring is of formula:

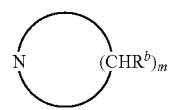

with m=4 or 5, each Rb is independently identical or different, and Rb represents a hydrogen or a $C_1$-$C_4$ alkyl, or 2 Rb form together a bond so as to form a bicyclic ring, such as, for example

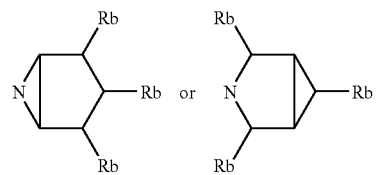

R is chosen from the groups selected within:

a) a ring chosen from heteroaryl, saturated or partially saturated heterocycloalkyl, or cycloalkyl, each optionally substituted with one or more of Halogen atom, C1-C4 alkyl, O—C1-C4 alkyl, OH, NR3R4 and/or where the heterocycloalkyl or heteroaryl comprise a N-atom within the ring, the N atom may be in the form of N-Oxyde ($N^+$—$O^-$), or chosen from mono or bicyclic aryl such as phenyl or naphthyl optionally substituted with one or more of Halogen atom, C1-C4 alkyl, O—C1-C4 alkyl, OH, NR3R4, —C2-C4 alkenyl or —C2-C4 alkynyl, where alkyl, alkenyl or alkynyl is optionally substituted with a heterocycle, a functional basic group, such as NR3R4 b) C1-C4 alkyl, C2-C4 alkenyl or C2-C4 alkynyl each being substituted with one or more of CN, aryl, cycloalkyl or —(C=O)$_m$—NR3R4, —O-(Alkyl)$_n$-Heterocycle wherein m=0 or 1, n=0 or 1, where aryl is optionally substituted with one or more of halogen, $C_1$-$C_4$ alkyl, O—$C_1$-$C_4$ alkyl, —OH, —(O)$_n$—X—NR3R4, where n=0 or 1, X represents an alkylene, alkenylene, alkynylene, where cycloalkyl is a 4 to 7-membered saturated cycloalkyl group optionally substituted with one or more of halogen, $C_1$-$C_4$ alkyl, O—$C_1$-$C_4$ alkyl, —OH or -(Alkyl)$_p$NR3R4 with p=0 or 1, and where Heterocycle is a saturated N-containing 5- to 10-membered ring, optionally substituted with C1-C4 alkyl;

c) CONR7R8, where R7, R8 represent independently a straight or branched $C_1$-$C_4$ alkyl;

d) —C(OH)R5R6 with R5 and R6 representing independently a straight or branched $C_1$-$C_4$ alkyl or $C_2$-$C_4$ alkenyl or alkynyl, an aryl group or taken together with the carbon atom to which they are attached form a saturated or partially unsaturated monocyclic or bicyclic carbocycle;

e) a phenoxy group in which the phenyl is optionally substituted by one or more of halogen, $C_1$-$C_4$ alkyl, O—$C_1$-$C_4$ alkyl, —OH, NR3R4;

f) a benzyloxy group in which the phenyl is optionally substituted by one or more of halogen, $C_1$-$C_4$ alkyl, O—$C_1$-$C_4$ alkyl, —OH, NR3R4;

g) isopropenyl;

h) a benzoyl group substituted by one or more of halogen, $C_1$-$C_4$ alkyl, O—$C_1$-$C_4$ alkyl, —OH or NR3R4;

wherein R3, R4 represent independently hydrogen, a straight or branched $C_1$-$C_4$ alkyl or an aryl group or taken together with the nitrogen atom to which they are attached form a saturated or partially unsaturated monocyclic or bicyclic heterocycle or heteroaryl optionally comprising one or more further heteroatoms and/or optionally substituted with one or more of Halogen atom, C1-C4 alkyl, O—C1-C4 alkyl, OH;

or their pharmaceutically acceptable salts, hydrates, or hydrated salts, or the polymorphic crystalline structures of these compounds or their optical isomers, racemates, diastereomers or enantiomers.

In a), where R is phenyl or naphthyl, then at least one of Rb is a $C_1$-$C_4$ alkyl.

Preferably, in general formula (I):

R1 and R2 form together with the nitrogen atom to which they are attached a mono saturated nitrogen-containing ring of formula:

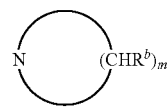

with m=4 or 5, each Rb is independently identical or different represents a hydrogen or a $C_1$-$C_4$ alkyl;

R is chosen from:

a) a ring chosen from monocyclic heteroaryl, saturated or partially saturated heterocycloalkyl, or cycloalkyl, each optionally substituted with one or more of Halogen atom, C1-C4 alkyl, O—C1-C4 alkyl, OH, NR3R4 and/or where the heterocycloalkyl or heteroaryl comprise a N-atom within the ring, the N atom may be in the form of N-Oxyde ($N^+$—$O^-$), or chosen from mono or bicyclic aryl such as phenyl or naphthyl substituted with one or more of Halogen atom, C1-C4 alkyl, O—C1-C4 alkyl, OH, NR3R4, —C2-C4 alkenyl or —C2-C4 alkynyl, where alkyl, alkenyl or alkynyl is optionally substituted with a heterocycle, a functional basic group, such as NR3R4 b) C1-C4 alkyl, C2-C4 alkenyl or C2-C4 alkynyl each being substituted with one or more of CN, aryl, cycloalkyl or —(C=O)$_m$—NR3R4, —O-(Alkyl)$_n$-Heterocycle, wherein m=0 or 1, n=0 or 1, where aryl is optionally substituted with one or more of halogen, $C_1$-$C_4$ alkyl, O—$C_1$-$C_4$ alkyl, —OH, —(O)$_n$—X—NR3R4 where wherein n=0 or 1, X represents an alkylene, alkenylene, alkynylene, where cycloalkyl is a 4 to 7-membered saturated cycloalkyl group optionally substituted with one or more of halogen, $C_1$-$C_4$ alkyl, O—$C_1$-$C_4$ alkyl, —OH or -(Alkyl)$_p$NR3R4 with p=0 or 1, and where Heterocycle is a saturated N-containing 5- to 10-membered ring, such as piperidine, optionally substituted with $C_1$-$C_4$ alkyl;

c) CONR7R8, where R7, R8 represent independently a straight or branched $C_1$-$C_4$ alkyl;

d) —C(OH)R5R6 with R5 and R6 representing independently a straight or branched $C_1$-$C_4$ alkyl or $C_2$-$C_4$ alkenyl or alkynyl, an aryl group or taken together with the carbon atom to which they are attached form a saturated or partially unsaturated monocyclic or bicyclic carbocycle;

e) a phenoxy group in which the phenyl is substituted by one or more of halogen, $C_1$-$C_4$ alkyl, O—$C_1$-$C_4$ alkyl, —OH, NR3R4;

f) a benzyloxy group in which the phenyl is optionally substituted by one or more of halogen, $C_1$-$C_4$ alkyl, O—$C_1$-$C_4$ alkyl, —OH, NR3R4;

g) isopropenyl;

wherein R3, R4 represent independently hydrogen, a straight or branched $C_1$-$C_4$ alkyl or an aryl group or taken together with the nitrogen atom to which they are attached form a saturated or partially unsaturated monocyclic or bicyclic heterocycle or heteroaryl optionally substituted with one or more of Halogen atom, C1-C4 alkyl, O—C1-C4 alkyl, OH;

or their pharmaceutically acceptable salts, hydrates, or hydrated salts, or the polymorphic crystalline structures of these compounds or their optical isomers, racemates, diastereomers or enantiomers.

More preferably, in general formula (I)

R1 and R2 form together with the nitrogen atom to which they are attached a mono saturated nitrogen-containing ring of formula:

with m=4 or 5, each Rb is independently identical or different represents a hydrogen or a $C_1$-$C_4$ alkyl;

R is chosen from the groups selected within:
  a) a ring chosen from monocyclic heteroaryl, saturated or partially saturated heterocycloalkyl, or cycloalkyl, each optionally substituted with one or more of halogen atom, C1-C4 alkyl, O—C1-C4 alkyl, OH, NR3R4 and/or where the heterocycloalkyl or heteroaryl comprise a N-atom within the ring, the N atom may be in the form of N-Oxyde ($N^+$—$O^-$), or
  chosen from monocyclic aryl such as phenyl substituted with one or more of C1-C4 alkyl, O—C1-C4 alkyl, NR3R4, —C2-C4 alkenyl,
  where alkyl, alkenyl or alkynyl is optionally substituted with a heterocycle or a functional basic group, such as NR3R4
  b) C1-C4 alkyl, C2-C4 alkenyl or C2-C4 alkynyl each being substituted with one or more of CN, aryl, cycloalkyl or —NR3R4
  where cycloalkyl is a 4 to 7-membered saturated cycloalkyl group optionally substituted with one or more of NR3R4,
  c) CONR7R8, where R7, R8 represent independently a straight or branched $C_1$-$C_4$ alkyl;
  d) —C(OH)R5R6 with R5 and R6 representing independently a straight or branched $C_1$-$C_4$ alkyl or $C_2$-$C_4$ alkenyl, or taken together with the carbon atom to which they are attached form a saturated or partially unsaturated monocyclic carbocycle;
  e) a benzyloxy group in which the phenyl is optionally substituted by one or more of halogen, $C_1$-$C_4$ alkyl, O—$C_1$-$C_4$ alkyl, —OH, NR3R4;
  f) isopropenyl;
  wherein R3, R4 represent independently hydrogen, a straight or branched $C_1$-$C_4$ alkyl or an aryl group or taken together with the nitrogen atom to which they are attached form a saturated or partially unsaturated monocyclic or bicyclic heterocycle or heteroaryl optionally substituted with one or more of Halogen atom, C1-C4 alkyl, O—C1-C4 alkyl, OH;
  or their pharmaceutically acceptable salts, hydrates, or hydrated salts, or the polymorphic crystalline structures of these compounds or their optical isomers, racemates, diastereomers or enantiomers.

More preferably, m=5; preferably, where m=4, each Rb=H.

Compounds where R is one of a) are preferred, in particular those compounds where R is a) chosen from aryl or heteroaryl rings.

Particularly preferred compounds are such that in a), R is chosen from a ring chosen from:
  heteroaryl, in particular those heteroaryl rings comprising a N-atom, optionally substituted with one or more of halogen atom or C1-C4 alkyl; preferably, those heteroaryl rings comprising a N atom where the N atom is in the form of N-Oxyde ($N^+$—$O^-$), or
  aryl such as phenyl substituted with one or more of C1-C4 alkyl, O—C1-C4 alkyl, NR3R4, —C2-C4 alkenyl where alkyl, alkenyl or alkynyl is optionally substituted with a heterocycle or NR3R4.

Preferred compounds of formula (I) can be chosen from:
trans-1-{3-[4-(N,N-dimethylcarbamoyl)phenoxy]propyl}-3,5-dimethylpiperidine,
trans-1-{3-[4-(N,N-tetramethylenecarbamoyl)phenoxy]propyl}-3,5-dimethylpiperidine,
1-[3-(4-benzoylphenyl)propoxy]piperidine,
1-[3-(4-cyanomethylphenyl)propoxy]piperidine,
trans-1-{3-[4-(1-hydroxy-1-methylethyl)phenoxy]propyl}-3,5-dimethylpiperidine,
(RS)-1-{3-[4-(1-hydroxy-1-methylethyl)phenoxy]propyl}-3-methylpiperidine,
1-{3-[4-(1-hydroxy-1-propylbutyl)phenoxy]propyl}piperidine,
1-{3-[4-(1-hydroxycyclopentyl)phenoxy]propyl}piperidine
1-{3-[4-(1-hydroxy-1-allylbut-3-enyl)phenoxy]propyl}piperidine,
trans-1-{3-(4-isopropenylphenoxy)propyl]-3,5-dimethylpiperidine,
trans-1-{3-(4-styrylphenoxy)propyl]piperidine
(3S,5S)-1-{3-[4-(trans-4-dimethylaminocyclohex-1-yl)phenoxy]propyl}-3,5-dimethylpiperidine
1-{3-[4-(benzyloxy)phenoxy]propyl}piperidine
trans-3,5-dimethyl-1-[3-(4-phenoxyphenoxy)propyl]piperidine,
6-[4-(3-piperidinopropoxy)phenyl]-2,3,4,5-tetrahydropyridine,
trans-6-{4-[3-(3,5-dimethylpiperidino)propoxy]phenyl}-2,3,4,5-tetrahydropyridine,
trans-1-{3-[4-(4,5-dihydro-3H-pyrrol-2-yl)phenoxy]propyl}-3,5-dimethylpiperidine,
1-{3-[4-(cis-4-dimethylaminocyclohex-1-yl)phenoxy]propyl}piperidine,
1-{3-[4-(trans-4-dimethylaminocyclohex-1-yl)phenoxy]propyl}piperidine,
1-{3-[4-(cis-4-tetramethylenaminocyclohex-1-yl)phenoxy]propyl}piperidine,
1-{3-[4-(trans-4-tetramethylenaminocyclohex-1-yl)phenoxy]-propyl}piperidine,
trans-1-{3-[4-(cis-4-dimethylaminocyclohex-1-yl)phenoxy]propyl}-3,5-dimethylpiperidine,
trans-1-{3-[4-(trans-4-dimethylaminocyclohex-1-yl)phenoxy]propyl}-3,5-dimethylpiperidine,
1-{3-[(biphenyl-4-yl)oxy]propyl}pyrrolidine,
trans-1-{3-[(biphenyl-4-yl)oxy]propyl}-3,5-dimethylpiperidine,
(3S,5S)-1-{3-[(biphenyl-4-yl)oxy]propyl}-3,5-dimethylpiperidine,
1-{3-[(4'-methylbiphenyl-4-yl)oxy]propyl}piperidine,
1-{3-[(4'-methoxybiphenyl-4-yl)oxy]propyl}piperidine,
(RS)-1-{3-[(biphenyl-4-yl)oxy]propyl}-3-methylpiperidine,
trans-3,5-dimethyl-1-{3-[(4'-methylbiphenyl-4-yl)oxy]propyl}piperidine,
1-{3-[(2'-methylbiphenyl-4-yl)oxy]propyl}piperidine,
1-{3-[4-(3-thienyl)phenoxy]propyl}piperidine,
1-{[3-{4-(4-pyridyl)phenoxy]propyl}piperidine,
trans-3,5-dimethyl-1-{3-[4-(4-pyridyl)phenoxy]propyl}piperidine,
1-{3-[4-(3-pyridyl)phenoxy]propyl}piperidine,
trans-3,5-dimethyl-1-{3-[4-(pyrrol-1-yl)phenoxy]propyl}piperidine,
trans-3,5-dimethyl-1-{3-[4-(pyrazol-3-yl)phenoxy]propyl}piperidine,
di-1,1'-{(biphenyl-4,4'-diyl)bis[oxy(propan-1,3-diyl)]}piperidine, 4-(3-{[4'-(3-piperidinopropoxy)biphenyl-4-yl]oxy}propyl) morpholine,
1-(3-{[4'-(3-piperidinopropoxy)biphenyl-4-yl]oxy}propyl) pyrrolidine,
di-1,1'-{(biphenyl-4,4'-diyl)bis[oxy(propan-1,3-diyl)]}pyrrolidine
di-1,1'-{methylenebis[(phenyl-1,4-diyl)oxy(propan-1,3-diyl)]}piperidine,
(3S,5S)-1-{3-[4-(trans-4-dimethylaminocyclohex-1-yl)phenoxy]propyl}-3,5-dimethylpiperidine
(3S)-1-{3-[4-(trans-4-dimethylaminocyclohex-1-yl)phenoxy]propyl}-3-methylpiperidine,
(3S)-3-methyl-1-{3-[4-(4-pyridyl)phenoxy] propyl}piperidine,
1-(3-{[4'-(piperidinomethyl)biphenyl-4-yl]oxy}propyl)piperidine
(3S,5S)-1-{3-[4-(trans-4-morpholinocyclohex-1-yl)phenoxy]propyl}-3,5-dimethylpiperidine
(3S)-1-{3-[4-(trans-4-morpholinocyclohex-1-yl)phenoxy]propyl}-3-methylpiperidine
1-{3-[4-(trans-4-morpholinocyclohex-1-yl)phenoxy]propyl}piperidine
1-{3-[4-(cis-4-morpholinocyclohex-1-yl)phenoxy]propyl}piperidine, dihydrochloride
1-{3-[4-(trans-4-morpholinocyclohex-1-yl)phenoxy]propyl}piperidine, dihydrochloride
(3S)-3-methyl-1-{3-[4-(cis-4-morpholinocyclohex-1-yl)phenoxy]propyl}piperidine, dihydrochloride
(3S)-3-methyl-1-{3-[4-(trans-4-morpholinocyclohex-1-yl)phenoxy]propyl}piperidine, dihydrochloride
1-(3-{[4'-(piperidinomethyl)biphenyl-4-yl]oxy}propyl)piperidine
1-{3-[4-(4-piperidinobut-1-yn-1-yl)phenoxy]propyl}piperidine
(E)-1-(3-{[4'-(3-piperidinoprop-1-en-1-yl)biphenyl-4-yl]oxy}propyl)piperidine
(Z)-1-(3-{[4'-(3-piperidinoprop-1-en-1-yl)biphenyl-4-yl]oxy}propyl)piperidine
1-methyl-4-[4'-(3-piperidinopropoxy)biphenyl]piperazine
1-{3-[4-(cis-4-dimethylaminocyclohex-1-yl)methylphenoxy]propyl}piperidine,
1-{3-[4-(trans-4-dimethylaminocyclohex-1-yl)methylphenoxy]propyl}piperidine,
4-(3-{[4'-(3-piperidinopropyl)biphenyl-4-yl]oxy}propyl)piperidine,
(3S,5S)-1-{3-[4-(trans-4-aminocyclohex-1-yl)phenoxy]propyl}-3,5-dimethylpiperidine,
(3S)-4-{4-[3-(3-methylpiperidin-1-yl)propoxy] phenyl}pyridine 1-oxide,
(3S)-4-{4-[3-(3-methylpiperidin-1-yl)propoxy] phenyl}pyridine 1-oxide,
4-[4-(3-piperidinopropoxy)phenyl]pyridine 1-oxide,
2-methyl-4-(4-{3-[(3S)-3-methylpiperidin-1-yl] propoxy}phenyl)pyridine 1-oxide,
2-hydroxy-4-(4-{3-[(3S)-3-methylpiperidin-1-yl] propoxy}phenyl)pyridine,
1-methyl-4-(4-{3-[(3S)-3-methylpiperidin-1-yl] propoxy}phenyl)pyridinium
2-(3-piperidinopropoxy)-4-(4-{3-[(3S)-3-methylpiperidin-1-yl]propoxy}phenyl)pyridine
2-methyl-4-(4-{3-[(3S)-3-methylpiperidin-1-yl] propoxy}phenyl)pyridine
1-{3-[4-(4-hydroxycyclohexyl)phenoxy]propyl}piperidine
(3S)-1-{3-[trans-4-(4-hydroxycyclohexyl)phenoxy]propyl}-3-methylpiperidine
(3S)-1-{3-[4-(4-hydroxycyclohexyl)phenoxy]propyl}-3-methylpiperidine
1-{3-[trans-4-(4-hydroxycyclohexyl)phenoxy] propyl}pyrrolidine
(3S)-1-{3-[4-(4-hydroxy-4-methylcyclohexyl)phenoxy]propyl}-3-methylpiperidine
1-{3-[trans-4-(4-hydroxycyclohexyl)phenoxy] propyl}piperidine
1-{3-[trans-4-(4-hydroxycyclohexyl)phenoxy]propyl}-2-methylpyrrolidine
1-methyl-4-[4-(3-piperidinopropoxy)benzyloxy]piperidine,
1-methyl-4-[4-(3-piperidinopropoxy)benzyloxymethyl]piperidine,
1-methyl-4-{2-[4-(3-piperidinopropoxy)benzyloxy] ethyl}piperidine,
1-ethyl-3-[4-(3-piperidinopropoxy)benzyloxy]piperidine, or their pharmaceutically acceptable salts, hydrates, or hydrated salts, or the polymorphic crystalline structures of these compounds or their optical isomers, racemates, diastereomers or enantiomers.

More particularly:
trans-1-{3-[4-(N,N-dimethylcarbamoyl)phenoxy]propyl}-3,5-dimethylpiperidine,
trans-1-{3-[4-(1-hydroxy-1-methylethyl)phenoxy]propyl}-3,5-dimethylpiperidine,
1-{3-[4-(1-hydroxy-1-propylbutyl)phenoxy] propyl}piperidine,
(3S,5S)-1-{3-[4-(trans-4-dimethylaminocyclohex-1-yl)phenoxy]propyl}-3,5-dimethylpiperidine,
6-[4-(3-piperidinopropoxy)phenyl]-2,3,4,5-tetrahydropyridine,
trans-6-{4-[3-(3,5-dimethylpiperidino)propoxy]phenyl}-2,3,4,5-tetrahydropyridine,
trans-1-{3-[4-(4,5-dihydro-3H-pyrrol-2-yl)phenoxy]propyl}-3,5-dimethylpiperidine,
1-{3-[4-(cis-4-dimethylaminocyclohex-1-yl)phenoxy]propyl}piperidine,
1-{3-[4-(trans-4-dimethylaminocyclohex-1-yl)phenoxy]propyl}-piperidine,
1-{3-[4-(cis-4-tetramethylenaminocyclohex-1-yl)phenoxy]propyl}piperidine,
1-{3-[4-(trans-4-tetramethylenaminocyclohex-1-yl)phenoxy]propyl}-piperidine,
trans-1-{3-[4-(cis-4-dimethylaminocyclohex-1-yl)phenoxy]propyl}-3,5-dimethylpiperidine,
trans-1-{3-[4-(trans-4-dimethylaminocyclohex-1-yl)phenoxy]propyl}-3,5-dimethylpiperidine,
1-{3-[(2'-methylbiphenyl-4-yl)oxy]propyl}piperidine,
1-{[3-{4-(4-pyridyl)phenoxy]propyl}piperidine,
trans-3,5-dimethyl-1-{3-[4-(4-pyridyl)phenoxy] propyl}piperidine,
1-{3-[4-(3-pyridyl)phenoxy]propyl}piperidine,
trans-3,5-dimethyl-1-{3-[4-(pyrazol-3-yl)phenoxy] propyl}piperidine,
di-1,1'-{(biphenyl-4,4'-diyl)bis[oxy(propan-1,3-diyl)]}piperidine,
4-(3-{[4'-(3-piperidinopropoxy)biphenyl-4-yl]oxy}propyl) morpholine,
1-(3-{[4'-(3-piperidinopropoxy)biphenyl-4-yl]oxy}propyl) pyrrolidine
di-1,1'-{(biphenyl-4,4'-diyl)bis[oxy(propan-1,3-diyl)]}pyrrolidine
(3S)-3-methyl-1-{3-[4-(4-pyridyl)phenoxy] propyl}piperidine,
1-{3-[4-(cis-4-morpholinocyclohex-1-yl)phenoxy] propyl}piperidine,
1-{3-[4-(trans-4-morpholinocyclohex-1-yl)phenoxy] propyl}piperidine, (3S)-3-methyl-1-{3-[4-(cis-4-morpholinocyclohex-1-yl)
phenoxy]propyl}piperidine,
(3S)-3-methyl-1-{3-[4-(trans-4-morpholinocyclohex-1-yl)
phenoxy]propyl}piperidine,
1-(3-{[4'-(piperidinomethyl)biphenyl-4-yl]oxy}propyl)piperidine
1-{3-[4-(4-piperidinobut-1-yn-1-yl)phenoxy]
propyl}piperidine
(3S)-4-{4-[3-(3-methylpiperidin-1-yl)propoxy]
phenyl}pyridine 1-oxide,
(3S)-4-{4-[3-(3-methylpiperidin-1-yl)propoxy]
phenyl}pyridine 1-oxide,
(3S)-4-{4-[3-(3-methylpiperidin-1-yl)propoxy]
phenyl}pyridine 1-oxide,
(3S)-1-{3-[trans-4-(4-hydroxycyclohexyl)phenoxy]propyl}-3-methylpiperidine,
(3S)-1-{3-[4-(4-hydroxycyclohexyl)phenoxy]propyl}-3-methylpiperidine,
or their pharmaceutically acceptable salts, hydrates, or hydrated salts, or the polymorphic crystalline structures of these compounds or their optical isomers, racemates, diastereomers or enantiomers.

Still more particularly:
trans-1-{3-[4-(1-hydroxy-1-methylethyl)phenoxy]propyl}-3,5-dimethylpiperidine,
1-{3-[4-(1-hydroxy-1-propylbutyl)phenoxy]
propyl}piperidine,
6-[4-(3-piperidinopropoxy)phenyl]-2,3,4,5-tetrahydropyridine,
trans-6-{4-[3-(3,5-dimethylpiperidino)propoxy]phenyl}-2,3,4,5-tetrahydropyridine,
1-{3-[4-(cis-4-dimethylaminocyclohex-1-yl)phenoxy]
propyl}piperidine,
1-{3-[4-(trans-4-dimethylaminocyclohex-1-yl)phenoxy]
propyl}-piperidine,
1-{3-[4-(cis-4-tetramethylenaminocyclohex-1-yl)phenoxy]
propyl}piperidine,
1-{3-[4-(trans-4-tetramethylenaminocyclohex-1-yl)phenoxy]propyl}-piperidine,
trans-1-{3-[4-(cis-4-dimethylaminocyclohex-1-yl)phenoxy]
propyl}-3,5-dimethylpiperidine,
trans-1-{3-[4-(trans-4-dimethylaminocyclohex-1-yl)phenoxy]propyl}-3,5-dimethylpiperidine,
1-{[3-{4-(4-pyridyl)phenoxy]propyl}piperidine,
trans-3,5-dimethyl-1-{3-[4-(4-pyridyl)phenoxy]
propyl}piperidine,
1-{3-[4-(3-pyridyl)phenoxy]propyl}piperidine,
trans-3,5-dimethyl-1-{3-[4-(pyrazol-3-yl)phenoxy]
propyl}piperidine,
di-1,1'-{(biphenyl-4,4'-diyl)bis[oxy(propan-1,3-diyl)]}piperidine,
4-(3-{[4'-(3-piperidinopropoxy)biphenyl-4-yl]oxy}propyl)
morpholine,
1-(3-{[4'-(3-piperidinopropoxy)biphenyl-4-yl]oxy}propyl)
pyrrolidine
di-1,1'-{(biphenyl-4,4'-diyl)bis[oxy(propan-1,3-diyl)]}pyrrolidine
(3S)-3-methyl-1-{3-[4-(4-pyridyl)phenoxy]
propyl}piperidine,
1-{3-[4-(cis-4-morpholinocyclohex-1-yl)phenoxy]
propyl}piperidine,
1-{3-[4-(trans-4-morpholinocyclohex-1-yl)phenoxy]
propyl}piperidine,
(3S)-3-methyl-1-{3-[4-(cis-4-morpholinocyclohex-1-yl)
phenoxy]propyl}piperidine,
(3S)-3-methyl-1-{3-[4-(trans-4-morpholinocyclohex-1-yl)
phenoxy]propyl}piperidine,
1-(3-{[4'-(piperidinomethyl)biphenyl-4-yl]oxy}propyl)piperidine
1-{3-[4-(4-piperidinobut-1-yn-1-yl)phenoxy]
propyl}piperidine
(3S)-4-{4-[3-(3-methylpiperidin-1-yl)propoxy]
phenyl}pyridine 1-oxide,
(3S)-4-{4-[3-(3-methylpiperidin-1-yl)propoxy]
phenyl}pyridine 1-oxide,
(3S)-4-{4-[3-(3-methylpiperidin-1-yl)propoxy]
phenyl}pyridine 1-oxide,
(3S)-1-{3-[trans-4-(4-hydroxycyclohexyl)phenoxy]propyl}-3-methylpiperidine,
(3S)-1-{3-[4-(4-hydroxycyclohexyl)phenoxy]propyl}-3-methylpiperidine,
or their pharmaceutically acceptable salts, hydrates, or hydrated salts, or the polymorphic crystalline structures of these compounds or their optical isomers, racemates, diastereomers or enantiomers.

Particularly, preferred compounds are:
(3S)-3-methyl-1-{3-[4-(4-pyridyl)phenoxy]
propyl}piperidine, dioxalate
(3S)-4-{4-[3-(3-methylpiperidin-1-yl)propoxy]
phenyl}pyridine 1-oxide, oxalate
(3S)-4-{4-[3-(3-methylpiperidin-1-yl)propoxy]
phenyl}pyridine 1-oxide, hydrochloride
(3S)-4-{4-[3-(3-methylpiperidin-1-yl)propoxy]
phenyl}pyridine 1-oxide, dihydrochloride As used hereabove or hereafter:

"Alkyl" means an aliphatic hydrocarbon group which may be straight or branched having 1 to 20 carbon atoms in the chain. Preferred alkyl groups have 1 to 12 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl.

"Alken" means an aliphatic hydrocarbon group containing a carbon-carbon double bond and which may be straight or branched having 2 to 15 carbon atoms in the chain. Preferred alkenyl groups have 2 to 12 carbon atoms in the chain; and more preferably about 2 to 4 carbon atoms in the chain. Exemplary alkenyl groups include ethenyl, propenyl, n-butenyl, i-butenyl, 3-methylbut-2-enyl, n-pentenyl, heptenyl, octenyl, nonenyl, decenyl.

"Alkyn" means an aliphatic hydrocarbon group containing a carbon-carbon triple bond and which may be straight or branched having 2 to 15 carbon atoms in the chain. Preferred alkynyl groups have 2 to 12 carbon atoms in the chain; and more preferably 2 to 4 carbon atoms in the chain. Exemplary alkynyl groups include ethynyl, propynyl, n-butynyl, 2-butynyl, 3-methylbutynyl, n-pentynyl, heptynyl, octynyl and decynyl.

"Halogen atom" refers to fluorine, chlorine, bromine or iodine atom; preferably fluorine and chlorine atom.

"Cycloalkyl" means a non-aromatic mono- or multicyclic hydrocarbon ring system of 3 to 10 carbon atoms, preferably of 5 to 10 carbon atoms. Preferred ring sizes of rings of the ring system include 5 to 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl.

"Aryl" means an aromatic monocyclic or multicyclic hydrocarbon ring system of 6 to 14 carbon atoms, preferably of 6 to 10 carbon atoms. Exemplary aryl groups include phenyl or naphthyl.

As used herein, the terms "heterocycle" or "heterocyclic" refer to a saturated, partially unsaturated or unsaturated, non aromatic stable 3 to 14, preferably 5 to 10 membered mono, bi or multicyclic rings wherein at least one member of the ring is a hetero atom. Typically, heteroatoms include, but are not limited to, oxygen, nitrogen, sulfur, selenium, and phosphorus atoms. Preferable heteroatoms are oxygen, nitrogen and sulfur.

Suitable heterocycles are also disclosed in *The Handbook of Chemistry and Physics*, 76$^{th}$ Edition, CRC Press, Inc., 1995-1996, pages 2-25 to 2-26, the disclosure of which is hereby incorporated by reference.

Preferred non aromatic heterocyclic include, but are not limited to pyrrolidinyl, pyrazolidinyl, imidazolidinyl, oxiranyl, tetrahydrofuranyl, dioxolanyl, tetrahydropyranyl, dioxanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyridyl, dihydropyridyl, tetrahydropyrimidinyl, dihydrothiopyranyl, azepanyl, as well as the fused systems resulting from the condensation with a phenyl group.

As used herein, the term "heteroaryl" or aromatic heterocycles refers to a 5 to 14, preferably 5 to 10 membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, isoquinolyl, benzo-thienyl, isobenzofuryl, pyrazolyl, carbazolyl, benzimidazolyl, isoxazolyl, pyridyl-N-oxide, as well as the fused systems resulting from the condensation with a phenyl group.

As used herein, the terms "carbocycle" or "carbocyclic" refer to a saturated, partially unsaturated or unsaturated, non aromatic stable 3 to 14, preferably 5 to 10 membered mono, bi or multicyclic rings. Suitable carbocycles are also disclosed in *The Handbook of Chemistry and Physics*, 76$^{th}$ Edition, CRC Press, Inc., 1995-1996, pages 2-25 to 2-26, the disclosure of which is hereby incorporated by reference.

Preferred carbocycles include, but are not limited to cycloalkyls, cycloalkenyls or cycloalkynyls.

"Alkyl", "cycloalkyl", "alkenyl", "alkynyl", "aryl", "heteroaryl", "heterocycle" and the likes refers also to the corresponding "alkylene", "cycloalkylene", "alkenylene", "alkynylene", "arylene", "heteroarylene", "heterocyclene" and the likes which are formed by the removal of two hydrogen atoms.

As used herein, the term "patient" refers to a warm-blooded animal such as a mammal, preferably a human or a human child, which is afflicted with, or has the potential to be afflicted with one or more diseases and conditions described herein.

As used herein, a "therapeutically effective amount" refers to an amount of a compound of the present invention which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, the term "pharmaceutically acceptable" refers to those compounds, materials, compositions, or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucuronic, gluconic, glutamic, benzoic, salicylic, toluenesulfonic, oxalic, fumaric, maleic, and the like. Further addition salts include ammonium salts such as tromethamine, meglumine, epolamine, etc., metal salts such as sodium, potassium, calcium, zinc or magnesium. Hydrochloride and oxalate salts are preferred.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 or P. H. Stahl, C. G. Wermuth, *Handbook of Pharmaceutical Salts, Properties, Selection and Use*, Wiley-VCH, 2002, the disclosure of which are hereby incorporated by reference.

The compounds of the general formula (I) having geometrical and stereomers are also a part of the invention.

According to a further object, the present invention is also concerned with the process of preparation of the compounds of formula (I).

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, VCH publishers, 1989.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as N,N-dimethylformamide; alcohols such as ethanol and methanol and ethers, such as diethyl ether, methyl tert-butyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

The process of preparation of a compound of formula (I) of the invention is another object of the present invention.

According to the present invention, the expression "precursor group" of a functional group refers to any group which can, by one or more reactions, lead to the desired function, by means of one or more suitable reagents. Those reactions include the de-protection reactions, as well as usual addition, substitution or functionalization reactions.

According to a first aspect, compounds of the invention of formula (I) can be prepared from compounds of formula (II)

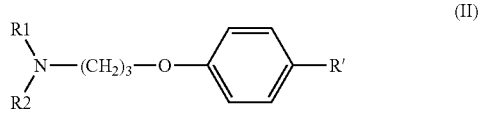

(II)

in which R1 and R2 are as defined in general formula (I), and R' represents a precursor group of R. Generally, a substitution or functionalization reaction of R' into the desired R function is carried out.

More precisely, when R represents a group with an alcohol function, the compound of formula (I) can be obtained from a compound of formula (II) in which R' represents a group with a carbonyl function, with a suitable organomagnesium halide or, conversely, from a compound of formula (II) where R' presents a halogen atom, by forming the corresponding organomagnesium halide followed by a Grignard reaction, by means of the suitable reagent exhibiting a carbonyl function.

More precisely, when R represents a group with a CONR3R4 function, the compound of formula (I) can be obtained from the corresponding compound of formula (II) in which R' represents a group with an acid halide function, by means of a suitable reagent having the HNR3R4 function. Said compound of formula (II) in which R' represents a group with an acid halide function can, in turn, be obtained from a compound of formula (II) in which R' represents an acid group which, in turn, can be obtained from a compound of formula (II) in which R' presents an ester group.

More precisely, when R represents a group with an alkenyl function, the compound of formula (I) can be obtained from the corresponding compound of formula (II) in which R' represents a group with an alcohol function, by a dehydration reaction.

More precisely, when R represents a group with a NR3R4 function, the compound of formula (I) can be obtained from the corresponding compound of formula (II) in which R' represents a group with a carbonyl function, by an amination reaction, under reducing conditions.

Alternatively, when R represents a group with a NR3R4 function, compound of formula (I) can be obtained from the corresponding compounds of formula (II) in which R' represents a group with a halogen atom with a suitable HNR3R4 reagent.

More precisely, said functionalization reaction can also comprise a step consisting in a Suzuki reaction, from a compound of formula (II) in which R' represents a halogen atom, with a suitable reagent of formula 1: $(OH)_2$—B—R (1).

Preferably, this reaction is carried out in the presence of $Pd(PPh_3)_4$ under basic conditions.

According to a second aspect, compound of the invention of formula (I) can be obtained from the corresponding compound of formula (III)

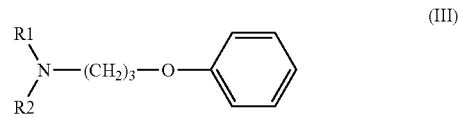

(III)

in which R1 and R2 are as defined in general formula (I). Generally, a reaction comprising the step of grafting or constructing the desired R group is carried out.

More precisely, when R represents a heterocycle, said heterocycle can be made up in one or more successive steps according to generally known reactions under suitable conditions.

According to a further aspect, compounds of formula (I) can be obtained by coupling compounds of formula (IV) and (V)

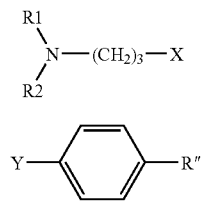
(IV)

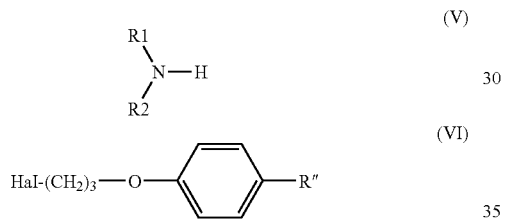
(V)

in which R1 and R2 are as defined in general formula (I), Y and X respectively represent a nucleophilic group and a leaving group or a precursor thereof, R" represents R as defined in formula (I) or R' as defined in formula (II). Generally, when X and Y represent a —OH function, said reaction is a Mitsunobu reaction. Generally, when X represents a halogen atom and Y represents a —OH function, said reaction is carried out under basic conditions.

According to a further aspect, compounds of formula (I) can be obtained by coupling compounds of formula (V) and (VI)

(V)

(VI)
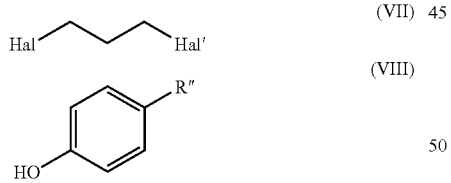

in which R1 and R2 are as defined in formula (I), Hal represents a halogen atom, R" represents R as defined in general formula (I) or R' as defined in general formula (II). Generally, said reaction is carried out under basic conditions.

Compound of formula (VI) can be obtained by coupling compounds of formula (VII) and (VIII):

(VII)

(VIII)

in which Hal and R" are as defined in formula (VI), Hal' represents a halogen atom.

Compound of formula (V) can be obtained by reduction and cyclization of compound of formula (IX)

(IX)

wherein Ra, Rb and m are as defined in formula (I). Generally, this reaction is carried out under catalytic conditions, in the presence of a catalyst such as rhodium on alumina.

Further, the process of the invention may also comprise the additional step of isolating the compound of formula (I). This can be done by the skilled person by any of the known conventional means, such as the recovery methods described above.

The starting products are commercially available or may be obtained by applying or adapting any known methods or those described in the examples.

In particular, the process of the invention may make use of optically pure starting products or intermediates. More particularly, use of the following derivative (X):

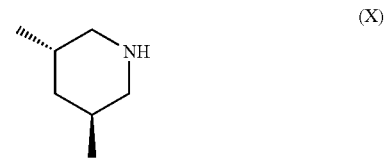
(X)

(X) is particularly useful for the process of the invention. The inventors have now discovered a new process for preparing optically pure (3S,5S)-dimethylpiperidine.

According to a further object, the present invention thus concerns a process for preparing compound of formula (X) comprising the step of reacting compound of formula (XI):

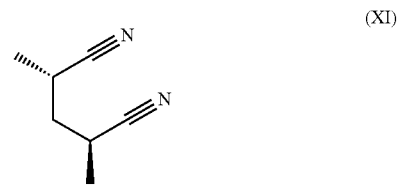
(XI)

More precisely, said step comprises reducing (XI), preferably under catalytic conditions, such as rhodium catalyst on alumina, in the presence of an alcohol such as methanol, with a reducing agent such as dihydrogen or an hydride such as a borohydride or an aluminium hydride, optionally in the presence of a metal such as a nickel salt.

(XI) is in turn is obtained from compound of formula (XII):

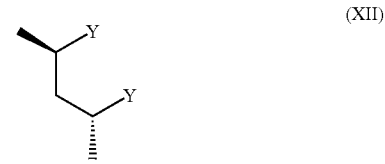
(XII)

with Y representing a leaving group such as a mesylate or an halogen atom. Generally, said reaction is carried out in the presence of a cyanide, such as potassium cyanide.

(XII) is obtained from compound of formula (XI):

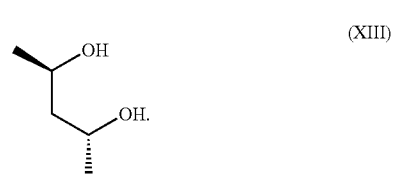
(XIII)

Generally, said reaction is carried out with a suitable reagent of formula: Hal-Y, such a methanesulfonylchloride, in the presence of a base or with an halogenating agent such as sulfonyl chloride with or without a base such as imidazole.
Representative schemes of the processes of the invention are summarized below:
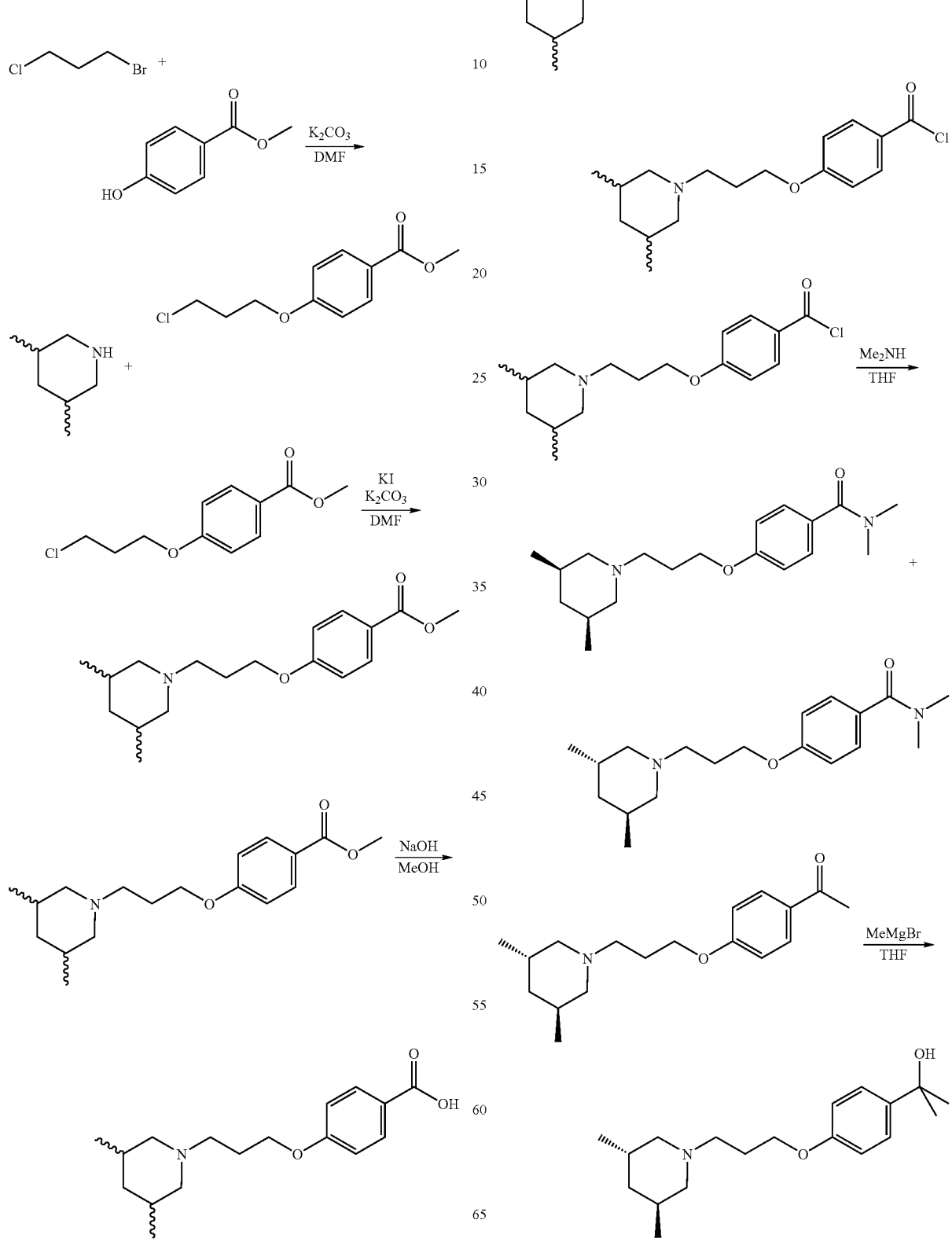

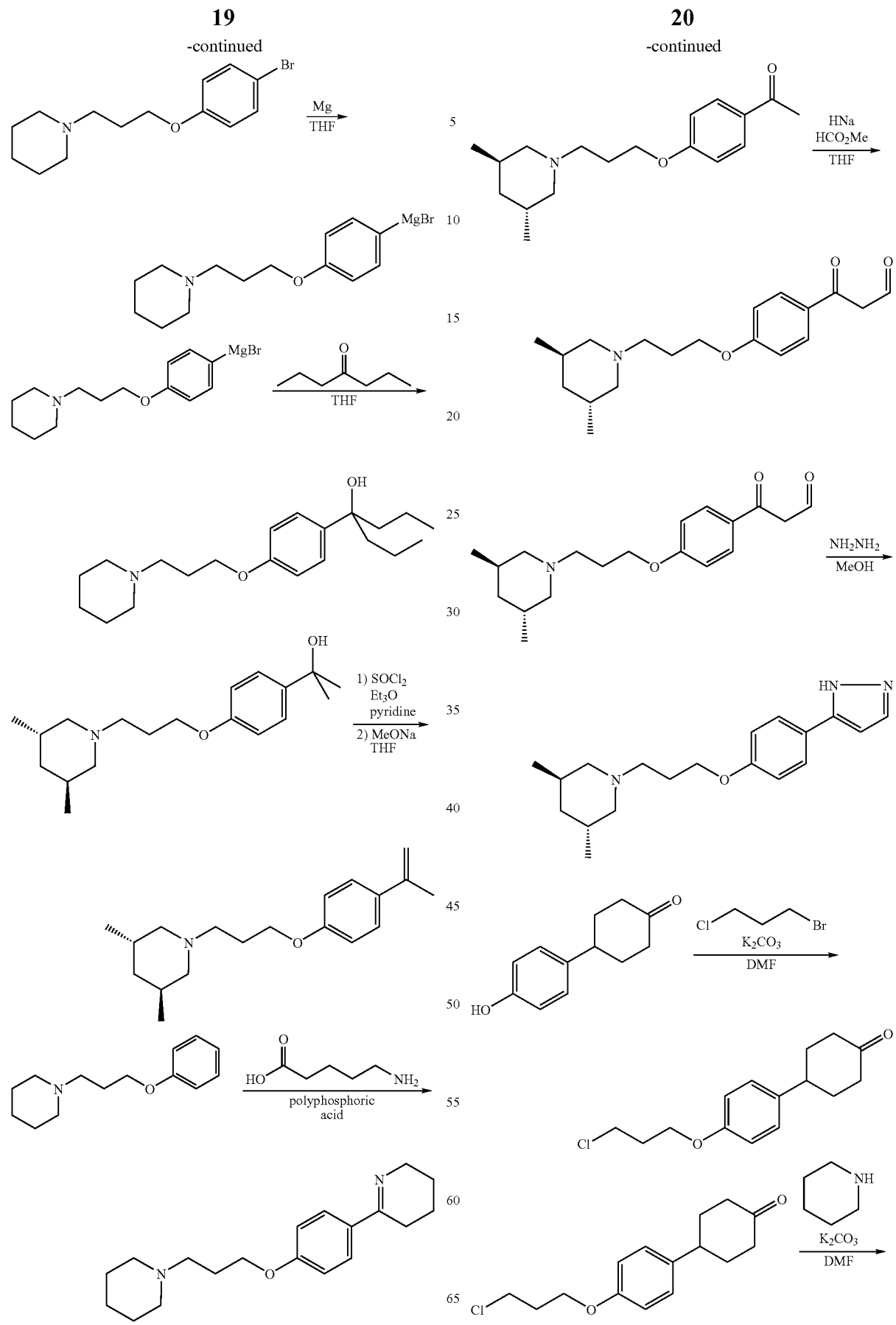

21
-continued
22
-continued
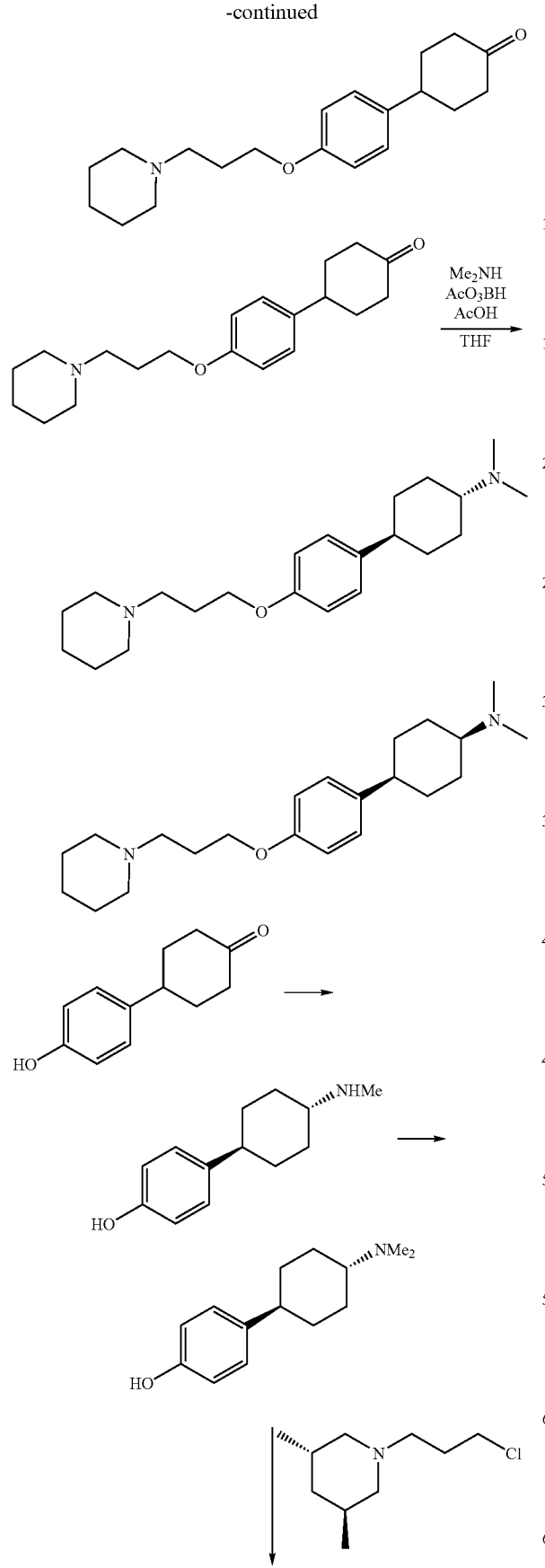
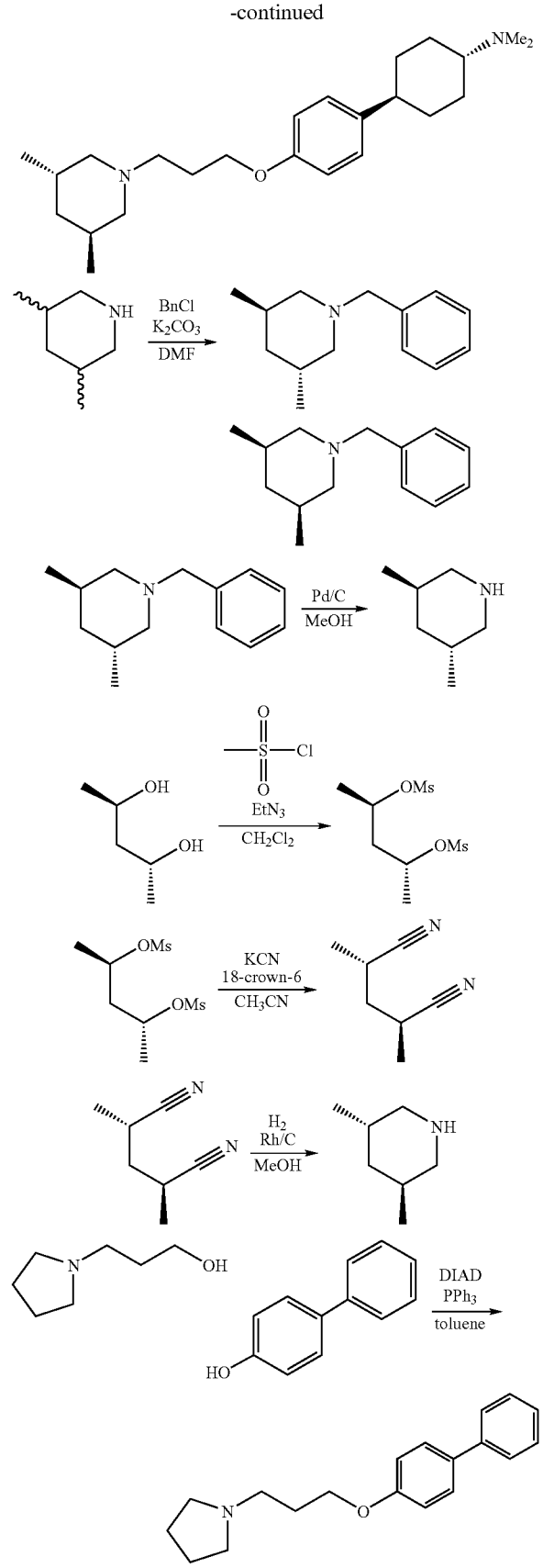

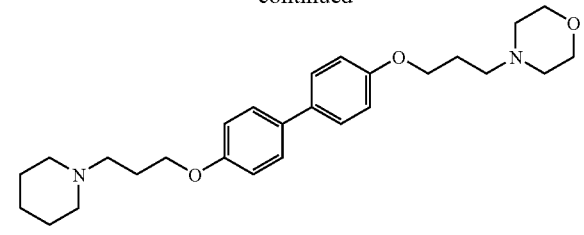
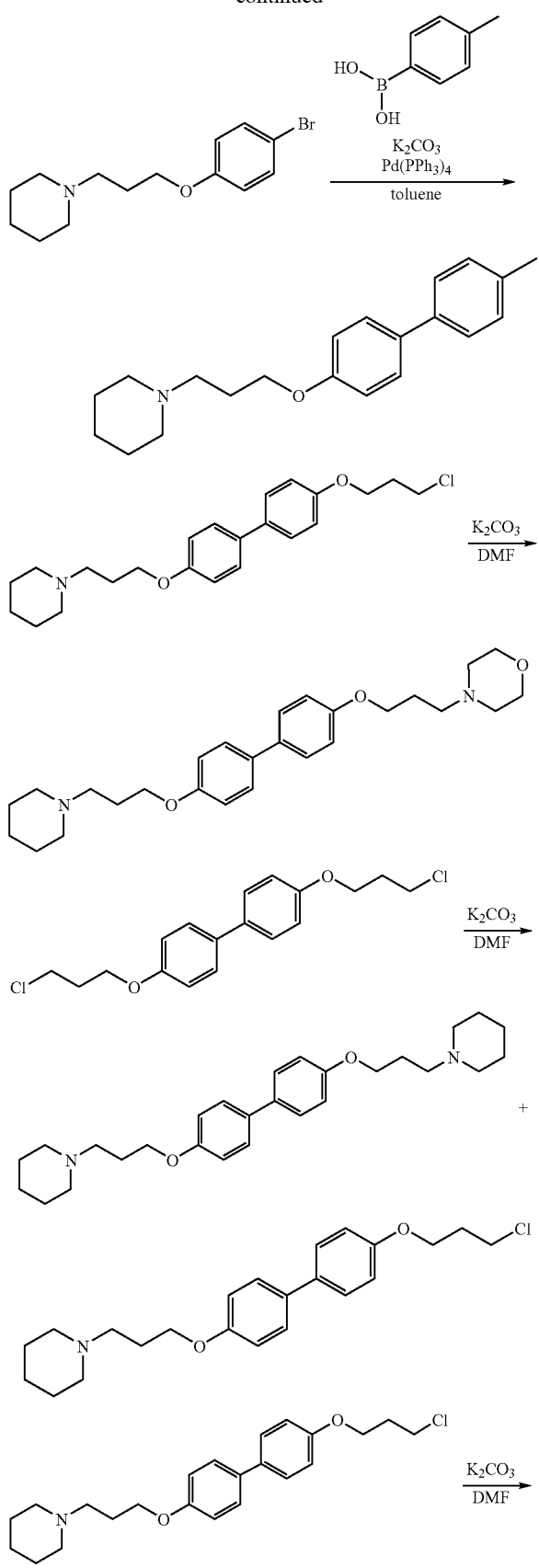

The synthesis may also be carried out in one pot as a multicomponent reaction.

According to a further object, the present invention is also concerned with pharmaceutical compositions comprising a compound of formula (I) together with a pharmaceutically acceptable excipient or carrier.

The antagonists are advantageously used as active ingredient in particular, of medicaments having psychotropic effects, promoting wakefulness, attention, memory and improving mood, in treatment of pathologies such as Alzheimer's disease and other cognitive disorders in aged persons, depressive or simply asthenic states. Preferably, said compounds may be used to treat and/or prevent CNS disorders, such as Alzheimer's disease, attention, wakefulness, memorization disorders, cognitive deficits in psychiatric pathologies, in particular in aged persons, depressive or asthenia states.

Their nootropic effects can be useful to stimulate vigilance, attention and memorization capacity in healthy humans. The compounds of the invention can also be useful to facilitate night work or adaptation to time shift in humans.

In addition, these agents can be useful in treatment of obesity, vertigo and motion sickness.

It can also be useful to associate the compounds of the invention with other psychiatric agents such as neuroleptics to increase their efficiency and reduce their side effects.

Application in certain form of epilepsy is also foreseen.

Their therapeutic applications involve also peripheral organs mainly a stimulant of secretions or gastro-intestinal motricity.

The compounds of the invention are particularly useful for the treatment of CNS disorders of aged persons.

Additionally, said antagonists or inverse agonists may also be useful in treating and/or preventing epilepsy.

As used herein, "epilepsy" denotes a brain disorder in which clusters of nerve cells, or neurons, in the brain sometimes signal abnormally. Epilepsy is also known as a seizure disorder. A seizure is a sudden surge of electrical activity in the brain. Epilepsy is usually diagnosed after a person has had at least two seizures that were not caused by some known medical condition like alcohol withdrawal or extremely low blood sugar.

Preferably, epilepsy is selected from the group consisting in absence epilepsy, in children and adults, pharmaco-resistant temporal lobe seizures, and photosensitive seizures.

Additionally, the present application also concerns the use of the compounds of the invention for treating and/or preventing Parkinson's disease, obstructive sleep apnea (OSA), Dementia with Lewy bodies and/or vascular dementia, and in particular the treatment of the symptoms thereof.

As used herein, "obstructive sleep apnea" (also referred to herein as "OSA") denotes a breathing disorder that occurs primarily during sleep with consequences that may persist throughout the waking hours in the form of sleepiness. This increasingly well-recognized disease is characterized by periodic collapse of the upper airway during sleep with apneas (periodic cessation of breathing), hypopneas (repetitive reduction in breathing) or a continuous or sustained reduction in ventilation and excessive daytime sleepiness, neurocognitive defects and depression. It affects almost every system in the body, resulting namely in increased incidence of cardiovascular disorders (Qureshi and Ballard, *J. Allergy and Clin. Immunol.*, 2003, 112, 643). There is no known pharmacological treatment for OSA.

"Parkinson's disease" ("PD") is mainly associated with a degeneration of dopaminergic neurons in the nigrostriatal tract from which derive the motor impairments and neuropsychiatric disorders characteristic of the disease. Whereas some other aminergic neuron classes might be affected in the parkinsonian brain, post-mortem neurochemical and immunohistochemical studies have shown that histaminergic neurons are completely spared from the degeneration process (Garbarg et al., *Lancet* 1983, 1, 74; Nakamura et al., *Neurology*, 1996, 4, 1693). In addition, in a model of "Parkinsonian" rat, in which the nigrostriatal dopaminergic neurons had been previously destroyed by unilateral administration of the neurotoxin 6-hydroxy-dopamine, the effect of the antiparkinsonian drug levodopa on the turning behaviour, a reflect of its antiparkinsonian activity, was not modified by co-administration of thioperamide, a prototypical $H_3R$ antagonist/inverse agonist (Huotary et al., *Parkinsonism Relat Disord.*, 2000, 6, 159). This absence of effect is not attributable to either an absence of H3R sites in the nigrostriatal complex where, on the contrary, they abound (Pillot et al., *Neuroscience*, 2002, 114, 176) or a disappearance of $H_3R$ sites as a result of the neuronal degeneration process, since the number of these sites is, on the contrary, elevated in the same animal model (Ryu et al., *Neurosci. Letters*, 1994, 178, 19). Taken together these findings suggested the lack of therapeutic interest of this class of drugs in the management of PD.

In addition to the major signs of PD in the movement initiation and control which constitute the core of the disease, it has become apparent during the last decades that a large proportion (as large as 74-81%) of PD patients display sleep and vigilance disorders (Garcia-Borreguero et al., *Sleep Med. Rev.*, 2003, 7, 115). These include disorders of sleep initiation and maintenance, sleep fragmentation, parasomnias (including nocturnal hallucinations), sleep disordered breathing and excessive daytime sleepiness (including "sleep attacks", i.e. inappropriate and unintended falls into sleep while in daytime activity). It is not entirely clear whether this group of disorders is purely related to the PD itself or whether there is also some participation of the treatment by direct or indirect dopaminergic agonists. The treatment of this class of disorders, which may all result from a loss of circadian rythmicity, is poorly efficient: for instance modafinil treatment of excessive daytime sleepiness was tried with limited success and the indication for this stimulant drug of essentially unknown mechanism of action has not been recognized by health authorities.

PD refers to idiopathic PD or idiopathic parkinsonism described by James Parkinson in 1817. The clinical tetrad of PD includes tremor at repose, bradykinesia (slowness of voluntary movement) or akinesia (reduced or absent movement), cogwheel or leadpipe rigidity, and postural impairment causing difficulty in turning and a stooped posture. The pathologic hallmark is the presence of intracytoplasmic eosinophilic inclusions (Lewy bodies) in addition to loss of neurons in the substantia nigra pars compacta. In addition to the major signs of PD in the movement initiation and control which constitute the core of the disease a large proportion of PD patients display sleep and vigilance disorders. These "sleep and vigilance disorders associated with PD" include in particular insomnia, disorders of sleep initiation and maintenance, sleep fragmentation, parasomnias, sleep disordered breathing, excessive daytime sleepiness (including "sleep attacks") and circadian dysrhythmia (inversion of sleep-wake rhythm).

Dementia with Lewy bodies (DLB) results from the accumulation of such bodies in the cortex (whereas their accumulation in the nigro-striatal complex is observed in PD, a related degenerative disease). It is characterized by cognitive impairment, attentional disturbances, hallucinations, depression and sleep disorders.

Vascular dementia (VD), the second most frequent cause of dementia, after Alzheimer's disease, is characterized by acute loss of memory, orientation and executive functions and is often associated with demonstrable cerebrovascular lesions in patients suffering from hypertension, diabetes, hyperlipidemia, sleep apnea for several years.

The compounds of the invention can also be useful for the treatment and/or prevention of vertigo, motion sickness, obesity, diabetes and so-called 'metabolic syndrome'. Metabolic syndrome was first defined as syndrome X by Reaven (Diabetes 1988, 37, 1595-607). It refers to a cluster of metabolic disorders such as diabetes, impaired glucose tolerance, insulin resistance, hyperinsulinemia, hypertriglyceridemia, dyslipidemia, low HDL-cholesterol, hypertension, micro-albuminuria, obesity, inflammation, cardiovascular disorders and/or abnormalities of fibrinolysis and of coagulation.

Additionally, the compounds of the invention can be useful for treating and/or preventing sleep disorders, stress, psychotropic disorders, convulsion, depression, narcolepsy, disorders of the hypothalamohypophyseal secretion, the cerebral circulation and/or immune system.

The present invention also concerns the corresponding methods of treatment comprising the administration of a compound of the invention together with a pharmaceutically acceptable carrier or excipient to a patient in the need thereof.

The identification of those subjects who are in need of treatment of herein-described diseases and conditions is well within the ability and knowledge of one skilled in the art. A clinician skilled in the art can readily identify, by the use of clinical tests, physical examination and medical/family history, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), which is required to achieve the desired biological effect, will vary depending upon a number of factors, including the dosage of the drug to be administered, the chemical characteristics (e.g. hydrophobicity) of the compounds employed, the potency of the compounds, the type of disease, the diseased state of the patient and the route of administration.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable carrier" includes any diluents, adjuvants, excipients, or vehicles, such as preserving agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/medicament according to the present invention effective in producing the desired therapeutic effect.

According to the invention, the term "patient", or "patient in need thereof", is intended for a human or non-human mammal affected or likely to be affected with a neuropsychological disorder. Preferably, the patient is a human.

In general terms, the compounds of this invention may be provided in an aqueous physiological buffer solution containing 0.1 to 10% w/v compound for parenteral administration. Typical dose ranges are from 1 μg/kg to 0.1 g/kg of body weight per day; a preferred dose range is from 0.01 mg/kg to 10 mg/kg of body weight per day. A preferred daily dose for adult humans includes 5, 50, 100 and 200 mg, and an equivalent dose in a human child. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

The compounds of the present invention are capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical daily dose ranges are from 0.01 to 10 mg/kg of body weight. By way of general guidance, unit doses for humans range from 0.1 mg to 1000 mg per day. Preferably the unit dose range is from 1 to 500 mg administered one to four times a day, and even more preferably from 10 mg to 300 mg, two times a day. Compounds provided herein can be formulated into pharmaceutical compositions by admixture with one or more pharmaceutically acceptable excipients. Such compositions may be prepared for use in oral administration, particularly in the form of tablets or capsules; or parenteral administration, particularly in the form of liquid solutions, suspensions or emulsions; or intranasally, particularly in the form of powders, nasal drops, or aerosols; or dermally, for example, topically or via trans-dermal patches.

The compositions may conveniently be administered in unit dosage form and may be prepared by any of the methods well known in the pharmaceutical art, for example, as described in *Remington: The Science and Practice of Pharmacy*, 20$^{th}$ ed.; Gennaro, A. R., Ed.; Lippincott Williams & Wilkins: Philadelphia, Pa., 2000. Pharmaceutically compatible binding agents and/or adjuvant materials can be included as part of the composition. Oral compositions will generally include an inert diluent carrier or an edible carrier.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Preferred formulations include pharmaceutical compositions in which a compound of the present invention is formulated for oral or parenteral administration, or more preferably those in which a compound of the present invention is formulated as a tablet. Preferred tablets contain lactose, cornstarch, magnesium silicate, croscarmellose sodium, povidone, magnesium stearate, or talc in any combination. It is also an aspect of the present disclosure that a compound of the present invention may be incorporated into a food product or a liquid.

Liquid preparations for administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

The invention is further illustrated but not restricted by the description in the following examples.

EXAMPLE 1

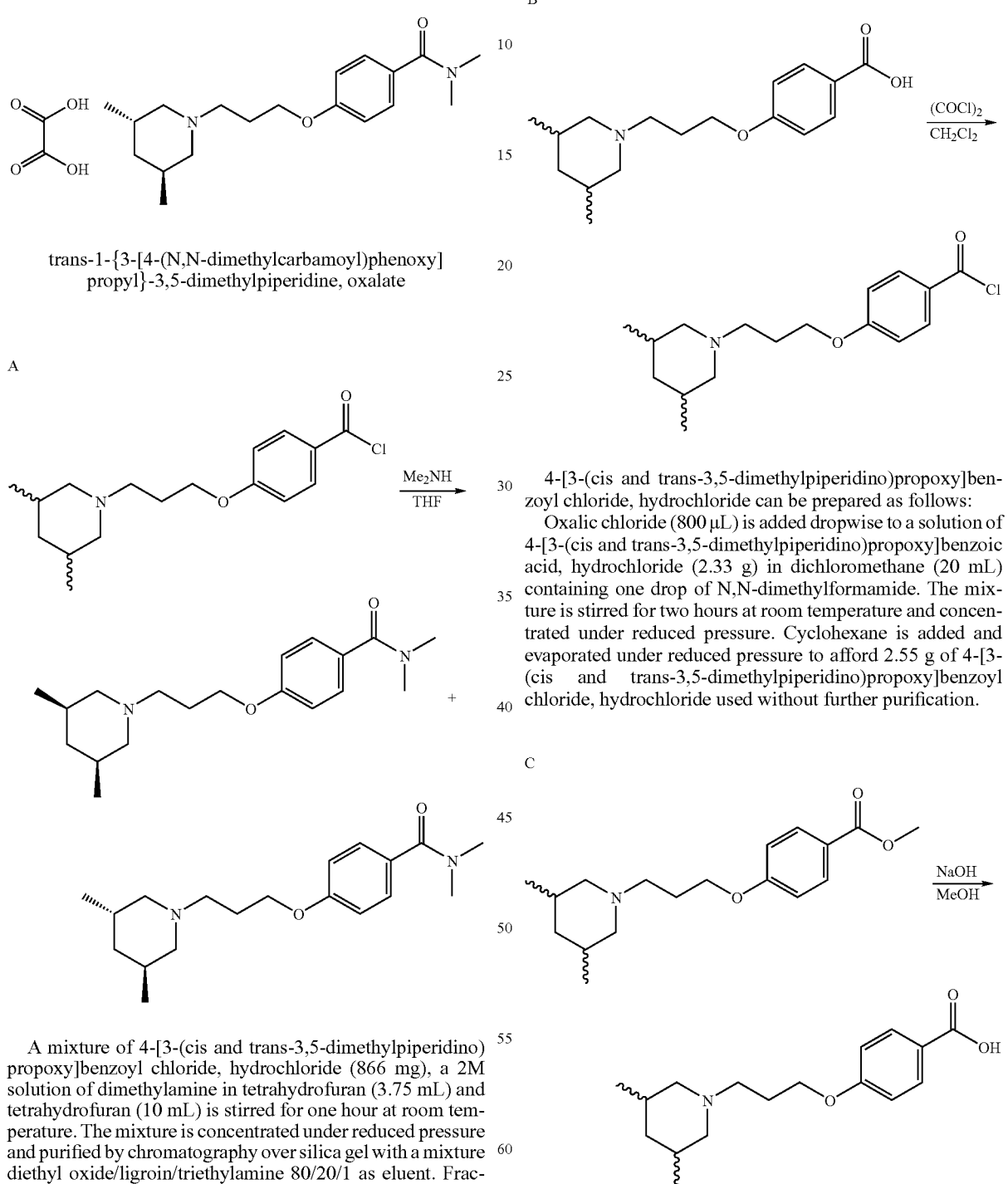

A trans-1-{3-[4-(N,N-dimethylcarbamoyl)phenoxy]propyl}-3,5-dimethylpiperidine, oxalate A mixture of 4-[3-(cis and trans-3,5-dimethylpiperidino)propoxy]benzoyl chloride, hydrochloride (866 mg), a 2M solution of dimethylamine in tetrahydrofuran (3.75 mL) and tetrahydrofuran (10 mL) is stirred for one hour at room temperature. The mixture is concentrated under reduced pressure and purified by chromatography over silica gel with a mixture diethyl oxide/ligroin/triethylamine 80/20/1 as eluent. Fraction containing the expected product are pooled, concentrated under reduced pressure and salted with 20 mg of oxalic acid to yield 37 mg of trans-1-{3-[4-(N,N-dimethylcarbamoyl)-phenoxy]propyl}-3,5-dimethylpiperidine, oxalate as a pink powder.

$^1$H NMR: base (CDCl$_3$)

7.38 (d, J=8.7 Hz, 2H, arom), 6.90 (d, J=8.7 Hz, 2H, arom), 4.05 (t, J=6.0 Hz, 2H, CH$_2$O), 3.05 (br s, 6H, 2 CH$_3$NCO), 2.5-1.8 (m, 10H, 3 CH$_2$N, CH$_2$, 2 CH), 1.25 (dd, J=5.8 Hz, J=5.8 Hz, 2H, CH$_2$), 0.95 (2d, J=6.8 Hz, J=6.8 Hz, 6H, 2 CH$_3$).

B

4-[3-(cis and trans-3,5-dimethylpiperidino)propoxy]benzoyl chloride, hydrochloride can be prepared as follows:

Oxalic chloride (800 μL) is added dropwise to a solution of 4-[3-(cis and trans-3,5-dimethylpiperidino)propoxy]benzoic acid, hydrochloride (2.33 g) in dichloromethane (20 mL) containing one drop of N,N-dimethylformamide. The mixture is stirred for two hours at room temperature and concentrated under reduced pressure. Cyclohexane is added and evaporated under reduced pressure to afford 2.55 g of 4-[3-(cis and trans-3,5-dimethylpiperidino)propoxy]benzoyl chloride, hydrochloride used without further purification.

C

4-[3-(cis and trans-3,5-dimethylpiperidino)propoxy]benzoic acid, hydrochloride can be prepared as follows:

A solution of cis and trans-1-{3-[4-(methoxycarbonyl)phenoxy]propyl}-3,5-dimethylpiperidine (5.3 g) in a 1N aqueous sodium hydroxide solution (50 mL) and methanol (30 mL) is heated under reflux for 30 min. Methanol is evaporated under reduced pressure. The aqueous layer is washed with ethyl acetate and acidified with aqueous hydrochloric acid. The precipitate that appeared is filtered and dried to give 4-[3-(cis and trans-3,5-dimethylpiperidino)propoxy]benzoic acid, hydrochloride as a white solid.

Rf TLC (dichloromethane/methanol 90/10)=0.15

D

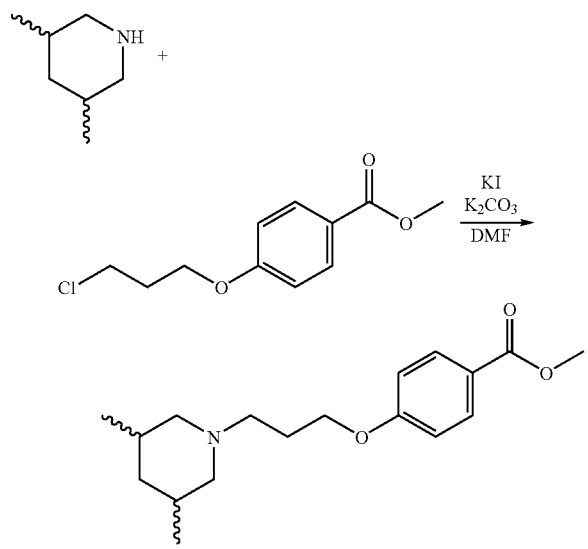

cis and trans-1-{3-[4-(methoxycarbonyl)phenoxy]propyl}-3,5-dimethylpiperidine can be prepared as follows:

A mixture of methyl 4-(3-chloropropoxy)benzoate (4.57 g), potassium carbonate (8.29 g), cis and trans-3,5-dimethylpiperidine (5.31 mL) and a catalytic amount of potassium iodide in N,N-dimethylformamide (100 mL) is stirred overnight at 100° C. The suspension is filtrated and the precipitate washed with ethanol. The filtrate is concentrated under reduced pressure and purified by chromatography over silica gel with a gradient of dichloromethane/methanol from 98/2 to 90/10. Fraction containing the expected products are pooled and concentrated under reduced pressure yielding 5.33 g of cis and trans-1-{3-[4-(methoxycarbonyl)phenoxy]propyl}-3,5-dimethylpiperidine.

Rf TLC (dichloromethane/methanol 90/10)=0.5
Rf TLC (dichloromethane/methanol 95/5)=0.3

E

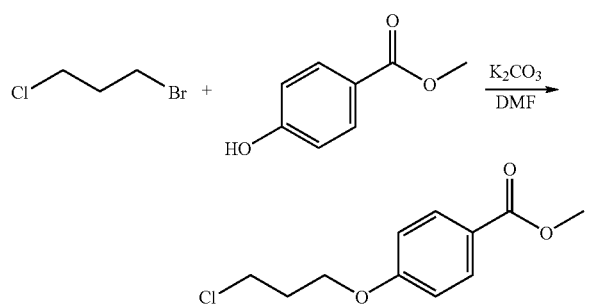

Methyl 4-(3-chloropropoxy)benzoate can be prepared as follows:

A suspension of potassium carbonate (48.4 g) in a mixture of methyl 4-hydroxybenzoate (10.65 g), 1-bromo-3-chloropropane (55.1 g) and N,N-dimethylformamide (100 mL) is stirred at room temperature for 15 h. Solids are separated by filtration and washed three times with ethanol (30 mL). The combined filtrates are concentrated under reduced pressure, and then dissolved in ethyl acetate (200 mL). The organic layer is washed twice with water (50 mL), dried over magnesium sulphate and concentrated under reduced pressure to give 15 g of methyl 4-(3-chloropropoxy)benzoate used without further purification.

Rf TLC (heptane/ethyl acetate 2/1)=0.5

EXAMPLE 2

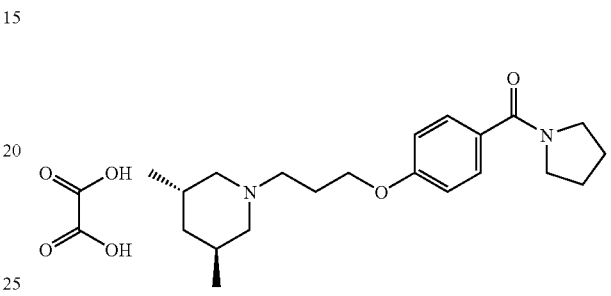

trans-1-{3-[4-(N,N-tetramethylenecarbamoyl)phenoxy]propyl}-3,5-dimethylpiperidine, oxalate Following the procedure described in example 1§A, but starting from 4-[3-(cis and trans-3,5-dimethylpiperidino)propoxy]benzoyl chloride, hydrochloride (700 mg) and pyrrolidine (500 µL) in dichloromethane (10 mL), gives 24 mg of trans-1-{3-[4-(N,N-tetramethylenecarbamoyl)phenoxy]propyl}-3,5-dimethylpiperidine, oxalate as a white powder.

¹H NMR: base (CDCl₃)

7.51 (d, J=8.7 Hz, 2H, arom), 6.90 (d, J=8.7 Hz, 2H, arom), 4.06 (t, J=6.0 Hz, 2H, CH₂O), 3.55 (m, 4H, 2 CH₂NCO), 2.5-1.8 (m, 14H, 3 CH₂N, 3 CH₂, 2 CH), 1.25 (dd, J=5.8 Hz, J=5.8 Hz, 2H, CH₂), 0.95 (2d, J=6.8 Hz, J=6.8 Hz, 6H, 2 CH₃).

EXAMPLE 3

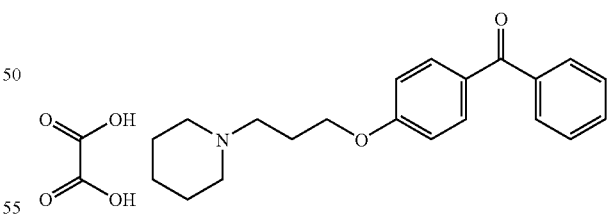

1-[3-(4-benzoylphenyl)propoxy]piperidine, oxalate

A Following the procedure described in example 1§D, but starting from 4-(3-chloropropoxy)benzophenone (1.37 g), piperidine (1 mL), potassium carbonate (2.07 g) and a catalytic amount of potassium iodide in N,N-dimethylformamide (25 mL) gives, after salt formation with oxalic acid (55 mg) in acetone (0.6 mL), 239 mg of 1-[3-(4-benzoylphenyl)propoxy]piperidine, oxalate as a white powder.

¹H NMR: oxalate (DMSO)

7.73 (d, J=8.8 Hz, 2H, arom), 7.67-7.53 (m, 5H, Ph), 7.07 (d, J=8.8 Hz, 2H, arom), 4.15 (t, J=6.0 Hz, 2H, CH$_2$O), 3.09 (m, 6H, 3 CH$_2$N), 2.15 (m, 2H, CH$_2$), 1.70 (m, 4H, 2 CH$_2$), 1.50 (m, 2H, CH$_2$).

B 4-(3-chloropropoxy)benzophenone can be prepared as follows:

Following the procedure described in example 1§E, but starting from 4-hydroxybenzophenone (0.99 g), potassium carbonate (3.45 g) and 1-bromo-3-chloropropane (2.5 mL) in N,N-dimethylformamide (7.5 mL) affords 1.4 g of 4-(3-chloropropoxy)benzophenone as a yellow oil.

Rf TLC (heptane/ethyl acetate 1/1)=0.5

EXAMPLE 4

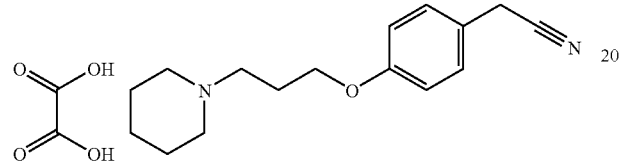

1-[3-(4-cyanomethylphenyl)propoxy]piperidine, oxalate

A Following the procedure described in example 1§D, but starting from 4-(3-chloropropoxy)phenylacetonitrile (698 mg), piperidine (658 µL) and potassium carbonate (1.38 g) in N,N-dimethylformamide (16 mL) gives, after dissolution in a mixture of diethyl ether (5 mL) and ethanol (1 mL), and salt formation with oxalic acid (191 mg) in acetone (0.5 mL), 493 mg of 1-[3-(4-cyanomethylphenyl)propoxy]piperidine, oxalate as a beige solid melting at 181° C.

$^1$H NMR: oxalate (DMSO)

7.24 (d, J=8.6 Hz, 2H, arom), 6.92 (d, J=8.6 Hz, 2H, arom), 4.00 (t, J=6.0 Hz 2H, CH$_2$O), 3.91 (s, 2H, CH$_2$CN), 3.05 (m, 6H, 3 CH$_2$N), 2.07 (m, 2H, CH$_2$), 1.70 (m, 4H, CH$_2$), 1.50 (m, 2H, CH$_2$).

B 4-(3-chloropropoxy)phenylacetonitrile can be prepared as follows:

Following the procedure described in example 1§E, but starting from 4-hydroxyphenylacetonitrile (4.65 g), potassium carbonate (24 g) and 1-bromo-3-chloropropane (17.3 mL) in N,N-dimethylformamide (23 mL) affords 6.86 g of 4-(3-chloropropoxy)phenylacetonitrile as a yellow solid.

Rf TLC (heptane/ethyl acetate 1/1)=0.67

EXAMPLE 5

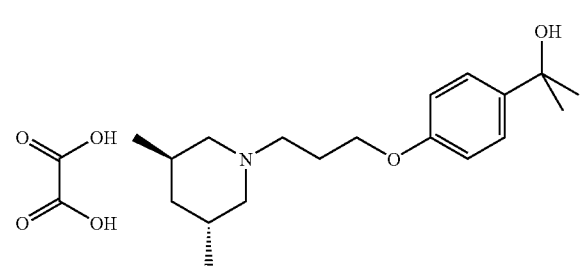

trans-1-{3-[4-(1-hydroxy-1-methylethyl)phenoxy]propyl}-3,5-dimethylpiperidine, oxalate

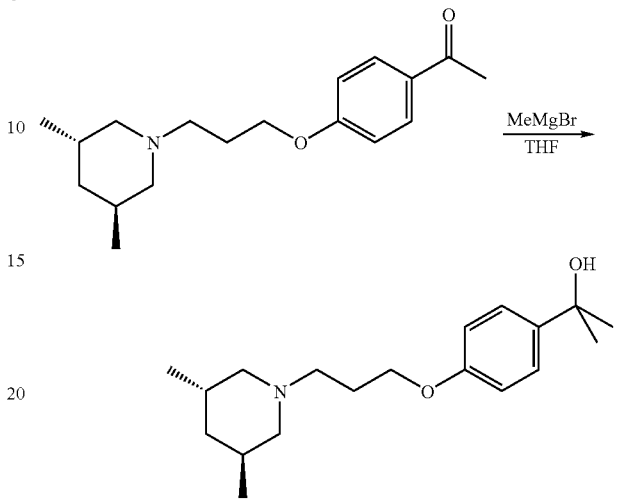

A solution of trans-1-[3-(4-acetylphenoxy)propyl]-3,5-dimethylpiperidine (289 mg) in tetrahydrofuran (1 mL) is stirred at room temperature under anhydrous atmosphere and a 2.61 M solution of methylmagnesium bromide in tetrahydrofuran (400 µL) is added dropwise. The mixture is stirred at room temperature for 3 h and quenched with a saturated aqueous solution of ammonium chloride. The solution is extracted with ethyl acetate and the combined extracts washed with water, dried over magnesium sulphate, concentrated under reduced pressure and purified by chromatography over silica gel with dichloro-methane/methanol 95/5 as eluent. Fractions containing the expected product are pooled and salted with 20 mg of oxalic acid to give 70 mg of trans-1-{3-[4-(1-hydroxy-1-methylethyl)-phenoxy]propyl}-3,5-dimethylpiperidine, oxalate as a pale yellow solid.

$^1$H NMR: oxalate (DMSO)

7.33 (d, J=8.6 Hz, 2H, arom), 6.82 (d, J=8.6 Hz, 2H, arom), 3.98 (t, J=6.0 Hz, 2H, CH$_2$O), 3.1-2.5 (m, 6H, 3 CH$_2$N), 2.05 (m, 4H, CH$_2$, 2 CH), 1.36 (m, 8H, 2 CH$_3$, CH$_2$), 0.96 (2d, J=6.7 Hz, J=6.7 Hz, 6H, 2 CH$_3$).

trans-1-[3-(4-acetylphenoxy)propyl]-3,5-dimethylpiperidine can be prepared as described in EP9905744

EXAMPLE 6

(RS)-1-{3-[4-(1-hydroxy-1-methylethyl)phenoxy]propyl}-3-methylpiperidine, oxalate A Following the procedure described in example 5, but starting from (RS)-1-{3-[4-(methoxycarbonyl)phenoxy]propyl}-3-methylpiperidine (146 mg) and a 2.61 M solution of methylmagnesium chloride in tetrahydrofuran (0.8 mL) affords, after salt formation with oxalic acid, 104 mg of (RS)-1-{3-[4-(1-hydroxy-1-methylethyl)phenoxy]propyl}-3-methylpiperidine, oxalate as a white powder.

¹H NMR: oxalate (DMSO)

7.34 (d, J=8.6 Hz, 2H, arom), 6.82 (d, J=8.6 Hz, 2H, arom), 3.98 (t, J=6.0 Hz, 2H, CH₂O), 3.33 (m, 2H, 2 CH₂N eq.), 3.06 (m, 2H, CH₂N), 2.70 (m, 1H, CH₂N ax.), 2.46 (m, 1H, CH₂N ax.), 2.05 (m, 2H, CH₂), 1.69 (m, 4H, CH₂, CH, 1 CH₂ eq.), 1.36 (s, 6H, 2 CH₃), 1.06 (m, 1H, CH₂ ax.), 0.88 (d, J=6.5 Hz, 3H, CH₃).

B (RS)-1-{3-[4-(methoxycarbonyl)phenoxy]propyl}-3-methylpiperidine can be prepared as follows:

Following the procedure described in example 1§D, but starting from methyl 4-(3-chloropropoxy)benzoate (458 mg), (RS)-3-methylpiperidine (1.2 mL), potassium carbonate (2.0 g) and a catalytic amount of potassium iodide in N,N-dimethylformamide (25 mL) gives 433 mg of (RS)-1-{3-[4-(methoxycarbonyl)-phenoxy]propyl}-3-methylpiperidine as a yellow solid.

Rf TLC (dichloromethane/methanol 90/10)=0.4

C Methyl 4-(3-chloropropoxy)benzoate can be prepared as follows:

Following the procedure described in example 1§E, but starting from methyl 4-hydroxybenzoate (15.2 g), potassium carbonate (65 g) and 1-bromo-3-chloropropane (50 mL) in N,N-dimethylformamide (100 mL) affords 22.5 g of methyl 4-(3-chloropropoxy)benzoate as an oil.

Rf TLC (heptane/ethyl acetate 2/1)=0.55

EXAMPLE 7

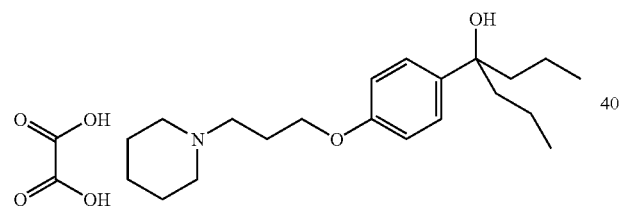

1-{3-[4-(1-hydroxy-1-propylbutyl)phenoxy]propyl}piperidine, oxalate

A

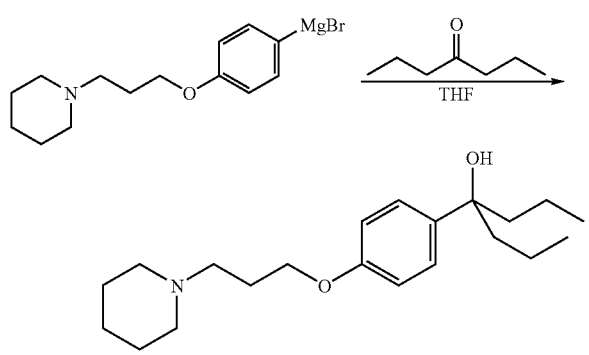

To a solution of 4-heptanone (471 mg) in tetrahydrofuran (4 mL) is added a solution of 4-(3-piperidinopropoxy)phenylmagnesium bromide in tetrahydrofuran (11 mL, 3.3 mmol). The mixture is stirred overnight at room temperature and quenched at 0° C. with a saturated aqueous solution of ammonium chloride (20 mL). The solution is extracted with ethyl acetate (20 mL) and the organic layer is washed with a saturated aqueous solution of ammonium chloride (20 mL), dried over magnesium sulphate, concentrated under reduced pressure and purified by chromatography over silica gel with a gradient dichloromethane/methanol from 98/2 to 95/5 as eluent. Fractions containing the expected product are pooled and concentrated under reduced pressure to give 1-{3-[4-(1-hydroxy-1-propylbutyl)-phenoxy]propyl}piperidine as a yellow oil. Salt formation with oxalic acid in ethanol and precipitation with diethyl oxide affords 1-{3-[4-(1-hydroxy-1-propylbutyl)-phenoxy]propyl}piperidine, oxalate as a white solid melting at 118° C.

¹H NMR: oxalate (DMSO)

7.23 (d, J=8.6 Hz, 2H, arom), 6.80 (d, J=8.6 Hz, 2H, arom), 3.98 (t, J=6.0 Hz, 2H, CH₂O), 3.08 (m, 6H, 3 CH₂N), 2.07 (m, 2H, CH₂), 1.8-1.3 (m, 10H, 5CH₂), 1.2-0.8 (m, 4H, 2CH₂), 0.72 (t, J=6.9 Hz, 6H, 2 CH₃).

B

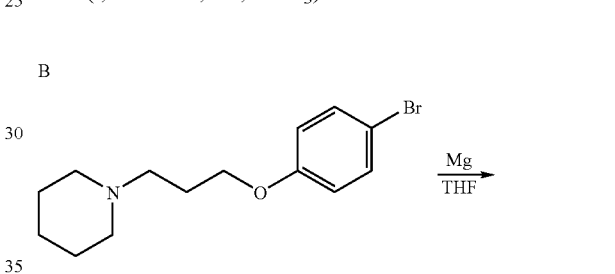

4-(3-piperidinopropoxy)phenylmagnesium bromide can be prepared as follows:

In a round bottomed flask are introduced magnesium turnings (0.29 g). The flask is air dried, cooled to room temperature and tetrahydrofuran (3 mL) is introduced. A 3 mL portion of a solution of 1-[3-(4-bromophenyl)propoxy]piperidine (2.98 g) in tetrahydrofuran (30 mL) is added. The reaction is started on a small sample in a test tube with 1,2-dibromoethane and a few additional magnesium turnings. The reaction mixture is then warmed and the rest of the solution of 1-[3-(4-bromophenyl)propoxy]piperidine added. The mixture is heated at 70° C. for three hours. The supernatant is taken with a syringe to give 33 mL (10 mmol) of 1-[3-(4-bromophenyl)propoxy]piperidine in tetrahydrofuran.

1-[3-(4-bromophenyl)propoxy]piperidine can be prepared as described in EP9905744

EXAMPLE 8

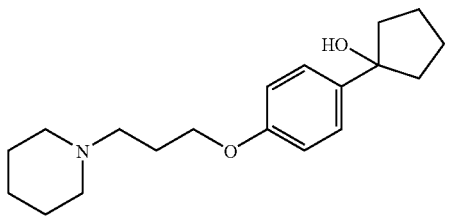

1-{3-[4-(1-hydroxycyclopentyl)phenoxy]
propyl}piperidine

Following the procedure described in example 7§A but starting from cyclopentanone (365 mL), tetrahydrofuran (4 mL) and a solution of 4-(3-piperidinopropoxy)phenylmagnesium bromide in tetrahydrofuran (11 mL, 3.3 mmol) affords, after salt formation with oxalic acid, 115 mg of 1-{3-[4-(1-hydroxycyclopentyl)phenoxy]propyl}piperidine $^1$H NMR: base (CDCl$_3$)

7.41 (d, J=6.7 Hz, 2H, arom), 6.87 (d, J=6.7 Hz, 2H, arom), 4.01 (t, J=6.0 Hz, 2H, CH$_2$O), 2.55 (m, 6H, 3 CH$_2$N), 2.15-1.75 (m, 10H, 5CH$_2$), 1.70 (m, 4H, CH$_2$), 1.50 (m, 2H, CH$_2$).

EXAMPLE 9

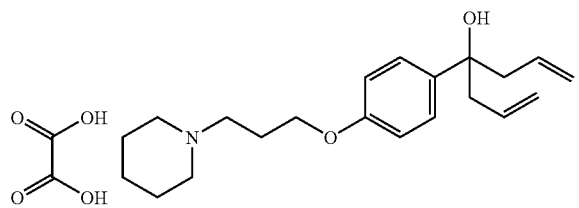

1-{3-[4-(1-hydroxy-1-allylbut-3-enyl)phenoxy]
propyl}piperidine, oxalate

Following the procedure described in example 5, but starting from 1-{3-[4-(methoxycarbonyl)phenoxy]propyl}piperidine (560 mg) and a 1 M solution of allylmagnesium bromide in diethyl oxide (6.8 mL) affords, after salt formation with oxalic acid, 165 mg of 1-{3-[4-(1-hydroxy-1-allylbut-3-enyl)phenoxy]propyl}-piperidine, oxalate as a white powder.

$^1$H NMR: oxalate (DMSO)

7.25 (d, J=8.7 Hz, 2H, arom), 6.81 (d, J=8.7 Hz, 2H, arom), 5.65 (m, 2H, 2 CH═), 4.89 (d, J=16.3 Hz, 2H, CH$_2$═), 4.88 (d, J=11.2 Hz, 2H, CH$_2$═), 3.97 (t, J=5.7 Hz, 2H, CH$_2$O), 3.3-2.7 (m, 6H, 3 CH$_2$N), 2.46 (m, 4H, CH$_2$CH═CH$_2$), 2.10 (m, 2H, CH$_2$), 1.70 (m, 4H, CH$_2$), 1.50 (m, 2H, CH$_2$).

EXAMPLE 10

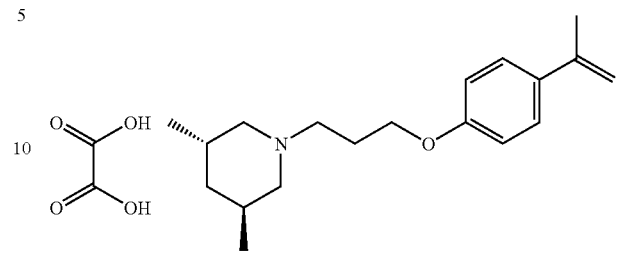

trans-1-{3-(4-isopropenylphenoxy)propyl]-3,5-dimethylpiperidine, oxalate

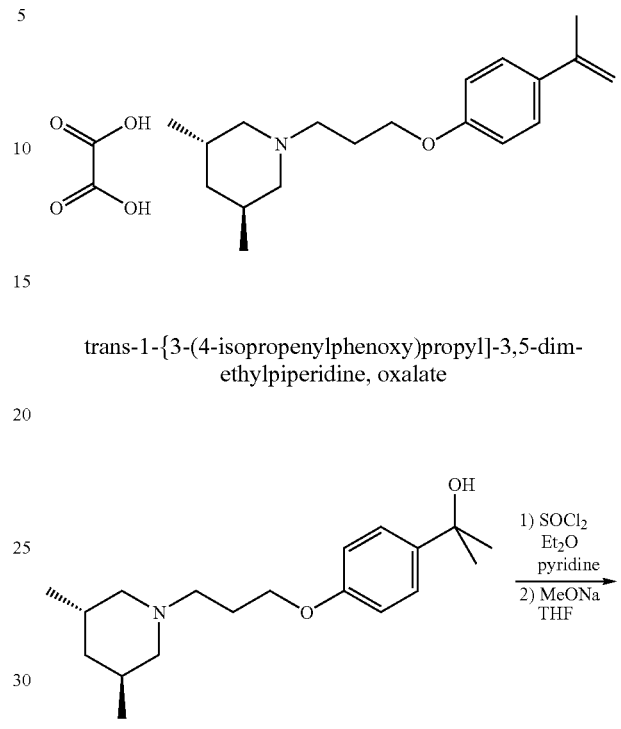

Thionyl chloride (50 µL) is added dropwise to a solution of trans-1-{3-[4-(1-hydroxy-1-methylethyl)phenoxy]propyl}-3,5-dimethylpiperidine (115 mg) in diethyl oxide (5 mL) and pyridine (35 µL) stirred at a temperature close to 0° C. The mixture is stirred for one hour at room temperature, concentrated under reduced pressure and diluted with anhydrous tetrahydrofuran (5 mL). To this solution is added freshly prepared sodium methylate (200 mg). The mixture is stirred at room temperature for two hours and purified by chromatography over silica gel with a gradient of dichloromethane/methanol from 82/2 to 95/5. Fractions containing the expected product are pooled and concentrated under reduced pressure to afford 50 mg of an orange oil which is dissolved in diethyl oxide (2 mL). A solution of oxalic acid (16 mg) in acetone (0.2 mL) is added to give, after filtration and drying, 11 mg of trans-1-{3-(4-isopropenylphenoxy)propyl]-3,5-dimethylpiperidine, oxalate as a white powder.

$^1$H NMR: base (CDCl$_3$)

7.40 (d, J=8.7 Hz, 2H, arom), 6.87 (d, J=8.7 Hz, 2H, arom), 5.28 (s, 1H, CH$_2$═), 4.99 (s, 1H, CH$_2$═), 4.04 (t, J=6.0 Hz, 2H, CH$_2$O), 2.40 (m, 4H, 2 CH$_2$N), 2.13 (s, 3H, CH$_3$C═), 2.00 (m, 2H, CH$_2$N), 1.93 (m, 4H, CH$_2$, 2 CH), 1.28 (dd, J=6.5 Hz, J=6.5 Hz, 2H, CH$_2$), 0.96 (2d, J=6.8 Hz, J=6.8 Hz, 6H, CH$_3$).

EXAMPLE 11

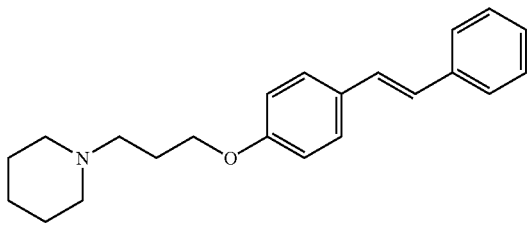

trans-1-{3-(4-styrylphenoxy)propyl]piperidine, oxalate

A Following the procedure described in example 1§D, but starting from 4-(3-chloropropoxy)stilbene (500 mg), piperidine (362 µL) and potassium carbonate (760 mg) in N,N-dimethylformamide (10 mL) gives, after salt formation with oxalic acid in ethanol, 426 mg of trans-1-{3-(4-styrylphenoxy)propyl]piperidine, oxalate as a white solid.

$^1$H NMR: oxalate (DMSO)

7.52 (m, 4H, arom), 7.33 (t, J=7.2 Hz, 2H, arom), 7.2 (m, 1H, arom), 7.18 (m, 1H, CH=), 7.06 (d, J=16.5 Hz, 1H, CH=) 6.92 (d, J=8.5 Hz, 2H, arom), 4.04 (t, J=5.6 Hz, 2H, CH$_2$O), 3.11 (m, 6H, 3 CH$_2$N), 2.11 (m, 2H, CH$_2$), 1.70 (m, 4H, CH$_2$), 1.50 (m, 2H, CH$_2$).

B 4-(3-chloropropoxy)stilbene can be prepared as follows:

Following the procedure described in example 1§E, but starting from 4-hydroxystilbene (2 g), potassium carbonate (7.04 g) and 1-bromo-3-chloropropane (5 mL) in N,N-dimethylformamide (10 mL) affords 2.06 g of 4-(3-chloropropoxy)stilbene as a white solid.

Rf TLC (heptane/ethyl acetate 1/1)=0.74

EXAMPLE 12

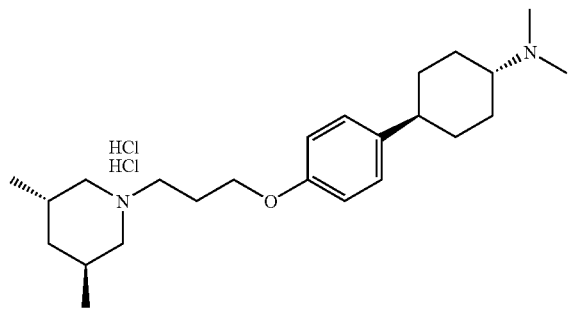

(3S,5S)-1-{3-[4-(trans-4-dimethylaminocyclohex-1-yl)phenoxy]propyl}-3,5-dimethylpiperidine, dihydrochloride A A mixture of (3S,5S)-1-(3-chloropropyl)-3,5-dimethylpiperidine, hydrochloride (2.04 g), trans-N,N-dimethyl-4-(4-hydroxyphenyl)cyclohexanamine (1.98 g) and potassium carbonate (5.0 g) in N,N-dimethylformamide is stirred at a temperature close to 60° C. overnight. The precipitate is filtrated. The filtrate is concentrated under reduced pressure, purified by chromatography over silica gel with a gradient dichloromethane/methanol/ammonia from 90/10/1 to 80/20/1. Fractions containing the expected product are pooled, concentrated under reduced pressure to give 2.25 g of (3S,5S)-1-{3-[4-(trans-4-dimethylaminocyclohex-1-yl)phenoxy]propyl}-3,5-dimethylpiperidine. The base is dissolved in ethanol and converted to the hydrochloride by addition of ethanolic hydrogen chloride. Recrystallisation in ethanol affords 1.93 g of (3S,5S)-1-{3-[4-(trans-4-dimethylaminocyclohex-1-yl)phenoxy]propyl}-3,5-dimethylpiperidine, dihydrochloride as a white powder melting at 240° C.

$^1$H NMR: (DMSO)

10.7 (bs, 1H, NH), 9.9 (bs, 1H, NH), 7.12 (d, J=8.4 Hz, 2H, arom), 6.84 (d, J=8.4 Hz, 2H, arom), 3.97 (t, J=5.9 Hz, 2H, CH2O), 3.30-3.05 (m, 6H, 3 CH$_2$N), 2.90 (m, 1H, CHN), 2.66 (m, 6H, 2 CH$_3$N), 2.45 (m, 1H, CHAr), 2.20-1.95 (m, 6H), 1.85 (m, 2H), 1.60-1.20 (m, 6H), 1.16 (d, J=7.4 Hz, 3H, CH$_3$C), 1.85 (d, J=6.5 Hz, 3H, CH$_3$C).

B (3S,5S)-1-(3-chloropropyl)-3,5-dimethylpiperidine, hydrochloride

A mixture of (3S,5S)-1-(3-hydroxypropyl)-3,5-dimethylpiperidine (1.91 g), thionyle chloride (0.96 mL) and dichloromethane (10 mL) is stirred at room temperature for 5 h, concentrated under reduced pressure and triturated in diethyl oxide to give 2.0 g of (3S,5S)-1-(3-chloropropyl)-3,5-dimethylpiperidine, hydrochloride as a beige powder used without further purification.

C (3S,5S)-1-(3-hydroxypropyl)-3,5-dimethylpiperidine

A mixture of (3S,5S)-3,5-dimethylpiperidine, hydrochloride (2.58 g), 3-chloropropanol (1.44 mL), potassium carbonate (3.58 g) and a catalytic amount of potassium iodide in acetone (10 mL) is stirred under reflux for 24 h. Precipitate is filtrated and rinsed with acetone. Filtrate is concentrated under reduced pressure and purified by chromatography over silica gel with a gradient dichloromethane/methanol/triethylamine from 80/20/1 to 50/50/1 to give 1.9 g of (3S,5S)-1-(3-hydroxypropyl)-3,5-dimethylpiperidine as a yellow oil.

D trans-N,N-dimethyl-4-(4-hydroxyphenyl)cyclohexanamine

To a solution of trans-4-(4-hydroxyphenyl)cyclohexanamine, hydrochloride (3.42 g) in dioxane (75 mL), aqueous formaldehyde solution (11.2 mL, 38%) and phosphorous acid monosodium salt (150 mL, 1N) is added concentrated aqueous sodium hydroxide solution until pH is neutral. The solution is stirred at a temperature close to 60° C. for one hour, cooled to room temperature and brought to pH 7-8 by addition of concentrated aqueous sodium hydroxide solution. Evaporation of dioxane causes precipitation. The precipitate is filtrated and washed with water. Purification by chromatography over silica gel with a gradient dichloromethane/methanol/ammonia from 90/10/1 to 70/30/1 and triturating in diethyl ether afford a crude product that is further purified by chromatography over silica gel with dichloromethane/methanol/ammonia 80/20/1 to give trans-N,N-dimethyl-4-(4-hydroxyphenyl)cyclohexanamine as a pale yellow powder.

E trans-4-(4-hydroxyphenyl)cyclohexanamine Can be Prepared as Described in WO 01/81295 (Warner-Lambert Company) or as Follows A suspension of trans-N-benzyl-4-(4-hydroxyphenyl)cyclohexanamine (7.69 g) and palladium over charcoal (800 mg) in methanol (300 mL) is stirred at a temperature close to 40° C. for 8 h under a pressure of 15 bar of dihydrogene. Filtration over celite and evaporation of the solvent under reduced pressure affords 4.9 g of trans-4-(4-hydroxyphenyl) cyclohexanamine as a white powder. trans-N-benzyl-4-(4-hydroxyphenyl)cyclohexanamine can be prepared as described in WO 01/81295 (Warner-Lambert Company).

F Alternative preparation trans-N,N-dimethyl-4-(4-hydroxyphenyl)-cyclohexanamine To a solution of trans-4-(4-hydroxyphenyl)-N-methylcyclohexanamine, hydrochloride (1.15 g) in dioxane (50 mL), aqueous formaldehyde solution (3.7 mL, 37%) and phosphorous acid monosodium salt (49 mL, 1N) is added concentrated aqueous sodium hydroxide solution until pH is neutral. The solution is stirred at a temperature close to 60° C. for 2 h, cooled to room temperature and brought to pH 7-8 by addition of concentrated aqueous sodium hydroxide solution. Evaporation of dioxane causes precipitation. The precipitate is filtrated and washed with water then diethyl ether to give 1.78 g of trans-N,N-dimethyl-4-(4-hydroxyphenyl)cyclohexanamine as a white solid.

G trans-4-(4-hydroxyphenyl)-N-methylcyclohexanamine

A mixture of 4-(4-hydroxyphenyl)cyclohexanone (3 g) in tetrahydrofuran (20 mL) and a solution of methylamine in tetrahydrofuran (7.9 mL, 2 M) is stirred overnight at room temperature, concentrated under reduced pressure, dissolved in a mixture of dichloromethane and methanol (30 mL, 1/1) and cooled at a temperature close to 0° C. Sodium borohydride (822 mg) is added portionwise and the mixture is stirred at room temperature for one hour. The precipitate is filtered and washed with diethyl oxide to give 1.1 g of trans-4-(4-hydroxyphenyl)-N-methylcyclohexanamine used without further purification.

EXAMPLE 13

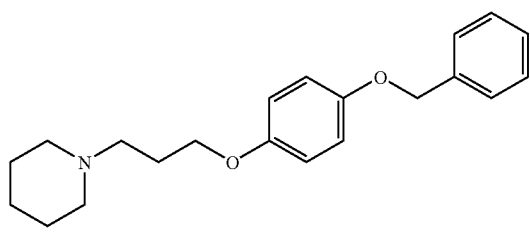

1-{3-[4-(benzyloxy)phenoxy]propyl}piperidine, oxalate

A Following the procedure described in example 1§D, but starting from O-benzyl-4-(3-chloropropoxy)phenol (500 mg), piperidine (357 µL) and potassium carbonate (749 mg) in N,N-dimethylformamide (10 mL) gives, after salt formation with oxalic acid in ethanol, 459 mg of 1-{3-[4-(benzyloxy)phenoxy]propyl}piperidine, oxalate as a white solid.

$^1$H NMR: oxalate (DMSO)

7.34 (m, 5H, arom), 6.91 (d, J=9.2 Hz, 2H, arom), 6.83 (d, J=9.2 Hz, 2H, arom), 5.00 (s, 2H, PhCH$_2$O), 3.93 (t, J=6.0 Hz, 2H, CH$_2$O), 3.07 (m, 6H, 3 CH$_2$N), 2.05 (m, 2H, CH$_2$), 1.69 (m, 4H, CH$_2$), 1.50 (m, 2H, CH$_2$).

B O-benzyl-4-(3-chloropropoxy)phenol can be prepared as follows:

Following the procedure described in example 1§E, but starting from 4-benzyloxyphenol (2 g), potassium carbonate (6.90 g) and 1-bromo-3-chloropropane (4.94 mL) in N,N-dimethylformamide (10 mL) affords 2.07 g of O-benzyl-4-(3-chloropropoxy)phenol as a white solid.

Rf TLC (heptane/ethyl acetate 1/1)=0.8

EXAMPLE 14

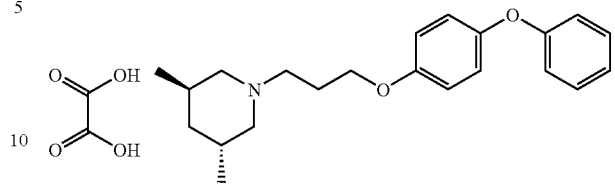

trans-1-{3-[4-(phenoxy)phenoxy]propyl}-3,5-dimethylpiperidine

A Following the procedure described in example 1§D, but starting from 4-(3-chloropropoxy)-O-phenylphenol (130 mg), trans-3,5-dimethylpiperidine (112 mg), potassium carbonate (300 mg) and a catalytic amount of potassium iodide in N,N-dimethylformamide (10 mL) gives, after salt formation with oxalic acid in ethanol, 65 mg of trans-1-{3-[4-(phenoxy)phenoxy]propyl}-3,5-dimethylpiperidine as a white solid.

$^1$H NMR: oxalate (DMSO)

7.32 (m, 2H, arom), 7.95 (m, 7H, arom), 3.99 (t, J=5.8 Hz, 2H, CH$_2$O), 3.2-2.5 (m, 6H, 3 CH$_2$N), 2.06 (m, 4H, CH$_2$, 2 CH), 1.35 (m, 2H, CH$_2$), 0.96 (2d, J=5.9 Hz, J=5.9 Hz, 6H, 2 CH$_3$).

B 4-(3-chloropropoxy)-O-phenylphenol can be prepared as follows:

Following the procedure described in example 1§E, but starting from 4-phenoxyphenol (950 mg), potassium carbonate (3.2 g) and 1-bromo-3-chloropropane (2.5 mL) in N,N-dimethylformamide (5 mL) affords 0.50 g of 4-(3-chloropropoxy)-O-phenylphenol used without any further purification.

EXAMPLE 15

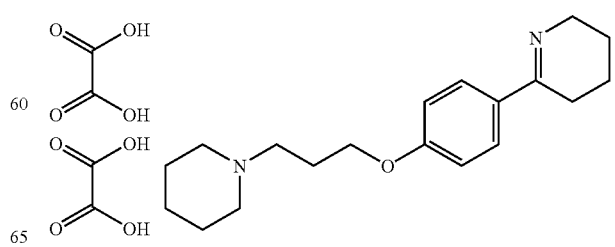

6-[4-(3-piperidinopropoxy)phenyl]-2,3,4,5-tetrahydropyridine, dioxalate

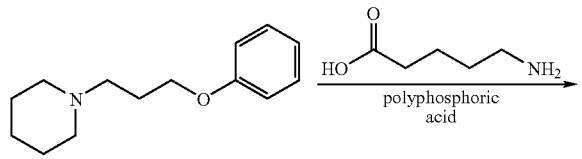

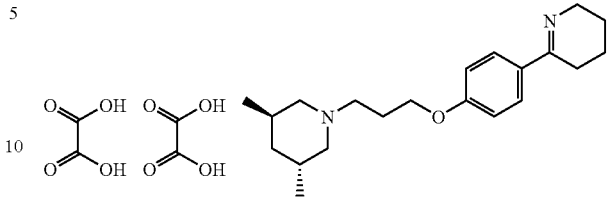

A mixture of 1-(3-phenoxypropyl)piperidine, oxalate (0.2 g), 5-aminopentanoic acid (0.076 g) and polyphosphoric acid (2 g) is stirred at a temperature close to 100° C. for one hour. The mixture is cooled to room temperature, diluted with water (25 mL), made alkaline through addition of concentrated aqueous sodium hydroxide solution with external cooling and extracted twice with ethyl acetate (25 mL). The organic layers are pooled, washed with a saturated aqueous solution of sodium chloride (25 mL), dried over magnesium sulphate and purified by chromatography over silica gel. Fractions containing the expected product are pooled, concentrated under reduced pressure to give 0.172 g of 6-[4-(3-piperidinopropoxy)phenyl]-2,3,4,5-tetrahydropyridine which is dissolved in ethanol (2 mL). A solution of oxalic acid (0.104 g) in ethanol (0.5 mL) is added. The precipitate that appears on standing is filtered, rinsed with ethanol and dried to afford 200 mg of 6-[4-(3-piperidinopropoxy)phenyl]-2,3,4,5-tetrahydropyridine, oxalate as a white powder melting at 104° C.

$^1$H NMR: oxalate (DMSO)

7.88 (d, J=8.7 Hz, 2H, arom), 7.06 (d, J=8.7 Hz, 2H, Arom), 4.11 (t, J=5.9 Hz, 2H, CH$_2$O), 3.67 (m, 2H, CH$_2$N=), 3.3-2.8 (m, 8H, 3 CH$_2$N, CH$_2$C=N), 2.13 (m, 2H, CH$_2$), 1.72 (m, 8H, 4CH$_2$), 1.50 (m, 2H, CH$_2$).

B 1-(3-phenoxypropyl)piperidine, oxalate can be prepared as follows:

Following the procedure described in example 1§D, but starting from O-(3-chloropropyl)phenol (382 mg), piperidine (0.79 mL), potassium carbonate (1.66 g) and a catalytic amount of potassium iodide in N,N-dimethylformamide (20 mL) gives, after salt formation with oxalic acid in ethanol, 729 mg of 1-(3-phenoxypropyl)piperidine, oxalate as a white solid melting at 183° C.

EXAMPLE 16 trans-6-{4-[3-(3,5-dimethylpiperidino)propoxy]phenyl}-2,3,4,5-tetrahydropyridine, dioxalate A Following the procedure described in example 1§D, but starting from 6-[4-(3-chloropropoxy)phenyl]-2,3,4,5-tetrahydropyridine (755 mg), a commercial mixture of cis- and trans-3,5-dimethylpiperidine (0.796 mL), potassium carbonate (1.24 g) and a catalytic amount of potassium iodide in N,N-dimethylformamide (20 mL) gives, after two chromatographies over silica gel, the first one with a gradient dichloromethane/methanol from 98/2 to 95/5, the second one with a gradient diethyl oxide/ligroin/triethylamine from 50/49/1 to 75/25/1 and salt formation with oxalic acid in ethanol and diethyl oxide, 83 mg of trans-6-{4-[3-(3,5-dimethylpiperidino)propoxy]phenyl}-2,3,4,5-tetrahydropyridine, dioxalate as a white solid melting at 72° C.

$^1$H NMR: oxalate (DMSO)

7.89 (d, J=8.7 Hz, 2H, arom), 7.07 (d, J=8.7 Hz 2H, arom), 4.11 (t, J=5.9 Hz 2H, CH$_2$O), 3.68 (m, 2H, CH$_2$N=), 3.2-2.6 (m, 8H, 3 CH$_2$N, CH$_2$C=N), 2.11 (m, 4H, CH$_2$, 2 CH), 1.77 (m, 4H, 2CH$_2$), 1.37 (m, 2H, CH$_2$), 0.96 (2d, J=5.9 Hz, J=5.9 Hz, 6H, 2 CH$_3$).

B 6-[4-(3-chloropropoxy)phenyl]-2,3,4,5-tetrahydropyridine can be prepared as follows:

Following the procedure described in example 15§A, but starting from O-(3-chloropropyl)phenol (3.55 g), 5-aminopentanoic acid (2.39 g) and polyphosphoric acid (36 g) gives 1.563 g of 6-[4-(3-chloropropoxy)phenyl]-2,3,4,5-tetrahydropyridine.

Rf TLC (dichloromethane/methanol 95/5)=0.3

O-(3-chloropropyl)phenol can be purchased at Aldrich Rare Chemicals and Salor.

EXAMPLE 17

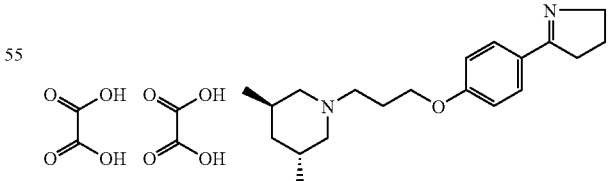

trans-1-{3-[4-(4,5-dihydro-3H-pyrrol-2-yl)phenoxy]propyl}-3,5-dimethylpiperidine, dioxalate A Following the procedure described in example 1§D, but starting from 2-[4-(3-chloropropoxy)phenyl]-4,5-dihydro- 3H-pyrrole (832 mg), a commercial mixture of cis- and trans-3,5-dimethylpiperidine (0.929 mL), potassium carbonate (1.45 g) and a catalytic amount of potassium iodide in N,N-dimethylformamide (20 mL) gives, after two chromatographies over silica gel, the first one with a gradient dichloromethane/methanol from 98/2 to 95/5, the second one with diethyl oxide/ligroin/triethylamine 50/49/1 and salt formation with oxalic acid in ethanol and diethyl oxide, 254 mg of trans-1-{3-[4-(4,5-dihydro-3H-pyrrol-2-yl)phenoxy]propyl}-3,5-dimethylpiperidine, dioxalate as a white solid melting at 83° C.

$^1$H NMR: oxalate (DMSO)

7.87 (d, J=8.7 Hz, 2H, arom), 7.03 (d, J=8.7 Hz, 2H, arom), 4.09 (t, J=5.9 Hz, 2H, CH$_2$O), 3.94 (m, 2H, CH$_2$N=), 3.2-2.5 (m, 8H, 3 CH$_2$N, CH$_2$C=N), 2.03 (m, 6H, 2 CH$_2$, 2 CH), 1.35 (m, 2H, CH$_2$), 0.96 (2d, J=5.6 Hz, J=5.6 Hz, 6H, 2 CH$_3$).

B 2-[4-(3-chloropropoxy)phenyl]-4,5-dihydro-3H-pyrrole can be prepared as follows:

Following the procedure described in example 1§A, but starting from O-(3-chloropropyl)phenol (3.41 g), 4-aminobutanoic acid (2.06 g) and polyphosphoric acid (36 g) gives 0.44 g of 2-[4-(3-chloropropoxy)phenyl]-4,5-dihydro-3H-pyrrole.

Rf TLC (dichloromethane/methanol 95/5)=0.23

EXAMPLE 18

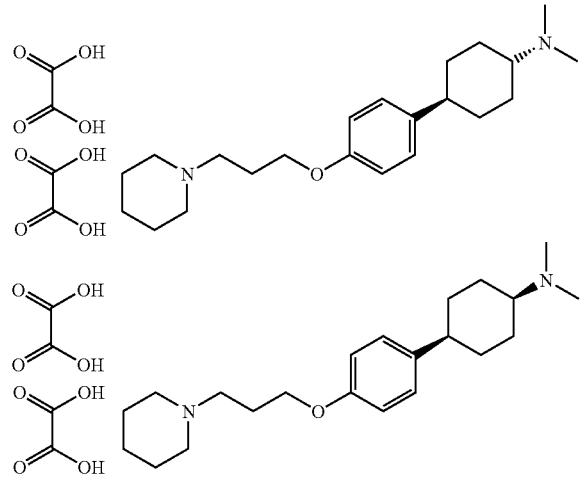

1-{3-[4-(cis-4-dimethylaminocyclohex-1-yl)phenoxy]propyl}piperidine, dioxalate and 1-{3-[4-(trans-4-dimethylaminocyclohex-1-yl)phenoxy]propyl}-piperidine, dioxalate

A

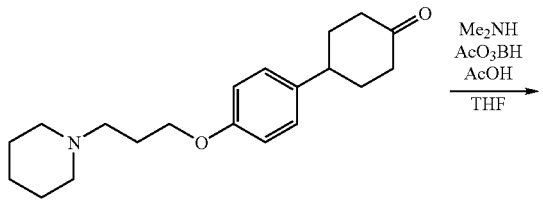

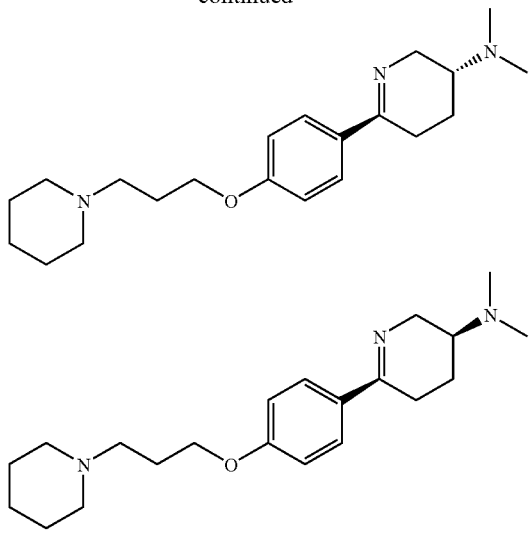

To a solution of 1-{3-[4-(4-oxocyclohexyl)phenoxy]propyl}piperidine (740 mg) in tetrahydrofuran (9 mL), are added successively a 2M solution of dimethylamine in tetrahydrofuran (2.3 mL), acetic acid (141 μL) and sodium triacetoxy-borohydride (845 mg). The mixture is stirred for three hour at room temperature.

An additional amount of a 2M solution of dimethylamine in tetrahydrofuran (0.7 mL), sodium triacetoxyborohydride (253 mg) and acetic acid (42 μL) is added. The mixture is stirred for one hour at room temperature, then a saturated aqueous solution of sodium hydrogenocarbonate (30 mL) is added. The mixture is extracted with ethyl acetate (three times 50 mL). The combined extracts are dried over magnesium sulphate, concentrated under reduced pressure and purified by chromatography over silica gel with a gradient ligroin/diethyloxide/triethylamine/methanol from 80/20/1/0.1 to 20/80/1/0.1 then with a gradient diethyloxide/triethylamine/methanol from 100/1/0.1 to 90/1/10. Fractions containing the products are pooled and concentrated under reduced pressure.

The following products are obtained in order of elution: 348 mg of 1-{3-[4-(4-dimethylaminocyclohex-1-yl)phenoxy]propyl}piperidine (isomer A) as a yellow oil and 187 mg of 1-{3-[4-(cis-4-dimethylaminocyclohex-1-yl)phenoxy]propyl}piperidine (isomer B) as a yellow solid.

These two isomers are separately salted with 182 mg and 98 mg of oxalic acid respectively in ethanol to give 466 mg of 1-{3-[4-(4-dimethylaminocyclohex-1-yl)phenoxy]propyl}piperidine, dioxalate (isomer A) and 280 mg of 1-{3-[4-(4-dimethylaminocyclohex-1-yl)phenoxy]propyl}piperidine, dioxalate (isomer B)

$^1$H NMR: oxalate (DMSO)

Isomer A:

7.19 (d, J=8.5 Hz, 2H, arom), 6.83 (d, J=8.5 Hz, 2H, arom), 3.96 (t, J=5.9 Hz, 2H, CH$_2$O), 2.90 (m, 7H, 3 CH$_2$N, CHN), 2.62 (m, 6H, 2 CH$_3$N), 2.47 (m, 1H, CHAr), 2.0-1.3 (m, 16H, 8CH$_2$).

Isomer B:

7.09 (d, J=8.6 Hz, 2H, arom), 6.82 (d, J=8.6 Hz, 2H, arom), 3.94 (t, J=6.0 Hz, 2H, CH$_2$O), 3.07 (m, 1H, CHN), 2.82 (m, 6H, 3 CH$_2$N), 2.65 (m, 6H, 2 CH$_3$N), 2.38 (m, 1H, CHAr), 1.90 (m, 6H, 3CH$_2$), 1.60 (m, 10H, 5CH$_2$).

B

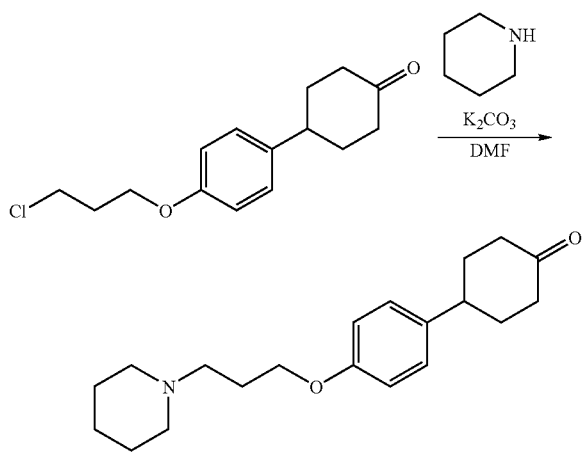

1-{3-[4-(4-oxocyclohexyl)phenoxy]propyl}piperidine can be prepared as follows:

A suspension of potassium carbonate (3.11 g) in a mixture of 4-[4-(3-chloropropoxy)phenyl]cyclohexanone (2 g), piperidine (2.22 mL) and N,N-dimethylformamide (40 mL) is heated for three hour at a temperature close to 110° C., then stirred for twenty hour at room temperature. The mixture is concentrated under reduced pressure and dissolved in ethyl acetate (150 mL) and water (150 mL). The organic phase is washed twice with water (100 mL), dried over magnesium sulphate, concentrated under reduced pressure and purified by chromatography over silica gel with a gradient dichloromethane/methanol from 95/5 to 90/10. Fractions containing the product are pooled and concentrated under reduced pressure affording 1.94 g of 1-{3-[4-(4-oxocyclohexyl)phenoxy]propyl}-piperidine as a yellow solid used without further purification.

C

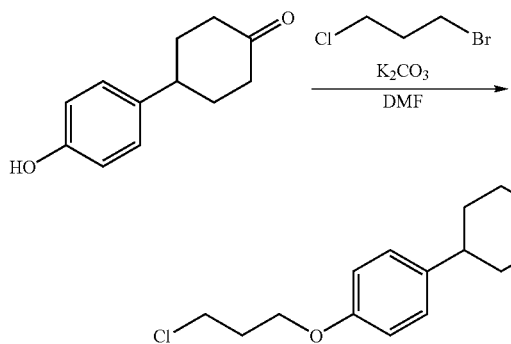

4-[4-(3-chloropropoxy)phenyl]cyclohexanone can be prepared as follows:

A suspension of potassium carbonate (12.4 g) in a mixture of 4-(4-hydroxyphenyl)cyclohexanone (3.42 g) and N,N-dimethylformamide (18 mL) is stirred for 24 h at room temperature. Diethyl oxide (63 mL) is added and the mixture is filtered. The insoluble part is rinsed twice with diethyl oxide (15 mL). Organic phases are pooled and washed with water (50 then 30 mL), dried over magnesium sulphate and concentrated under reduced pressure affording 4.6 g of 4-[4-(3-chloropropoxy)phenyl]cyclohexanone as a white solid used without further purification.

EXAMPLE 19

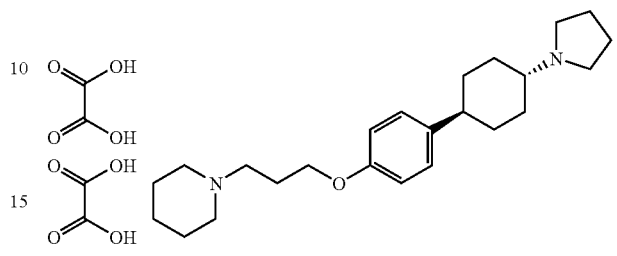

1-{3-[4-(cis-4-tetramethylenaminocyclohex-1-yl)
phenoxy]propyl}piperidine, dioxalate and 1-{3-[4-
(trans-4-tetramethylenaminocyclohex-1-yl)phenoxy]
propyl}-piperidine, dioxalate Following the procedure described in example 18§A, but starting from 1-{3-[4-(4-oxocyclohexyl)phenoxy] propyl}piperidine (0.5 g), pyrrolidine (159 μL), acetic acid (91 μL) and sodium triacetoxyborohydride (504 mg) in tetrahydrofuran (6 mL), the following products are obtained in order of elution, after salt formation with oxalic acid, 292 mg of 1-{3-[4-(4-pyrrolidinocyclohexyl)phenoxy] propyl}piperidine (isomer A) melting at 168° C. and 168 mg of 1-{3-[4-(4-pyrrolidinocyclohexyl)-phenoxy] propyl}piperidine (isomer B) melting at 160° C.

$^1$H NMR: oxalate (DMSO)

Isomer A:

7.19 (d, J=8.5 Hz, 2H, arom), 6.81 (d, J=8.5 Hz, 2H, arom), 3.96 (t, J=5.9 Hz, 2H, CH$_2$O), 3.17 (m, 4H, 2 CH$_2$N), 3.09 (m, 1H, CHN), 2.88 (m, 6H, 3 CH$_2$N), 2.59 (m, 1H, CHAr), 2.0-1.3 (m, 20H, 10CH$_2$).

Isomer B:

7.10 (d, J=8.5 Hz, 2H, arom), 6.82 (d, J=8.5 Hz, 2H, arom), 3.96 (t, J=5.9 Hz, 2H, CH$_2$O), 3.15 (m, 11H, 5 CH$_2$N, CHN), 2.40 (m, 1H, CHAr), 2.2-1.3 (m, 20H, 10CH$_2$).

EXAMPLE 20

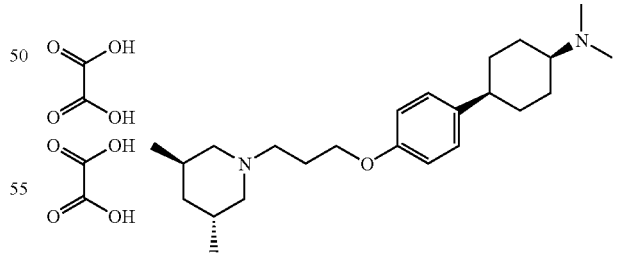

trans-1-{3-[4-(cis-4-dimethylaminocyclohex-1-yl)
phenoxy]propyl}-3,5-dimethylpiperidine, dioxalate
and trans-1-{3-[4-(trans-4-dimethylaminocyclohex-
1-yl)-phenoxy]propyl}-3,5-dimethylpiperidine, dioxalate A Following the procedure described in example 18§A, but starting from trans-3,5-dimethyl-1-{3-[4-(4-oxocyclohexyl)

phenoxy]propyl}piperidine (780 mg), a 2M solution of dimethylamine in tetrahydrofuran (1.36 mL), acetic acid (136 μL) and sodium triacetoxyborohydride (722 mg) in tetrahydrofuran (8 mL), the following products are obtained in order of elution, after salt formation with oxalic acid, 292 mg of trans-3,5-dimethyl-1-{3-[4-(4-dimethylaminocyclohexyl)phenoxy]propyl}-piperidine (isomer A) melting at 98° C. and 393 mg of trans-3,5-dimethyl-1-{3-[4-(4-dimethylaminocyclohexyl)phenoxy]propyl}piperidine (isomer B) melting at 162° C.

$^1$H NMR: oxalate (DMSO)

Isomer A:

7.19 (d, J=8.5 Hz, 2H, arom), 6.82 (d, J=8.5 Hz, 2H, arom), 3.95 (t, J=5.9 Hz, 2H, CH$_2$O), 3.09 (m, 1H, CHN), 2.68 (m, 10H, 2 CH$_2$N, 2 CH$_3$N), 2.46 (m, 3H, CH$_2$N, CHAr), 2.0-1.5 (m, 12H, 5 CH$_2$, 2 CH), 1.29 (m, 2H, CH$_2$), 0.92 (2d, J=6.8 Hz, J=6.8 Hz, 6H, 2 CH$_3$).

Isomer B:

7.10 (d, J=8.5 Hz, 2H, arom), 6.82 (d, J=8.5 Hz, 2H, arom), 3.95 (t, J=5.9 Hz, 2H, CH$_2$O), 3.14 (m, 1H, CHN), 2.72 (m, 10H, 2 CH$_2$N, 2 CH$_3$N), 2.46 (m, 3H, CH$_2$N, CHAr), 2.1-1.8 (m, 8H, CH$_2$, 2 CH, 4 CH$_2$ eq.), 1.7-1.2 (m, 6H, CH$_2$, 4 CH$_2$ ax.), 0.92 (2d, J=6.8 Hz, J=6.8 Hz, 6H, 2 CH$_3$).

B trans-3,5-dimethyl-1-{3-[4-(4-oxocyclohexyl)phenoxy]propyl}piperidine can be prepared as follows:

Following the procedure described in example 18§B, but starting from potassium carbonate (1.71 g), 4-[4-(3-chloropropoxy)phenyl]cyclohexanone. (1.5 g), trans-3,5-dimethylpiperidine hydrochloride (1.01 g) and N,N-dimethylformamide (20 mL), purifying the crude with two chromatographies with a gradient heptane/ethyl acetate from 4/1 to 0/1 for the first one and ligroin/diethyl oxide/triethylamine from 80/20/1 to 50/50/1 for the second one, 303 mg of trans-3,5-dimethyl-1-{3-[4-(4-oxocyclohexyl)phenoxy]-propyl}piperidine is obtained.

C

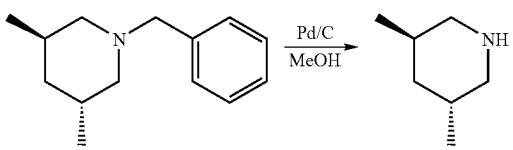

trans-3,5-dimethylpiperidine hydrochloride can be prepared as follows:

A suspension of 10% palladium on charcoal (1.5 g) in a mixture of trans-1-benzyl-3,5-dimethylpiperidine (7.65 g) and methanol (100 mL) is stirred under 15 bar of dihydrogene at 40° C. for 15 h. The reacting medium is filtered over a pad of celite and an etheral solution of hydrochloric acid is added. The hydrochloride is filtered and dried to give 3.43 g of trans-3,5-dimethylpiperidine hydrochloride as a pink solid used without further purification.

$^1$H NMR: hydrochloride (DMSO)

2.90 (m, 2H, CH$_2$N), 2.63 (m, 2H, CH$_2$N), 1.95 (m, 2H, 2 CH), 1.37 (dd J=5.7 Hz, J=5.7 Hz, 2H, CH$_2$), 0.95 (2d, J=7.1 Hz, J=7.1 Hz, 6H, 2 CH$_3$).

D

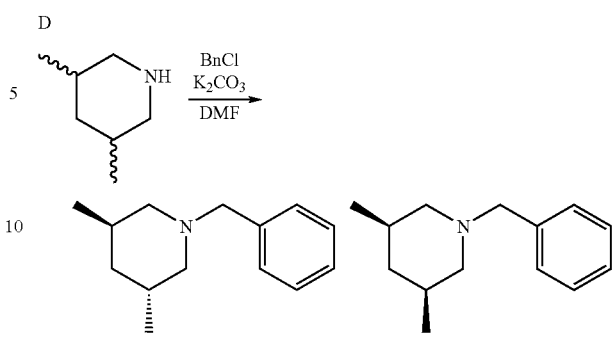

trans-1-benzyl-3,5-dimethylpiperidine can be prepared as follows:

A suspension of potassium carbonate (83 g) in a mixture of benzyl chloride (37 g), 3,5-dimethylpiperidine (30 g of acommercial mixture of cis and trans isomers) and N,N-dimethylformamide (200 mL) is stirred for 15 h at a temperature close to 60° C. The mixture is filtered, concentrated under reduced pressure and diluted in ethyl acetate. The organic phase is washed with water, dried over magnesium sulphate, concentrated under reduced pressure and purified by chromatography over silica gel with a mixture diethyl oxide/ligroin/triethylamine 20/80/1 as eluent to give 8 g of trans-1-benzyl-3,5-dimethylpiperidine as a colourless oil used without further purification.

$^1$H NMR (DMSO)

7.28 (m, 5H, arom), 3.52 (d, J=13.5 Hz, 1H, CH$_2$Ph), 3.37 (d, J=13.5 Hz, 1H, CH$_2$Ph), 2.38 (m, 2H, CH$_2$N), 2.06 (m, 2H, CH$_2$N), 1.90 (m, 2H, 2 CH), 1.29 (dd, J=5.7 Hz, J=5.7 Hz, 2H, CH$_2$), 0.96 (2d, J=7.1 Hz, J=7.1 Hz, 6H, 2 CH$_3$).

EXAMPLE 21

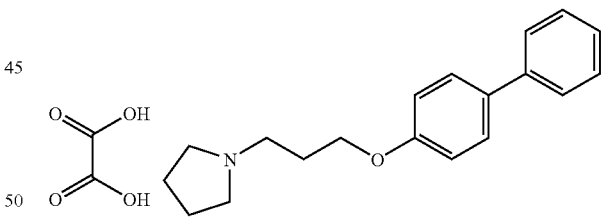

1-{3-[(biphenyl-4-yl)oxy]propyl}pyrrolidine, oxalate

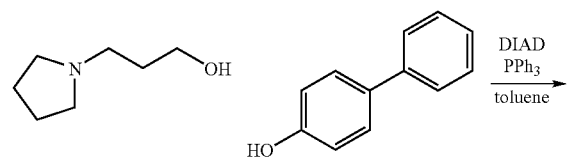

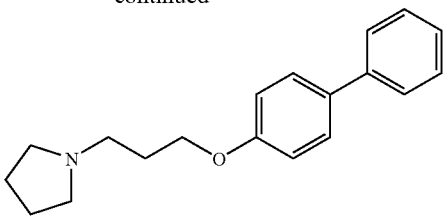

A mixture of 1-(3-hydroxypropyl)pyrrolidine (400 mg), triphenylphosphine (812 mg) in toluene (18 mL) is stirred for five minutes at room temperature, 1-hydroxybiphenyl (493 mg) is then added. The mixture is cooled and diisopropyl azodicarboxylate (609 μL) is added. The mixture is stirred for 48 hours room temperature, concentrated under reduced pressure and diluted with ethyl acetate. The organic layer is washed with water and extracted with an aqueous 1N hydrochloric solution. The aqueous phase is washed with ethyl acetate, then made alkaline with an aqueous 5N sodium hydroxide solution and extracted twice with ethyl acetate. These extracts are pooled, dried over magnesium sulphate, concentrated under reduced pressure, diluted with diethyl oxide and mixed with a solution of oxalic acid (169 mg) dissolved in acetone. The precipitate is filtered, washed with diethyl oxide and dried to give 480 mg of 1-{3-[(biphenyl-4-yl)oxy]propyl}pyrrolidine, oxalate as a white solid melting at 201° C.

$^1$H NMR: oxalate (DMSO)

7.58 (m, 4H, arom), 7.40 (m, 2H, arom), 7.27 (m, 1H, arom), 7.00 (d, J=8.7 Hz, 2H, arom), 4.06 (t, J=6.0 Hz, 2H, CH$_2$O), 3.22 (m, 6H, 3 CH$_2$N), 2.10 (m, 2H, CH$_2$), 1.91 (m, 4H, 2CH$_2$).

1-(3-hydroxypropyl)pyrrolidine can be obtained as described by J. Cossy and M. Guha, *Tetrahedron Lett.*, 35(11) 1715-8 (1994)

EXAMPLE 22

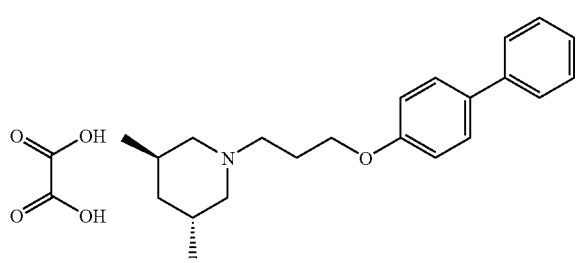

trans-1-{3-[(biphenyl-4-yl)oxy]propyl}-3,5-dimethylpiperidine, oxalate

Following the procedure described in example 1§D, but starting from 1-(3-chloropropoxy)biphenyl (1.23 g), a commercial mixture of cis and trans-3,5-dimethylpiperidine (1.32 mL), potassium carbonate (2.07 g) and a catalytic amount of potassium iodide in N,N-dimethylformamide (20 mL) gives, after salt formation with oxalic acid (85 mg), 349 mg of trans-1-{3-[(biphenyl-4-yl)oxy]propyl}-3,5-dimethylpiperidine, oxalate as a white powder melting at 176° C.

$^1$H NMR: oxalate (DMSO)

7.58 (m, 4H, arom), 7.40 (m, 2H, arom), 7.29 (m, 1H, arom), 7.00 (d, J=8.6 Hz, 2H, arom), 4.05 (t, J=5.8 Hz, 2H, CH$_2$O), 3.05 (m, 4H, 2 CH$_2$N), 2.75 (m, 2H, CH$_2$N), 2.08 (m, 4H, CH$_2$, 2 CH), 1.37 (m, 2H, CH$_2$), 0.96 (2d, J=6.8 Hz, J=6.8 Hz, 6H, 2 CH$_3$).

1-(3-chloropropoxy)biphenyl can be prepared as described by A. Rampa et al., *J. Med. Chem.* 44(23) 3810-20 (2001) or D. A. Walsh et al., *J. Med. Chem.* 32(1) 105-8 (1998).

EXAMPLE 23

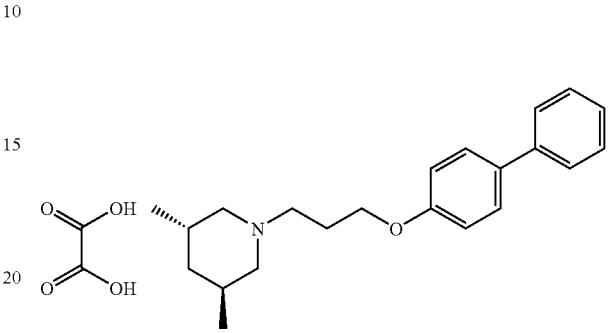

(3S,5S)-1-{3-[(biphenyl-4-yl)oxy]propyl}-3,5-dimethylpiperidine, oxalate

A Following the procedure described in example 1§D, but starting from 1-(3-chloropropoxy)biphenyl (440 mg), (3S, 5S)-3,5-dimethylpiperidine (230 mg), potassium carbonate (800 mg) and a catalytic amount of potassium iodide in N,N-dimethylformamide (10 mL) gives, after salt formation with oxalic acid, 34 mg of (3S,5S)-1-{3-[(biphenyl-4-yl)oxy]propyl}-3,5-dimethylpiperidine, oxalate as a white powder.

$^1$H NMR: oxalate (DMSO)

7.58 (m, 4H, arom), 7.40 (m, 2H, arom), 7.29 (m, 1H, arom), 7.00 (d, J=8.6 Hz, 2H, arom), 4.05 (t, J=5.8 Hz, 2H, CH$_2$O), 3.05 (m, 4H, 2 CH$_2$N), 2.75 (m, 2H, CH$_2$N), 2.08 (m, 4H, CH$_2$, 2 CH), 1.37 (m, 2H, CH$_2$), 0.96 (2d, J=6.8 Hz, J=6.8 Hz, 6H, 2 CH$_3$).

B

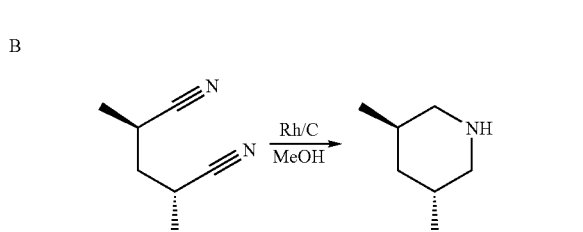

(3S,5S)-3,5-dimethylpiperidine can be obtained as follows:

A suspension of 5% rhodium on alumina (13 g) in a solution of (2S,4S)-2,4-dimethylpentanedinitrile (6.5 g) in 400 mL of methanol is stirred under an atmosphere of dihydrogene for 24 hours at room temperature. The mixture is filtered over a celite pad and the filtrate concentrated under reduced pressure and purified by chromatography over silica gel with a gradient dichloromethane/methanol from 95/5 to 90/10. Fractions containing the expected product are pooled and concentrated under reduced pressure to afford 650 mg of (3S,5S)-3,5-dimethylpiperidine as an orange coloured oil used without any further purification.

C

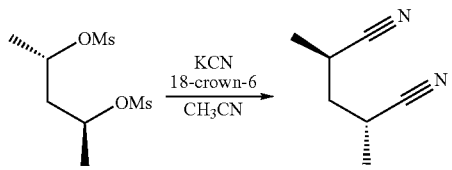

(2S,4S)-2,4-dimethylpentanedinitrile can be obtained as follows:

A suspension of potassium cyanide (36 g) in a solution of (2R,4R)-2,4-pentanediol dimethanesulfonate (36 g) dissolved in acetonitrile (77 mL) is stirred overnight under reflux. The mixture is partitioned between dichloromethane (200 mL) and water (150 mL). The organic layer is extracted six times with dichloromethane. The combined organic extracts are dried over magnesium sulphate, concentrated under reduced pressure and purified by chromatography over silica gel using a gradient heptane/ethyl acetate from 4/1 to 2/1 to give 8.3 g of (2S,4S)-2,4-dimethylpentanedinitrile as a yellow solid used without further purification.

Rf TLC (heptane/ethyl acetate 2/1)=0.5

D

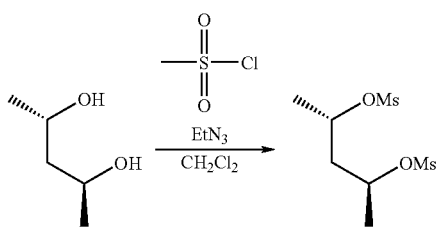

(2R,4R)-2,4-pentanediol dimethanesulfonate can be obtained as follows:

A solution of (2R,4R)-2,4-pentanediol (15.0 g), triethylamine (45.2 mL) and dichloromethane (350 mL) is cooled at a temperature close to 0° C. Methanesulfonyl chloride (24.5 mL) is added dropwise. The mixture is stirred for 3 h at a temperature close to 0° C., hydrolysed with a 1.5 N aqueous hydrochloric solution (100 mL) and extracted with dichloromethane. The organic extracts are pooled, washed with a saturated aqueous solution of sodium hydrogenocarbonate, then a saturated aqueous solution of sodium chloride, dried over magnesium sulphate and concentrated under reduced pressure to give 36.06 g of (2R,4R)-2,4-pentanediol dimethanesulfonate as a brown oil used without further purification.

EXAMPLE 24

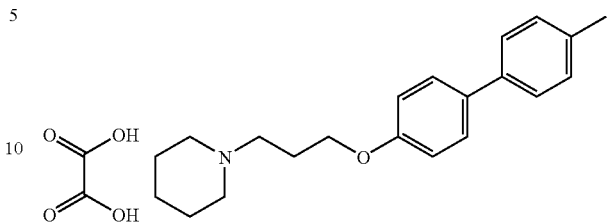

1-{3-[(4'-methylbiphenyl-4-yl)oxy] propyl}piperidine, oxalate

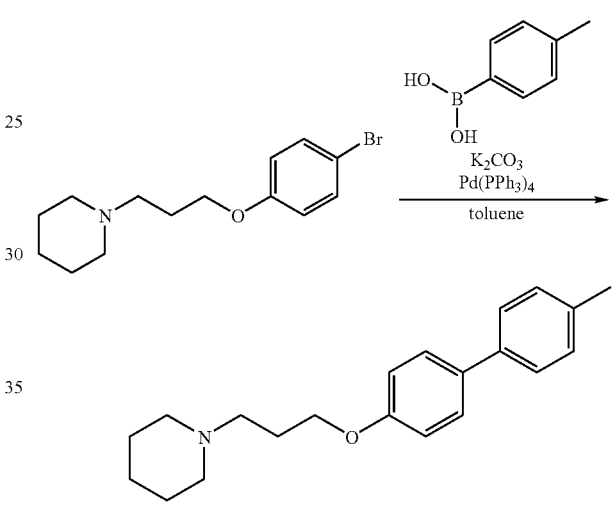

A suspension of potassium carbonate (290 mg) and palladium tetrakistriphenylphosphine (49 mg) in a solution of 1-[3-(4-bromophenoxy)-propyl]piperidine (250 mg) and 4-methylbenzeneboronic acid (228 mg) in toluene (5 mL) is heated overnight at a temperature close to 100° C. The mixture is diluted with ethyl acetate (200 mL) washed with a saturated aqueous sodium bicarbonate solution (3 mL), dried over magnesium sulphate, concentrated under reduced pressure and purified by chromatography over silica gel with dichloromethane then dichloromethane/methanol/ammonia 99/1/0.5. Fractions containing the expected product are pooled, concentrated under reduced pressure and salted with oxalic acid to give 70 mg of 1-{3-[(4'-methylbiphenyl-4-yl) oxy]propyl}piperidine, oxalate as a white solid melting at 195° C.

$^1$H NMR oxalate (DMSO)

7.55 (d, J=8.7 Hz, 2H, arom), 7.47 (d, J=8.0 Hz, 2H, arom), 7.21 (d, J=8.0 Hz, 2H, arom), 6.98 (d, J=8.7 Hz, 2H, arom), 4.02 (t, J=6.0 Hz, 2H, CH$_2$O), 3.1 (m, 6H, 3 CH$_2$N), 2.29 (s, 3H, ArMe), 2.08 (m, 2H, CH$_2$), 1.71 (m, 4H, 2CH$_2$), 1.50 (m, 2H, CH$_2$).

1-[3-(4-bromophenoxy)propyl]piperidine can be prepared as described in EP 9905744

EXAMPLE 25

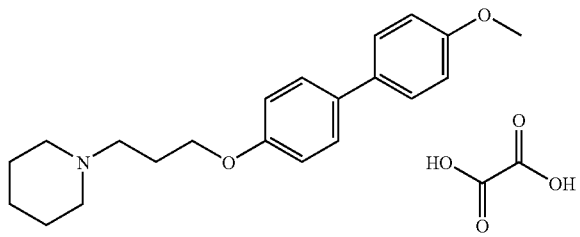

1-{3-[(4'-methoxybiphenyl-4-yl)oxy]
propyl}piperidine, oxalate

Following the procedure described in example 24, but starting from 1-[3-(4-bromophenoxy)propyl]piperidine (250 mg), potassium carbonate (696 mg), 4-methoxybenzeneboronic acid (638 mg) and palladium tetrakistriphenylphosphine (194 mg) in toluene (7 mL) affords, after salt formation with oxalic acid, 174 mg of 1-{3-[(4'-methoxybiphenyl-4-yl)oxy]propyl}piperidine, oxalate as a white solid melting at 188° C.

$^1$H NMR oxalate (DMSO)

7.52 (d, J=8.4 Hz, 4H, arom), 6.96 (d, J=8.4 Hz, 4H, arom), 4.04 (t, J=6.3 Hz, 2H, CH$_2$O), 3.75 (s, 3H, CH3O), 3.15-3.05 (m, 6H, 3 CH$_2$N), 2.10 (m, 2H, CH$_2$), 1.70 (m, 4H, 2CH$_2$), 1.50 (m, 2H, CH$_2$).

EXAMPLE 26

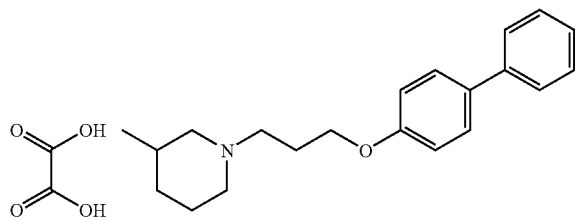

(RS)-1-{3-[(biphenyl-4-yl)oxy]propyl}-3-methylpiperidine, oxalate

Following the procedure described in example 1§D, but starting from 1-(3-chloropropoxy)biphenyl (493 mg), (RS)-3-methylpiperidine (470 µL), potassium carbonate (830 mg) and a catalytic amount of potassium iodide in N,N-dimethylformamide (10 mL) gives, after salt formation with oxalic acid, 478 mg of (RS)-1-{3-[(biphenyl-4-yl)oxy]propyl}-3-methylpiperidine, oxalate as a white solid melting at 173° C.

$^1$H NMR oxalate (DMSO)

7.58 (m, 4H, arom), 7.37 (m, 2H, arom), 7.28 (m, 1H, arom), 6.99 (d, J=8.7 Hz, 2H, arom), 4.05 (t, J=6.0 Hz, 2H, CH$_2$O), 3.35 (m, 2H, 2 CH$_2$N eq.), 3.08 (t, J=7.7 Hz, 2H, CH$_2$N), 2.70 (m, 1H, 1 CH$_2$N ax.), 2.47 (m, 1H, 1 CH$_2$N ax), 2.14 (m, 2H, CH$_2$), 1.81 (m, 4H, CH$_2$, CH, 1 CH$_2$ eq), 1.06 (m, 1H, 1 CH$_2$ ax), 0.87 (d, J=6.6 Hz, 3H, CH$_3$).

EXAMPLE 27

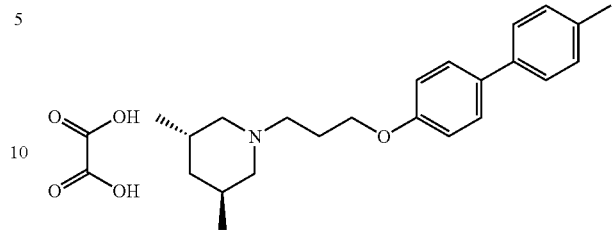

trans-3,5-dimethyl-1-{3-[(4'-methylbiphenyl-4-yl)oxy]propyl}piperidine, oxalate

A Following the procedure described in example 1§D, but starting from 4-(3-chloropropoxy)-4'-methylbiphenyl (274 mg), 3,5-dimethylpiperidine (280 µL of a commercial mixture of cis and trans isomers), potassium carbonate (4.34 mg) and a catalytic amount of potassium iodide in N,N-dimethylformamide (6.5 mL) gives, after two chromatographies over silica gel with diethyl oxide/ligroin/triethylamine 20/80/1 for the first one and ligroin/triethylamine 100/1 then 90/10/1 for the second one, and salt formation with 14.3 mg of oxalic acid in ethanol, 47 mg of trans-3,5-dimethyl-1-{3-[(4'-methylbiphenyl-4-yl)oxy]propyl}-piperidine, oxalate, oxalate as a white solid.

$^1$H NMR oxalate (DMSO)

7.55 (d, J=8.7 Hz, 2H, arom), 7.47 (d, J=8.1 Hz, 2H, arom), 7.20 (d, J=8.1 Hz, 2H, arom), 6.97 (d, J=8.7 Hz, 2H, arom), 4.05 (t, J=6.0 Hz, 2H, CH$_2$O), 3.10-2.6 (m, 6H, 3 CH$_2$N), 2.30 (s, 3H, ArCH$_3$), 2.07 (m, 4H, CH$_2$, 2 CH), 1.36 (m, 2H, CH$_2$), 0.96 (2d, J=6.5 Hz, J=6.5 Hz, 6H, 2CH$_3$).

B 4-(3-chloropropoxy)-4'-methylbiphenyl can be prepared as follows:

Following the procedure described in example 1§E, but starting from 4-hydroxy-4'-methylbiphenyl (194 mg), potassium carbonate (720 mg) and 1-bromo-3-chloropropane (517 µL) in N,N-dimethylformamide (1.5 mL) affords 274 g of 4-(3-chloropropoxy)-4'-methylbiphenyl.

Rf TLC (heptane/ethyl acetate 2/1)=0.82

4-hydroxy-4'-methylbiphenyl can be prepared as described by H. Sakurai et al. J. Org. Chem. 67(8) 2721-2 (2002).

EXAMPLE 28

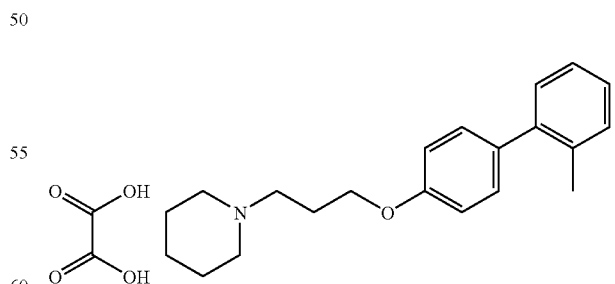

1-{3-[(2'-methylbiphenyl-4-yl)oxy]propyl}piperidine, oxalate

A Following the procedure described in example 1§D, but starting from 4-(3-chloropropoxy)-2'-methylbiphenyl (157 mg), piperidine (100 μL), potassium carbonate (207 mg) and a catalytic amount of potassium iodide in N,N-dimethylformamide (10 mL) gives, after salt formation with oxalic acid, 77 mg of 1-{3-[(2'-methylbiphenyl-4-yl)oxy]propyl}piperidine, oxalate as a white solid melting at 173° C.

¹H NMR oxalate (DMSO)

7.20 (m, 6H, arom), 6.97 (d, J=8.6 Hz, 2H, arom), 4.05 (t, J=6.0 Hz, 2H, CH₂O), 3.11 (m, 6H, 3 CH₂N), 2.19 (s, 3H, ArMe), 2.10 (m, 2H, CH₂), 1.70 (m, 4H, 2CH₂), 1.50 (m, 2H, CH₂).

B 4-(3-chloropropoxy)-2'-methylbiphenyl can be obtained as follows:

Following the procedure described in example 1§E, but starting from 4-hydroxy-2'-methylbiphenyl (0.55 g), potassium carbonate (2.07 g) and 1-bromo-3-chloropropane (1.48 mL) in N,N-dimethylformamide (20 mL) affords 913 mg of 4-(3-chloropropoxy)-2'-methylbiphenyl used without further purification.

Rf TLC (heptane/ethyl acetate 2/1)=0.7

4-hydroxy-2'-methylbiphenyl can be obtained as described by M. P. Capparelli et al. J. Org. Chem. 52(22) 4953-61 (1987) or R. J. Edsall et al. Bioorg. Med. Chem. 11(16) 3457-74 (2003).

EXAMPLE 29

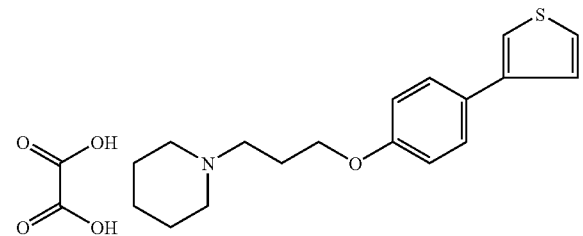

1-{3-[4-(3-thienyl)phenoxy]propyl}piperidine, oxalate

Following the procedure described in example 24, but starting from 1-[3-(4-bromophenoxy)propyl]piperidine (250 mg), potassium carbonate (695 mg), thiophene-3-boronic acid (536 mg) and palladium tetrakistriphenylphosphine (194 mg) in toluene (5 mL) affords, after salt formation with oxalic acid, 161 mg of 1-{3-[4-(3-thienyl)phenoxy]propyl}piperidine, oxalate as a white solid melting at 217° C.

¹H NMR oxalate (DMSO)

7.70 (s, 1H, thiophene), 6.58 (m, 3H, 2 arom, 1 thiophene), 7.47 (d, J=5.0 Hz, 1H, thiophene), 6.94 (d, J=8.6 Hz, 2H, arom), 4.04 (t, J=5.8 Hz, 2H, CH₂O), 3.10 (m, 6H, 3 CH₂N), 2.08 (m, 2H, CH₂), 1.70 (m, 4H, 2CH₂), 1.50 (m, 2H, CH₂).

EXAMPLE 30

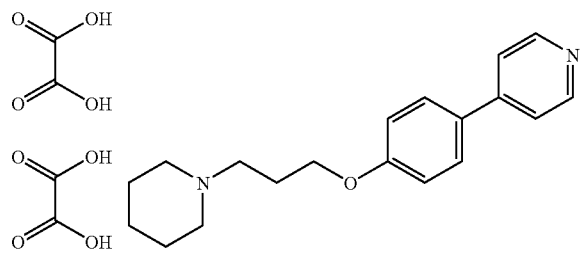

1-{[3-{4-(4-pyridyl)phenoxy]propyl}piperidine, oxalate

Following the procedure described in example 24, but starting from 1-[3-(4-bromophenoxy)propyl]piperidine (364 mg), potassium carbonate (388 mg) in water (4 mL), pyridine-4-boronic acid (300 mg) and palladium tetrakistriphenylphosphine (141 mg) in toluene (8 mL) affords, after salt formation with oxalic acid, 116 mg of 1-{[3-{4-(4-pyridyl)phenoxy]propyl}piperidine, oxalate ¹H NMR oxalate (DMSO)

8.56 (dd, J=4.7 Hz, J=1.4 Hz, 2H, pyridine), 7.76 (d, J=8.7 Hz, 2H, arom), 7.65 (dd, J=4.7 Hz, J=1.4 Hz, 2H, pyridine), 7.06 (d, J=8.7 Hz, 2H, arom), 4.09 (t, J=6 Hz, 2H, CH₂O), 3.5-2.8 (m, 6H, 3 CH₂N), 2.12 (m, 2H, CH₂), 1.80-1.3 (m, 6H, 3CH₂).

EXAMPLE 31

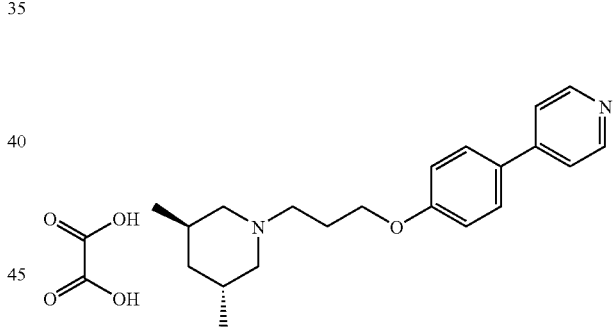

trans-3,5-dimethyl-1-{3-[4-(4-pyridyl)phenoxy]propyl}piperidine, oxalate

A Following the procedure described in example 24, but starting from trans-3,5-dimethyl-1-[3-(4-bromophenoxy)propyl]piperidine (326 mg), potassium carbonate (414 mg) in water (4 mL), pyridine-4-boronic acid (246 mg) and palladium tetrakistriphenylphosphine (116 mg) in toluene (8 mL) affords, after salt formation with oxalic acid, 80 mg of trans-3,5-dimethyl-1-{3-[4-(4-pyridyl)phenoxy]propyl}piperidine, oxalate as a white solid.

¹H NMR oxalate (DMSO)

8.56 (d, J=6.1 Hz, 2H, pyridine), 7.74 (d, J=8.7 Hz, 2H, arom), 7.61 (d, J=6.1 Hz, 2H, pyridine), 7.05 (d, J=8.7 Hz, 2H, arom), 4.10 (t, J=6.1 Hz, 2H, CH₂O), 2.93 (m, 4H, 2 CH₂N), 2.62 (m, 2H, CH₂N), 2.05 (m, 4H, CH₂, 2 CH), 1.35 (dd, J=5.8 Hz, J=5.8 Hz, 2H, CH₂), 0.96 (2d, J=6.9 Hz, J=6.9 Hz, 6H, 2 CH₃).

B trans-3,5-dimethyl-1-[3-(4-bromophenoxy)propyl]piperidine can be prepared as follows:

Following the procedure described in example 1§D, but starting from 1-bromo-4-(3-chloropropoxy)benzene (383 mg), trans-3,5-dimethylpiperidine (663 mg), potassium carbonate (1.06 g) and a catalytic amount of potassium iodide in acetonitrile (10 mL) gives, after chromatography over silica gel using a gradiant dichloromethane/methanol from 0 to 2%, 585 mg of trans-3,5-dimethyl-1-[3-(4-bromophenoxy)propyl]piperidine as a yellow oil used without further purification.

1-bromo-4-(3-chloropropoxy)benzene can be prepared as described by S. Yakabe et al., *Organic Preparations and Procedures International* (1998), 30(2), 218-222.

EXAMPLE 32

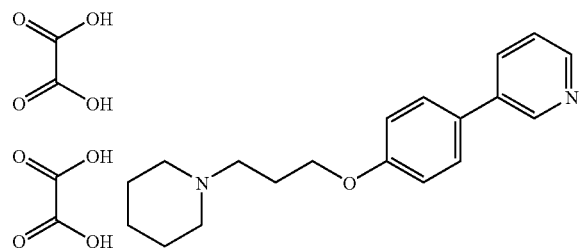

1-{3-[4-(3-pyridyl)phenoxy]propyl}piperidine, oxalate

Following the procedure described in example 24, but starting from 1-[3-(4-bromophenoxy)propyl]piperidine (364 mg), potassium carbonate (388 mg) in water (4 mL), pyridine-3-boronic acid (300 mg) and palladium tetrakistriphenylphosphine (141 mg) in toluene (8 mL) affords, after salt formation with oxalic acid, 75 mg of 1-{[3-{4-(3-pyridyl)phenoxy]propyl}piperidine, oxalate ¹H NMR oxalate (DMSO)
8.83 (d, J=1.8 Hz, 1H, pyridine), 8.49 (dd, J=4.7 Hz, J=1.4 Hz, 1H, pyridine), 7.99 (dt, J=7.9 Hz, J=1.8 Hz, 1H, pyridine), 7.66 (d, J=8.7 Hz, 2H, arom), 7.42 (dd, J=4.7 Hz, J=7.9 Hz, 1H, pyridine), 7.05 (d, J=8.7 Hz, 2H, arom), 4.07 (t, J=5.9 Hz, 2H, CH₂O), 3.11 (m, 6H, 3 CH₂N), 2.10 (m, 2H, CH₂), 1.70 (m, 4H, 2CH₂), 1.50 (m, 2H, CH₂).

EXAMPLE 33

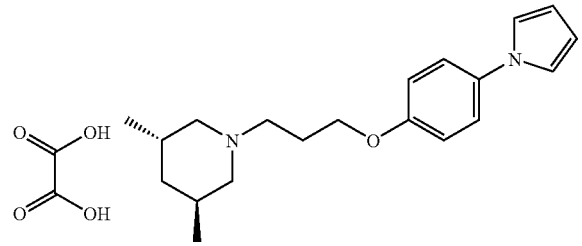

trans-3,5-dimethyl-1-{3-[4-(pyrrol-1-yl)phenoxy]propyl}piperidine, oxalate

A Following the procedure described in example 1§D, but starting from 1-[4-(3-chloropropoxy)phenyl]pyrrole (236 mg), trans-3,5-dimethylpiperidine (190 mg), a catalytic amount of potassium iodide and potassium carbonate (600 mg) in N,N-dimethylformamide (10 mL) gives, after salt formation with oxalic acid, 257 mg of trans-3,5-dimethyl-1-{3-[4-(pyrrol-1-yl)phenoxy]propyl}piperidine, oxalate as a white solid.

¹H NMR oxalate (DMSO)
7.43 (d, J=8.8 Hz, 2H, arom), 7.19 (d, J=2 Hz, 2H, pyrrole), 7.99 (d, J=8.8 Hz, 2H, arom), 6.19 (m, 2H, pyrrole), 4.04 (t, J=6.0 Hz, 2H, CH₂O), 3.00 (m, 4H, 2 CH₂N), 2.71 (m, 2H, CH₂N), 2.06 (m, 4H, CH₂, 2 CH), 1.36 (dd, J=5.6 Hz, J=5.6 Hz, 2H, CH₂), 0.97 (2d, J=7.0 Hz, J=7.0 Hz, 6H, 2 CH₃).

B 1-[4-(3-chloropropoxy)phenyl]pyrrole can be prepared as follows:

Following the procedure described in example 1§E, but starting from 1-(4-hydroxyphenyl)pyrrole (0.8 g), potassium carbonate (3.2 g) and 1-bromo-3-chloropropane (2.5 mL) in N,N-dimethylformamide (10 mL) affords 1.37 g of 1-[4-(3-chloropropoxy)phenyl]pyrrole as a brown solid used without further purification.

EXAMPLE 34

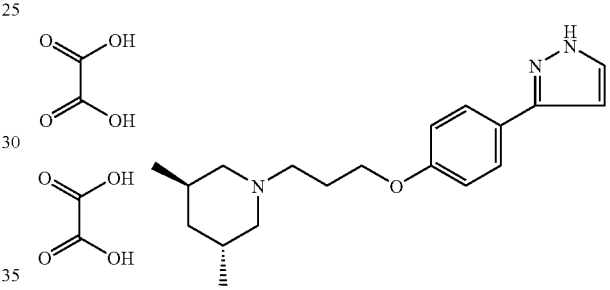

trans-3,5-dimethyl-1-{3-[4-(pyrazol-3-yl)phenoxy]propyl}piperidine, oxalate

A

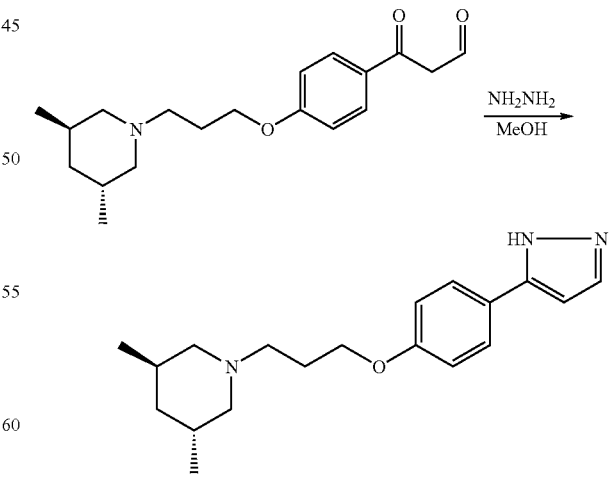

A solution of trans-3,5-dimethyl-1-{3-[4-(3-oxopropanoyl)phenoxy]propyl}-piperidine (200 mg) in a mixture of hydrazine hydrate (50 μL) and methanol (4 mL) is stirred for one hour at room temperature. The mixture is diluted with water and extracted twice with ethyl acetate, dried over magnesium sulphate, concentrated under reduced pressure and purified by chromatography over silica gel. Fractions containing the expected product are pooled, concentrated under reduced pressure and salted with oxalic acid to afford 142 mg of trans-3,5-dimethyl-1-{3-[4-(pyrazol-3-yl)phenoxy]propyl}piperidine, oxalate as a pale yellow solid.

$^1$H NMR oxalate (DMSO)

7.67 (m, 3H, 2 arom, 1 pyrrazole), 6.95 (m, 2H, arom), 6.54 (m, 1H, pyrrazole), 4.06 (m, 2H, CH$_2$O), 3.07 (m, 4H, 2 CH$_2$N), 2.78 (m, 2H, CH$_2$N), 2.09 (m, 4H, CH$_2$, 2 CH), 1.39 (m, 2H, CH$_2$), 0.98 (m, 6H, 2 CH$_3$).

B

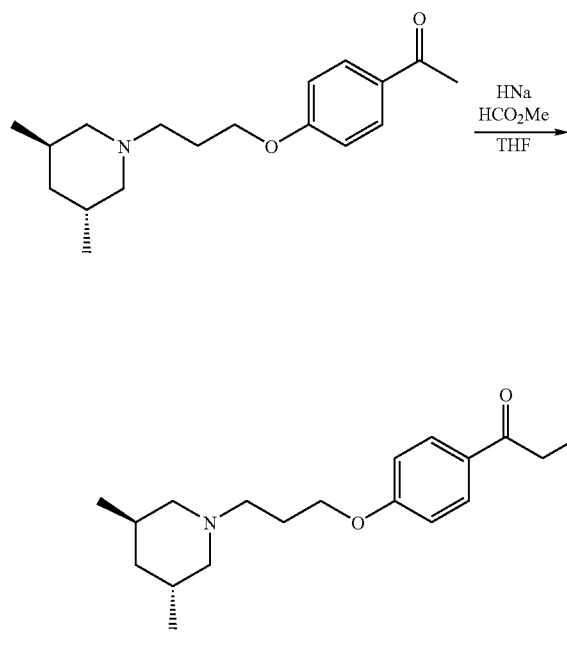

trans-3,5-dimethyl-1-{3-[4-(3-oxopropanoyl)phenoxy]propyl}piperidine can be prepared as follows:

To a suspension of sodium hydride (82 mg, 60% in paraffin) are added methyl formate (150 µL) and a solution of trans-3,5-dimethyl-1-[3-(4-acetylphenoxy)propyl]piperidine (610 mg) in tetrahydrofuran (0.4 mL). The mixture is stirred for two hours at room temperature then hydrolysed with a 1N aqueous hydrochloric acid solution keeping the pH alkaline. The solution is extracted twice with ethyl acetate. The extracts are pooled, dried over magnesium sulphate, concentrated under reduced pressure and purified by chromatography over silica gel with a gradient dichloromethane/methanol from 100/0 to 95/5. Fractions containing the expected product are pooled, concentrated under reduced pressure to give 100 mg of trans-3,5-dimethyl-1-{3-[4-(3-oxopropanoyl)phenoxy]propyl}piperidine as a pale yellow oil that is used rapidly, without further purification in the next step.

Rf TLC (dichloromethane/methanol 90/10)=0.52 trans-3,5-dimethyl-1-[3-(4-acetylphenoxy)propyl]piperidine can be prepared as described in EP9905744

EXAMPLE 35

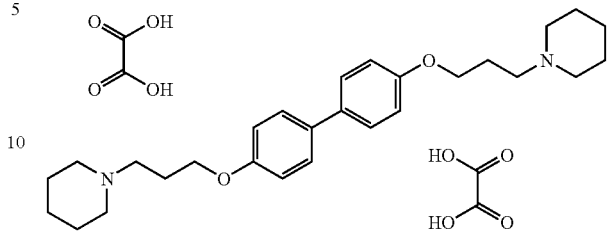

di-1,1'-{(biphenyl-4,4'-diyl)bis[oxy(propan-1,3-diyl)]}piperidine, dioxalate

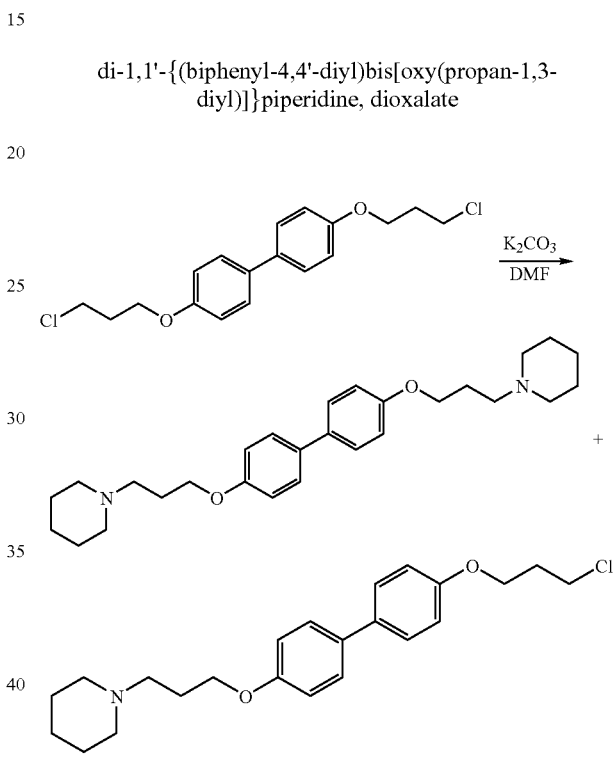

A suspension of potassium carbonate (0.8 g) in a mixture of 4,4'-bis-(3-chloropropoxy)phenyl (0.65 g), piperidine (0.33 g) and N,N-dimethylformamide (5 mL) is stirred for six days at room temperature. The mixture is filtered, concentrated under reduced pressure and purified by chromatography over silica gel with a gradient dichloromethane/methanol from 100/0 to 95/5. Fractions containing the monoaminated product are pooled and concentrated to give 0.2 g of 1-{3-[4'-(3-chloropropoxy)biphen-4-yloxy]propyl}piperidine. Fractions containing the diaminated product are pooled and concentrated to give 0.11 g of di-1,1'-{(biphenyl-4,4'-diyl)bis[oxy(propan-1,3-diyl)]}piperidine as a white solid which is salted with 46 mg of oxalic acid in ethanol to yield 0.11 g of di-1,1'-{(biphenyl-4,4'-diyl)bis[oxy(propan-1,3-diyl)]}piperidine, dioxalate as a white solid.

$^1$H NMR oxalate (DMSO)

7.50 (d, J=8.6 Hz, 4H, arom), 6.96 (d, J=8.6 Hz, 4H, arom), 4.02 (t, J=6 Hz, 4H, CH$_2$O), 2.78 (m, 12H, CH$_2$N), 1.98 (m, 4H, CH$_2$), 1.59 (m, 8H, 4CH$_2$), 1.44 (m, 4H, 2CH$_2$).

4,4'-bis-(3-chloropropoxy)phenyl can be prepared according to the method described in GB1129175 (Feb. 10, 1968).

EXAMPLE 36

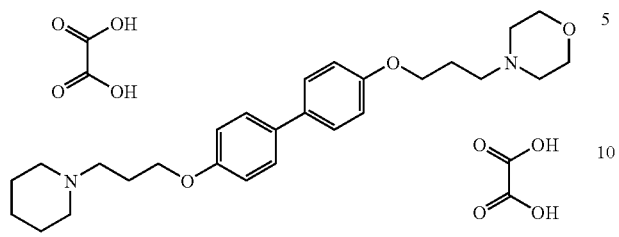

4-(3-{[4'-(3-piperidinopropoxy)biphenyl-4-yl]oxy}propyl)morpholine, dioxalate

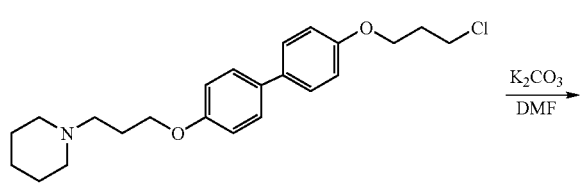

A suspension of potassium carbonate (138 mg) in a mixture of 1-{3-[4'-(3-chloropropoxy)biphenyl-4-yloxy]propyl}piperidine (100 mg), morpholine (65 mg) and N,N-dimethylformamide (1 mL) is stirred for four days at room temperature. The mixture is filtered, concentrated under reduced pressure and purified by chromatography over silica gel with dichloromethane/methanol 82/2 as eluent. Fractions containing the expected product are pooled and concentrated under reduced pressure to give 25 mg of 4-(3-{[4'-(3-piperidinopropoxy)biphenyl-4-yl]oxy}propyl)morpholine as a off white solid which is salted with 9.4 mg of oxalic acid yielding 15 mg of 4-(3-{[4'-(3-piperidinopropoxy)biphenyl-4-yl]oxy}propyl)-morpholine, dioxalate as a white solid.

$^1$H NMR oxalate (DMSO)

7.51 (m, 4H, arom), 6.97 (m, 4H, arom), 4.03 (m, 4H, CH$_2$O), 3.65 (m, 4H, 2 CH$_2$O), 3.50-2.6 (m, 12H, 6 CH$_2$N), 2.10 (m, 2H, CH$_2$), 1.98 (m, 2H, CH$_2$), 1.90-1.30 (m, 6H, 3CH$_2$).

EXAMPLE 37

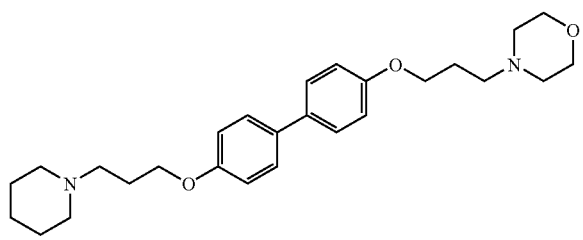

1-(3-{[4'-(3-piperidinopropoxy)biphenyl-4-yl]oxy}propyl)pyrrolidine

Following the procedure described in example 36, but starting from 1-{3-[4'-(3-chloropropoxy)biphenyl-4-yloxy]propyl}piperidine (250 mg), pyrrolidine (138 mg) and potassium carbonate (360 mg) in N,N-dimethylformamide (2 mL) affords 90 mg of 1-(3-{[4'-(3-piperidinopropoxy)biphenyl-4-yl]oxy}propyl)pyrrolidine as white crystals melting at 105-108° C.

$^1$H NMR base (CDCl$_3$)

7.46 (2 d, J=8.5 Hz, J=8.5 Hz, 4H, arom), 6.95 (2 d, J=8.5 Hz, J=8.5 Hz, 4H, arom), 4.07 (t, J=6.2 Hz, 2H, CH$_2$O), 4.05 (t, J=6.2 Hz, 2H, CH$_2$O), 2.80-2.40 (m, 12H, CH$_2$N), 2.08 (m, 4H, 2CH$_2$), 1.85 (m, 4H, 2 CH$_{2\ pyrrolidine}$), 1.63 (m, 4H, 2 CH$_{2\ piperidine}$), 1.47 (m, 2H, 1 CH$_{2\ piperidine}$).

EXAMPLE 38 di-1,1'-{(biphenyl-4,4'-diyl)bis[oxy(propan-1,3-diyl)]}pyrrolidine

Following the procedure described in example 35, but starting from 4,4'-bis-(3-chloropropoxy)phenyl (7.73 g), potassium carbonate (9.1 g), a catalytic amount of potassium iodide in a mixture of pyrrolidine (2.21 mL) and (100 mL) N,N-dimethylformamide affords 3.73 g of 1-{3-[4'-(3-chloropropoxy)biphenyl-4-yloxy]propyl}pyrrolidine and 209 mg of di-1,1'-{(biphenyl-4,4'-diyl)bis[oxy(propan-1,3-diyl)]}pyrrolidine.

Rf TLC (dichloromethane/methanol/ammonia 90/10/1)= 0.18 for di-1,1'-{(biphenyl-4,4'-diyl)bis[oxy(propan-1,3-diyl)]}pyrrolidine and 0.46 for 1-{3-[4'-(3-chloropropoxy)biphenyl-4-yloxy]propyl}pyrrolidine $^1$H NMR base (CDCl$_3$)

7.46 (d, J=8.7 Hz, 4H, arom), 6.95 (d, J=8.7 Hz, 4H, arom), 4.07 (t, J=6.4 Hz, 4H, CH$_2$O), 2.65 (m, 12H, 6 CH$_2$N), 2.01 (m, 4H, CH$_2$), 1.83 (m, 8H, 4CH$_2$).

EXAMPLE 39

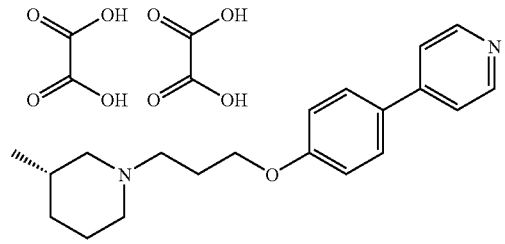

(3S)-3-methyl-1-{3-[4-(4-pyridyl)phenoxy]
propyl}piperidine, dioxalate

A Following the procedure described in example 24, but starting from (3S)-1-[3-(4-bromophenoxy)propyl]-3-methylpiperidine (118 mg), potassium carbonate (156 mg), 4-pyridylboronic acid (56 mg) and palladium tetrakistriphenylphosphine (22 mg) in toluene (4 mL) affords, after salt formation with oxalic acid, 50 mg of (3S)-3-methyl-1-{3-[4-(4-pyridyl)phenoxy]propyl}piperidine, dioxalate as a white solid melting at 88° C.

$^1$H NMR oxalate (DMSO)

8.56 (d, J=6.1 Hz, 2H, pyridine), 7.76 (d, J=8.7 Hz, 2H, arom), 7.65 (d, J=6.1 Hz, 2H, pyridine), 7.05 (d, J=8.7 Hz, 2H, arom), 4.09 (t, J=5.9 Hz, 2H, CH$_2$O), 3.39 (m, 2H, CH$_2$N), 3.16 (m, 2H, CH$_2$N), 2.77 (m, 1H, CH$_2$N), 2.52 (m, 1H, CH$_2$N), 2.14 (m, 2H, CH$_2$), 1.84 (m, 4H, 2CH$_2$), 1.08 (m, 1H, CH), 0.88 (d, 3H, CH$_3$).

B (3S)-1-[3-(4-bromophenoxy)propyl]-3-methylpiperidine can be prepared as follows.

Following the procedure described in example 1§D, but starting from 4-bromo-1-(3-chloropropoxy)benzene (125 mg), (S)-3-methylpiperidine, mandelate (101 mg), potassium carbonate (207 mg) and potassium iodide (10 mg) in acetonitrile (5 mL) gives, after salt purification by chromatography over silica gel with a gradient dichloromethane/methanol from 100/0 to 95/5, 118 mg of (3S)-1-[3-(4-bromophenoxy)propyl]-3-methylpiperidine as a white powder.

(S)-3-methylpiperidine, mandelate can be prepared as described by E. Coderc, P. Cerruti, J. Vignon, J. F. Rouayrenc, J. M. Kamenka, *Eur. J. Med. Chem.* 30, 463-470 (1995)

4-bromo-1-(3-chloropropoxy)benzene can be prepared as described by S. Yakabe, M. Hirano, T. Morimoto, *Org. Prep. Proc. Int.* 30(2) 218-222 (1998).

EXAMPLE 40

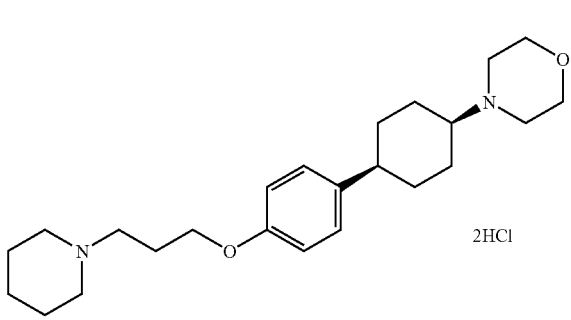

EXAMPLE 41

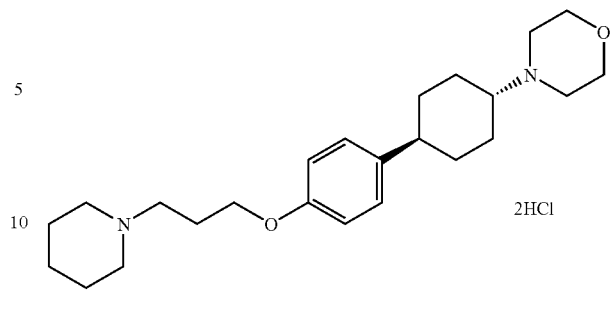

1-{3-[4-(cis-4-morpholinocyclohex-1-yl)phenoxy]
propyl}piperidine, dihydrochloride and 1-{3-[4-
(trans-4-morpholinocyclohex-1-yl)phenoxy]-
propyl}piperidine, dihydro-chloride Following the procedure described in example 18§A, but starting from 1-{3-[4-(4-oxocyclohexyl)phenoxy]propyl}piperidine (5 g), morpholine (2.76 mL), acetic acid (1.18 mL) and sodium triacetoxyborohydride (5.56 g) in tetrahydrofuran (80 mL), the following products are obtained in order of elution, after salt formation with a solution of hydrogen chloride in diethyl oxide, 2.75 g of 1-{3-[4-(4-morpholinocyclohex-1-yl)phenoxy]propyl}piperidine, dihydrochloride (isomer A) melting at 297-298° C. and 1.2 g of 1-{3-[4-(trans-4-morpholinocyclohex-1-yl)phenoxy] propyl}piperidine, dihydrochloride (isomer B) melting at 296-297° C.

1H NMR: dihydrochloride (DMSO)

Isomer A:

7.32 (d, J=8.6 Hz, 2H, arom), 6.84 (d, J=8.6 Hz, 2H, arom), 3.98 (m, 6H, 3 CH$_2$O), 3.47 (m, 4H), 2.70-3.30 (m, 8H), 2.15-1.4 (m, 16H).

Isomer B:

7.12 (d, J=8.5 Hz, 2H, arom), 6.83 (d, J=8.5 Hz, 2H, arom), 3.96 (m, 6H, 3 CH$_2$O), 3.38 (m, 4H), 3.09 (m, 5H), 2.79 (m, 2H), CHN, 2.43 (m, 1H), 2.15-1.3 (m, 16H).

EXAMPLE 41

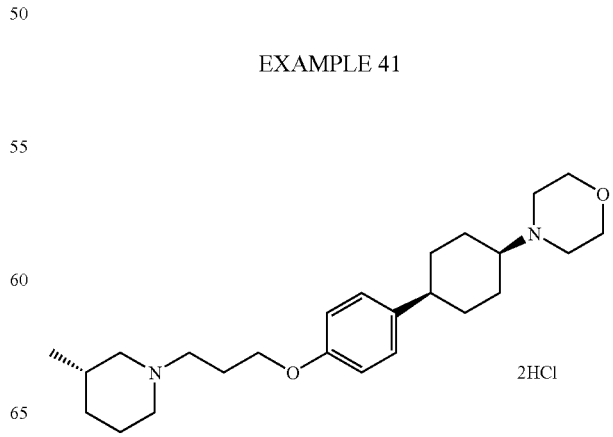

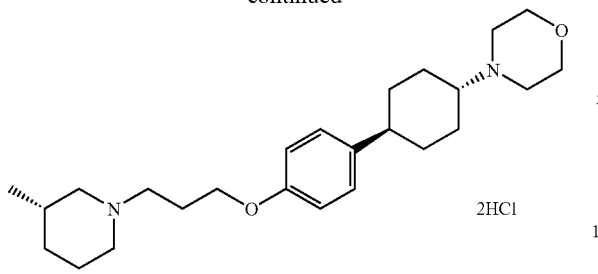

(3S)-3-methyl-1-{3-[4-(cis-4-morpholinocyclohex-1-yl)phenoxy]propyl}piperidine, dihydrochloride and (3S)-3-methyl-1-{3-[4-(trans-4-morpholinocyclohex-1-yl)phenoxy]propyl}piperidine, dihydrochloride A Following the procedure described in example 47§A, but starting from (3S)-3-methyl-1-{3-[4-(4-oxocyclohexyl)phenoxy]propyl}piperidine (5.16 g), morpholine (2.77 mL), acetic acid (1.17 mL) and sodium triacetoxyborohydride (5.6 g) in tetrahydrofuran (78 mL), the following products are obtained in order of elution, after salt formation with a solution of hydrogen chloride in diethyl oxide, 2.0 g of (3S)-3-methyl-1-{3-[4-(4-morpholinocyclohex-1-yl)phenoxy]propyl}-piperidine, dihydrochloride (isomer A) melting at 275-276° C. and 1 g of (3S)-3-methyl-1-{3-[4-(4-morpholinocyclohex-1-yl)phenoxy]propyl}piperidine, dihydrochloride (isomer B) melting at 280° C.

1H NMR: hydrochloride (D2O)

Isomer A 7.35 (d, J=8.6 Hz, 2H, arom), 6.84 (d, J=8.6 Hz, 2H, arom), 4.11 (t, J=5.7 Hz, 2H, CH₂O), 4.10-3.80 (m, 4H, 2 CH₂O), 3.65-3.05 (m, 10H), 2.94 (m, 1H), 2.82 (m, 1H,), 2.50 (m, 1H), 2.19 (m, 4H), 1.84 (m, 9H), 1.15 (m, 1H), 0.93 (d, J=6.4 Hz, 3H, CH₃).

Isomer B 7.24 (d, J=8.6 Hz, 2H, arom), 6.95 (d, J=8.6 Hz, 2H, arom), 4.10 (t, J=5.6 Hz, 2H, CH₂O), 4.10-3.70 (m, 4H, 2 CH₂O), 3.65-3.05 (m, 9H), 2.82 (m, 1H), 2.55 (m, 2H), 2.19 (m, 4H), 2.05-1.45 (m, 10H), 1.14 (m, 1H), 0.92 (d, J=6.4 Hz, 3H, CH₃).

B (3S)-3-methyl-1-{3-[4-(4-oxocyclohexyl)phenoxy]propyl}piperidine can be prepared as follows:

Following the procedure described in example 47§C, but starting from potassium carbonate (10.52 g), 4-[4-(3-chloropropoxy)phenyl]cyclohexanone (7 g), (3S)-3-methylpiperidine mandelate (8.31 g), a catalytic amount of potassium iodide and N,N-dimethylformamide (105 mL), affords 5.12 g of (3S)-3-methyl-1-{3-[4-(4-oxocyclohexyl)phenoxy]propyl}piperidine as an orange oil used without further purification.

EXAMPLE 42

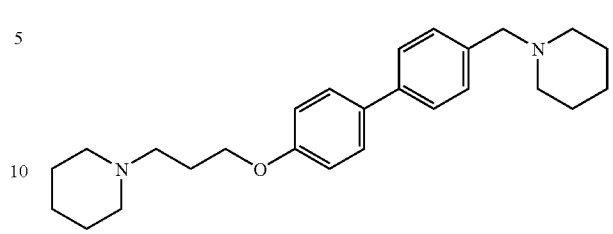

1-(3-{[4'-(piperidinomethyl)biphenyl-4-yl]oxy}propyl)piperidine

A

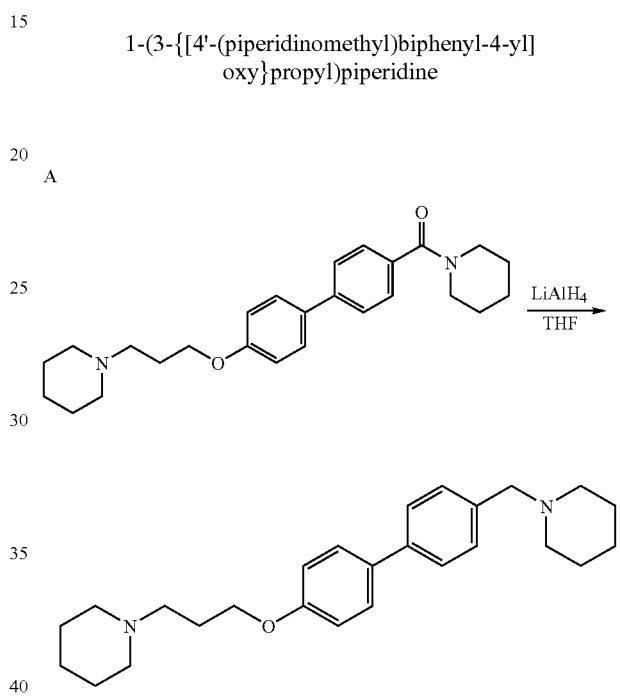

To a solution of 1-(3-{[4'-(piperidinocarbonyl)biphenyl-4-yl]oxy}propyl)-piperidine (500 mg) in tetrahydrofuran (20 mL) is added lithium aluminium hydride (105 mg). The suspension is stirred at room temperature for three hours, then hydrolysed through the successive addition of water (110 μL), 15% aqueous solution of sodium hydroxide (110 μL) and water (330 μL). The mixture is stirred for an half hour and filtrated. The filtrate is dried over magnesium sulfate and concentrated under reduced pressure. The product thus obtained is recrystallized in diisopropyl oxide and purified by chromatography over silica gel with a gradient dichloromethane/methanol from 98/2 to 85/15. Fraction containing the expected product are pooled, concentrated under reduced pressure to give 125 mg of 1-(3-{[4'-(piperidinomethyl)biphenyl-4-yl]oxy}propyl)piperidine as white crystals melting at 90° C.

1H NMR: base (CDCl3)

7.52 (d, J=8.5 Hz, 2H, arom), 7.50 (d, J=7.9 Hz, 2H, arom), 7.36 (d, J=7.9 Hz, 2H, arom), 6.97 (d, J=8.5 Hz, 2H, arom), 4.05 (t, J=6.3 Hz, 2H, CH₂O), 3.5 (s, 2H, CH₂Ar), 2.49 (m, 10H, 5 CH₂N), 2.00 (m, 2H, CH₂) 1.60 (m, 8H, 4CH₂) 1.45 (m, 4H, 2 CH₂).

B

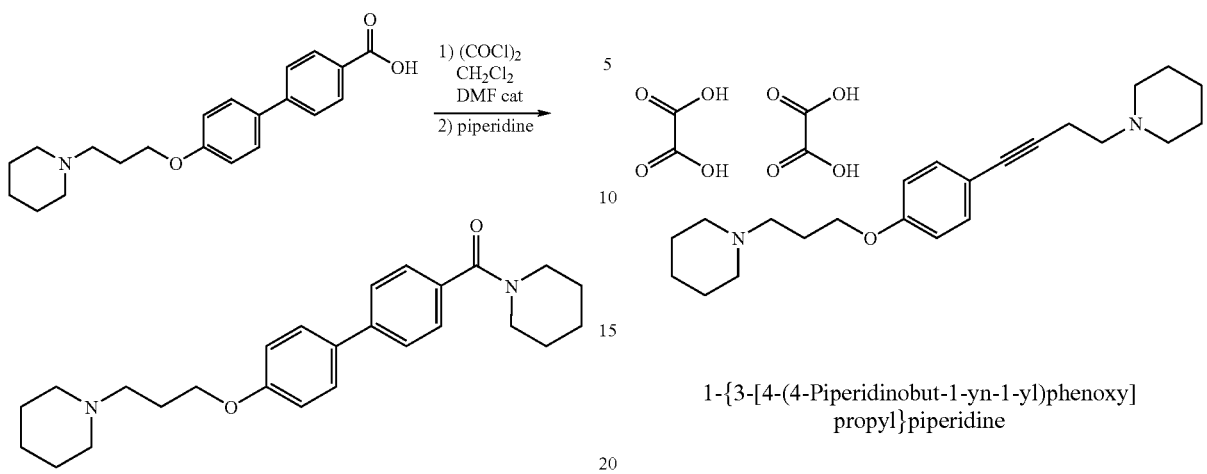

1-(3-{[4'-(piperidinocarbonyl)biphenyl-4-yl]oxy}propyl) piperidine can be prepared as follows:

To a solution of 4'-(3-piperidinopropoxy)biphenyl-1-carboxylic acid (0.9 g) in dichloromethane (10 mL) containing one drop of N,N-dimethylformamide is added oxalyl chloride (285 μL). The suspension is stirred for one hour at room temperature, then chloroform (20 mL) and a drop of N,N-dimethylformamide are added. and the mixture is stirred for three hours at room temperature. Piperidine (1.6 mL) is then added and the mixture is stirred for an half hour at room temperature, washed with water, dried over magnesium sulfate and concentrated under reduced pressure. The product thus obtained is purified by chromatography over silica gel with a gradient dichloromethane/methanol from 100/0 to 90/10. Fraction containing the expected product are pooled, concentrated under reduced pressure to give 620 mg of 1-(3-{[4'-(piperidinocarbonyl)biphenyl-4-yl]oxy}propyl)-piperidine as white crystals melting at 122° C.

C 4'-(3-piperidinopropoxy)biphenyl-1-carboxylic acid can be prepared as follows:

Following the procedure described in example 1§C, but starting from 1-(3-{[4'-(ethoxycarbonyl)biphenyl-4-yl]oxy}propyl)piperidine (2.65 g) and a normal aqueous solution of sodium hydroxide (8 mL) in ethanol (20 mL) affords 4'-(3-piperidinopropoxy)biphenyl-1-carboxylic acid in quantitative yield.

D 1-(3-{[4'-(ethoxycarbonyl)biphenyl-4-yl]oxy}propyl) piperidine can be prepared as follows:

Following the procedure described in example 1§D, but starting from 4'-(3-chloropropoxy)biphenyl-1-carboxylic acid ethyl ester (8.26 mmol), potassium carbonate (2.3 g) and piperidine (1.1 g) in N,N-dimethylformamide (20 mL) affords 1-(3-{[4'-(ethoxycarbonyl)biphenyl-4-yl]oxy}propyl)piperidine (2.65 g) as white crystals.

E 4'-(3-chloropropoxy)biphenyl-1-carboxylic acid ethyl ester can be prepared as follows:

Following the procedure described in example 47§D, but starting from 4'-hydroxybiphenyl-1-carboxylic acid ethyl ester (3 g), potassium carbonate (8.55 g) and 1-bromo-3-chloropropanol (6 mL) in N,N-dimethylformamide (30 mL) affords 4'-(3-chloropropoxy)biphenyl-1-carboxylic acid ethyl ester in quantitative yield used without further purification.

EXAMPLE 43

1-{3-[4-(4-Piperidinobut-1-yn-1-yl)phenoxy] propyl}piperidine

A

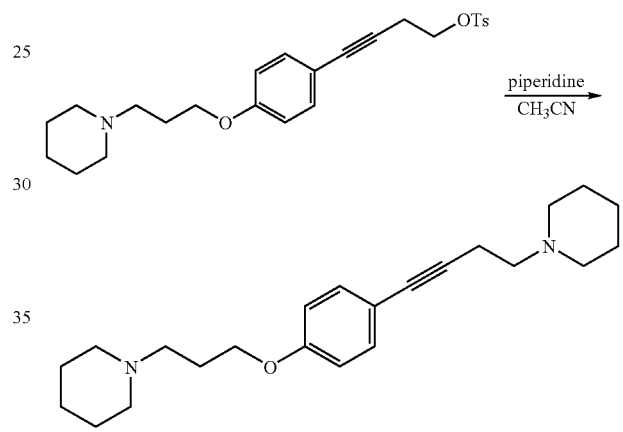

A suspension of potassium carbonate (760 mg) in a solution of 1-{3-[4-(4-tosyloxybut-1-yn-1-yl)phenoxy] propyl}piperidine (487 mg) in a mixture of piperidine (1.09 mL) and acetonitrile (8 mL) is heated at a temperature close to 60° C. for 24 h. The suspension is filtrated. The filtrate concentrated under reduced pressure and purified by chromatography over silica gel using a gradient dichloromethane/methanol from 100/0 to 95/5. Fraction containing the expected product are pooled, concentrated under reduced pressure and salted with oxalic acid to give 190 mg of 1-{3-[4-(4-piperidinobut-1-yn-1-yl)phenoxy]propyl}piperidine as an off white solid melting at 167° C.

1H NMR: oxalate (DMSO) 7.32 (d, J=8.6 Hz, 2H, arom), 6.89 (d, J=8.6 Hz, 2H, arom), 4.01 (t, J=5.8 Hz, 2H, $CH_2O$), 3.09 (m, 12H, 6 $CH_2N$), 2.81 (t, J=7.5 Hz, 2H, $CH_2C$), 2.07 (m, 2H, $CH_2$), 1.69 (m, 8H, $4CH_2$), 1.49 (m, 4H, $2CH_2$).

B

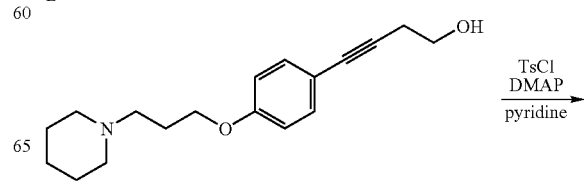

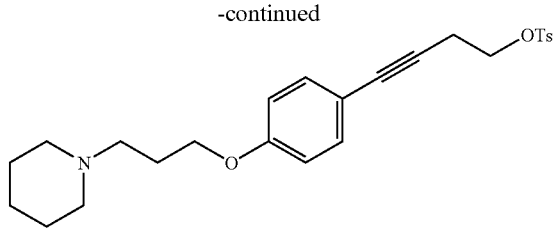

1-{3-[4-(4-tosyloxybut-1-yn-1-yl)phenoxy]propyl}piperidine can be prepared as follows:

To a solution of 1-{3-[4-(4-hydroxybut-1-yn-1-yl)phenoxy]propyl}piperidine (393 mg) in acetonitrile (10 mL) are added successively triethylamine (0.446 mL), 4-dimethylaminopyridine (18 mg) and tosyl chloride (617 mg). The mixture is stirred overnight at room temperature, concentrated under reduced pressure and purified by chromatography over silica gel to give 495 g of 1-{3-[4-(4-tosyloxybut-1-yn-1-yl)phenoxy]propyl}piperidine.

C

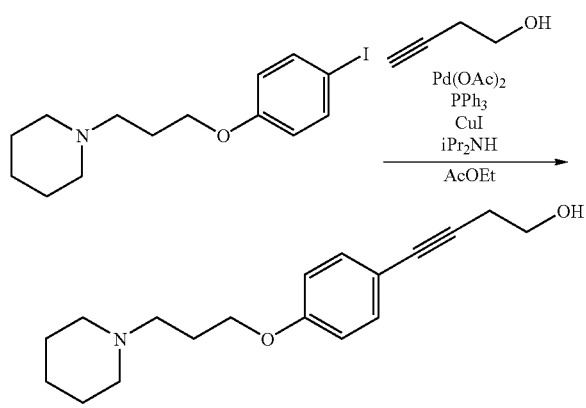

1-{3-[4-(4-hydroxybut-1-yn-1-yl)phenoxy]propyl}piperidine can be prepared as follows:

To a solution of 1-[3-(4-iodophenoxy)propyl]piperidine (0.72 g) in ethyl acetate (10 mL) cooled at a temperature close to 5° C., are added successively palladium acetate (4.5 mg), triphenylphosphine (10.5 mg), cuprous iodide (7.6 mg), 3-butyn-1-ol (203 µL) and diisopropylamine (560 µL). The mixture is stirred at a temperature close to 15° C. for one hour, then at a temperature close to 50° C. for five hours. The mixture is cooled at room temperature, filtered over a celite pad and the filtrate concentrated under reduced pressure. Purification by chromatography over silica gel using a gradient dichloromethane/methanol 100/to 95/5 fives 444 mg of 1-{3-[4-(4-hydroxybut-1-yn-1-yl)phenoxy]propyl}piperidine melting at 56° C.

D 1-[3-(4-iodophenoxy)propyl]piperidine can be prepared as follows:

Following the procedure described in example 1§E, but starting from 1-(3-chloropropoxy)-4-iodobenzene (3 g), potassium carbonate (4.15 g) and piperidine (1.7 g) in N,N-dimethylformamide (30 mL) affords 3.49 g of 1-[3-(4-iodophenoxy)propyl]piperidine used without further purification.

1-(3-chloropropoxy)-4-iodobenzene can be prepared as described in DE19958246.

EXAMPLE 44

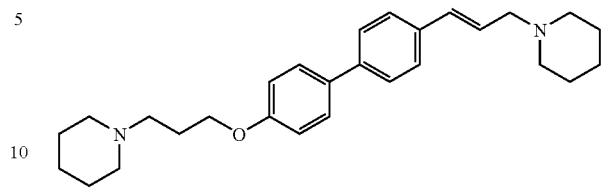

(E)-1-(3-{[4'-(3-piperidinoprop-1-en-1-yl)biphenyl-4-yl]oxy}propyl)piperidine

A Following the procedure of example 42§A, but starting from 1-(3-{[4'-(2-piperidinocarbonylethen-1-yl)biphenyl-4-yl]oxy}propyl)piperidine (0.6 g) and lithium aluminum hydride (120 mg) in tetrahydrofuran (15 mL) affords 15 mg of 1-(3-{[4'-(3-piperidinoprop-1-en-1-yl)biphenyl-4-yl]oxy}propyl)piperidine as pale yellow crystals melting at 100-105° C.

1H NMR: Base (CDCl3)

7.49 (m, 6H, arom), 6.97 (d, J=8.7 Hz, 2H, arom), 6.53 (d, J=15.8 Hz, 1H, ArCH=), 6.33 (dt, J=15.8 Hz, J=6.4 Hz, 1H, CH=), 4.05 (t, J=6.3 Hz, 2H, CH$_2$O), 3.14 (d, J=6.4 Hz, 2H, =CH$_2$N), 2.47 (m, 10H, 5 CH$_2$N), 2.00 (m, 2H, CH$_2$), 1.61 (m, 8H, 4CH$_2$), 1.46 (m, 4H, 2CH$_2$).

B 1-(3-{[4'-(2-piperidinocarbonylethen-1-yl)biphenyl-4-yl]oxy}propyl)piperidine can be prepared as follows A solution of 3-[4'-(3-piperidinopropoxy)biphenyl-4-yl]acrylic acid (1 g) in sulfonyl chloride (5 mL) is stirred at a temperature close to 40° C. for two hours, then concentrated under reduced pressure. The concentrate is dissolved in dichloromethane (10 mL) and piperidine (4 mL) is added dropwise. The mixture is stirred at room temperature for one hour, washed with water, then a normal aqueous solution of hydrochloric acid, dried over magnesium sulfate, concentrated and purified by chromatography over silica gel using a gradient dichloromethane/methanol from 100/0 to 95/5. Fractions containing the expected product are pooled and concentrated under reduced pressure to afford 840 mg of 1-(3-{[4'-(2-piperidinocarbonylethen-1-yl)biphenyl-4-yl]oxy}propyl)piperidine as beige crystals melting at 146-150° C.

C 3-[4'-(3-piperidinopropoxy)biphenyl-4-yl]acrylic acid can be prepared as follows:

Following the procedure described in example 1§C, but starting from 1-(3-{[4'-(2-ethoxycarbonylethen-1-yl)biphenyl-4-yl]oxy}propyl)piperidine (2.4 g) and a normal aqueous solution of sodium hydroxide (10 mL) in ethanol (10 mL) affords 3-[4'-(3-piperidinopropoxy)biphenyl-4-yl]acrylic acid used without further purification in the next step.

D

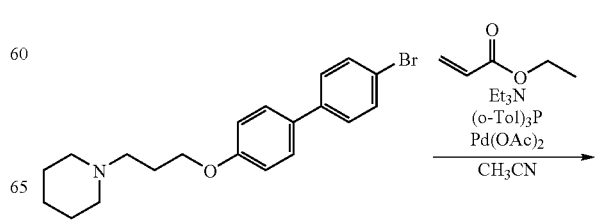

-continued

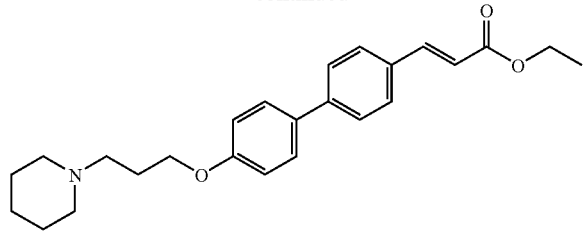

1-(3-{[4'-(2-ethoxycarbonylethen-1-yl)biphenyl-4-yl]oxy}propyl)piperidine can be prepared as follows:

A degazed solution of 1-{3-[(4'-bromobiphenyl-4-yl)oxy]propyl}piperidine (2.8 g), triethylamine (2.8 mL), tri(o-tolyl)phosphine (365 mg), palladium acetate (170 mg) and ethyl acrylate (2.9 mL) in acetonitrile (5 mL) is stirred at a temperature close to 60° C. for one hour, then at room temperature overnight and finally 6 h at a temperature close to 90° C. The solution is concentrated under reduced pressure, redissolved in dichloromethane, filtered and chromatographied over silica gel to give 1.3 g of 1-(3-{[4'-(2-ethoxycarbonylethen-1-yl)biphenyl-4-yl]oxy}propyl)piperidine.

E

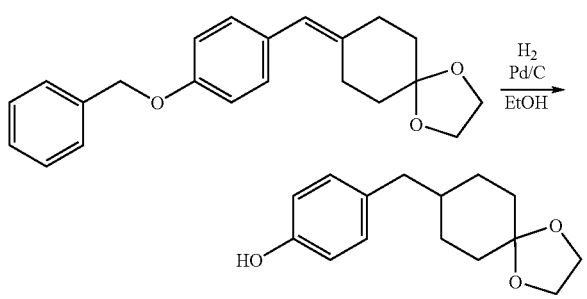

1-{3-[(4'-bromobiphenyl-4-yl)oxy]propyl}piperidine can be prepared as follows: Following the procedure described in example 47§C, but starting from 4'-bromo-4-(3-chloropropoxy)biphenyl (3.25 g), piperidine (0.85 g) and potassium carbonate (2.8 g) in acetonitrile (100 mL) gives 2.8 g of 1-{3-[(4'-bromobiphenyl-4-yl)oxy]propyl}piperidine.

F 4'-bromo-4-(3-chloropropoxy)biphenyl can be prepared as follows:

Following the procedure described in example 1§E, but starting from 4-bromo-4'-hydroxybiphenyl (5 g), potassium carbonate (13.8 g) and 1-bromo-3-chloropropane (15.7 g) in acetonitrile (100 mL) affords 6.4 g of 4'-bromo-4-(3-chloropropoxy)biphenyl as white crystals.

Rf TLC (heptane/ethyl acetate 2/1)=0.6

EXAMPLE 45

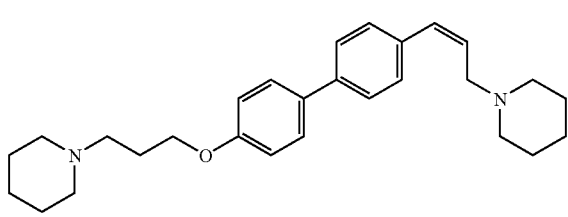

(Z)-1-(3-{[4'-(3-piperidinoprop-1-en-1-yl)biphenyl-4-yl]oxy}propyl)piperidine

A

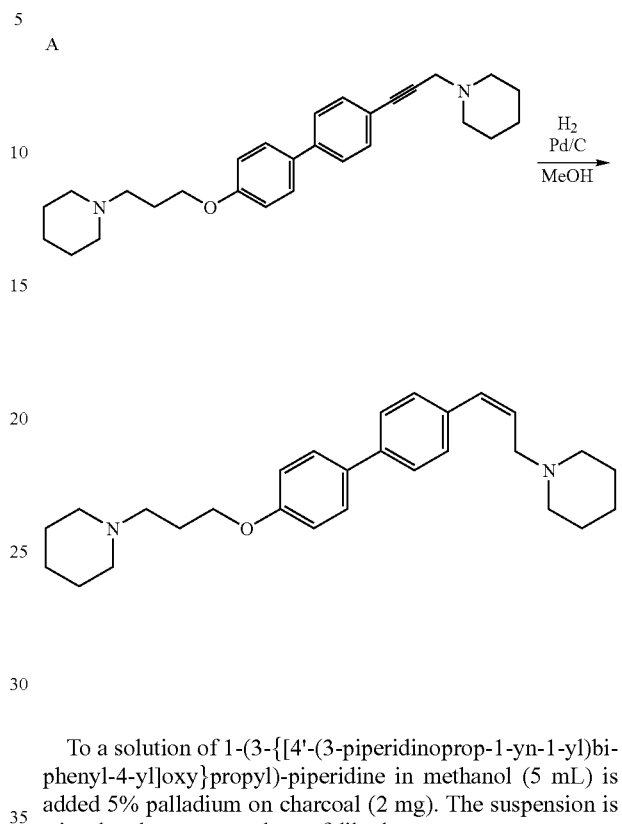

To a solution of 1-(3-{[4'-(3-piperidinoprop-1-yn-1-yl)biphenyl-4-yl]oxy}propyl)-piperidine in methanol (5 mL) is added 5% palladium on charcoal (2 mg). The suspension is stirred under an atmosphere of dihydrogene at room temperature for 5 h, filtered over a celite pad. The filtrate is concentrated under reduced pressure and purified by chromatography over silica gel using a gradient dichloromethane/methanol from 98/2 to 95/5. Fractions containing the expected product are pooled and concentrated under reduced pressure to give 40 mg of (Z)-4-(3-{[4'-(3-piperidinoprop-1-en-1-yl)biphenyl-4-yl]oxy}propyl)piperidine.

1H NMR: (CDCl3)

7.54 (m, 4H, arom), 7.30 (d, J=8.2 Hz, 2H, arom), 6.98 (d, J=8.7 Hz, 2H, arom), 6.58 (d, J=11.9 Hz, 1H, ArCH=), 5.83 (dt, J=11.9 Hz, J=6.4 Hz, 1H, CH=), 4.06 (t, J=6.4 Hz, 2H, CH$_2$O), 3.31 (2d, J=6.4 Hz, =CH$_2$N), 2.49 (m, 10H, 5 CH$_2$N), 2.01 (m, 2H, CH$_2$), 1.64 (m, 8H, 4CH$_2$), 1.45 (m, 4H, 2CH$_2$).

B 1-(3-{[4'-(3-piperidinoprop-1-yn-1-yl)biphenyl-4-yl]oxy}propyl-)piperidine can be prepared as follows:

Following the procedure described in example 43§C, but starting from 1-{3-[(4'-bromobiphenyl-4-yl)oxy]propyl}piperidine (0.75 g), 1-prop-2-yn-1-ylpiperidine (320 mg), triethylamine (20 mL), cuprous iodide (4.2 mg), triphenylphosphine (20 mg) and bis(triphenylphosphinepalladiumdichloride) affords 179 mg of 1-(3-{[4'-(3-piperidinoprop-1-yn-1-yl)biphenyl-4-yl]oxy}propyl)piperidine which oxalate melts at 195° C.

EXAMPLE 46

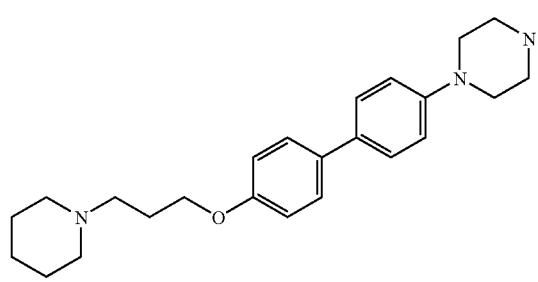

1-methyl-4-[4'-(3-piperidinopropoxy)biphenyl]piperazine

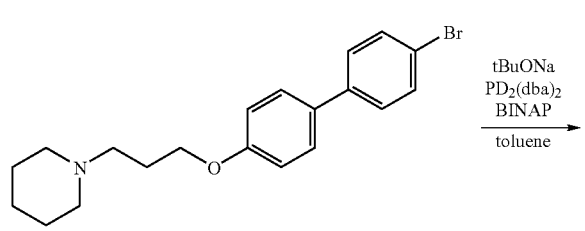

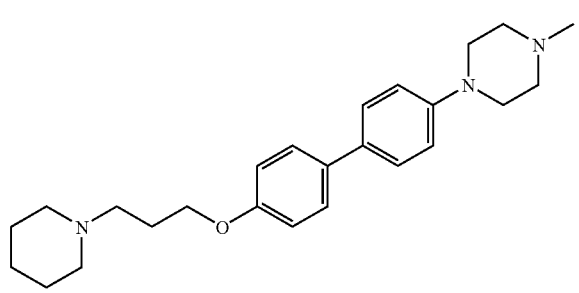

A mixture of 1-{3-[(4'-bromobiphenyl-4-yl)oxy]propyl}piperidine (374 mg), 1-methylpiperazine (133 µL), sodium tert-butylate (139 mg, tris(dibenzylidene-acetone)dipalladium (19 mg) and 2,2'-bis(diphenylphosphine)-1,1'-binaphtyl (32 mg) in toluene (20 mL) is stirred under reflux for 16 h. The suspension is filtered over a clarcel pad which is then rinsed twice with diethyl oxide (50 mL). The combined organic phases are pooled, washed twice with an aqueous saturated solution of sodium chloride, dried over magnesium sulfate and concentrated under reduced pressure. Purification by chromatography over silica gel using a gradient dichloromethane/methanol from 100/0 to 95/5 gives 160 mg of 1-methyl-4-[4'-(3-piperidinopropoxy)biphenyl]piperazine.

1H NMR: (CDCl3)

7.47 (2d, J=8.6 Hz, 4H, arom), 6.98 (d, J=8.6 Hz, 2H, arom), 6.94 (d, J=8.6 Hz, 2H, arom), 4.04 (t, J=6.4 Hz, 2H, CH$_2$O), 3.25 (m, 4H, 2 CH$_2$N), 2.60 (m, 4H, 2 CH$_2$N), 2.47 (m, 6H, 5 CH$_2$N), 2.37 (s, 3H, NCH$_3$), 2.00 (m, 2H, CH$_2$), 1.61 (m, 4H, 2CH$_2$), 1.46 (m, 2H, CH$_2$).

EXAMPLE 47

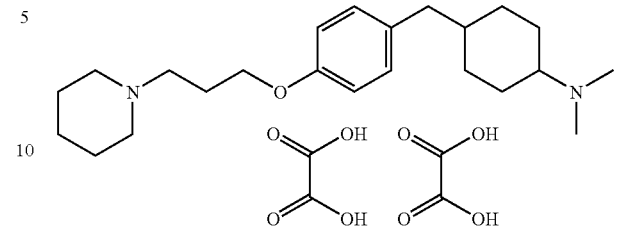

1-{3-[4-(cis-4-dimethylaminocyclohex-1-yl)methylphenoxy]propyl}piperidine, dioxalate and 1-{3-[4-(trans-4-dimethylaminocyclohex-1-yl)methylphenoxy]-propyl}piperidine, dioxalate

A

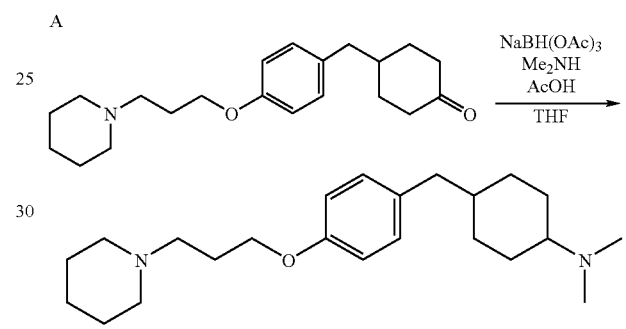

To a solution of 1-{3-[4-(4-oxocyclohex-1-yl)methylphenoxy]propyl}piperidine (110 mg) in a mixture of tetrahydrofuran (2 mL), a 2M solution of dimethylamine in tetrahydrofuran (330 µL) and acetic acid (20 µL) is added triacetoxyborohydride (120 mg). The mixture is stirred for five hours at room temperature and quenched with a saturated aqueous solution of sodium bicarbonate (4 mL). The solution is extracted with ethyl acetate (3 times 10 mL). The combined extracts are washed with a saturated aqueous solution of sodium chloride (twice 5 mL), dried over magnesium sulfate and concentrated under reduced pressure. Purification by column chromatography over silica gel using a gradient ligroin/diethyloxide/triethylamine/methanol from 50/50/1/0.1 to 0/100/1/3 then dichloromethane/methanol/ammonia 90/10/1 affords 52 mg of the crude base which is crystallized with oxalic acid to give 43 mg of 1-{3-[4-(cis-4-dimethylaminocyclohex-1-yl)methylphenoxy]propyl}piperidine, dioxalate.

1H NMR: oxalate (DMSO)

7.08 (d, J=8.2 Hz, 2H, arom), 6.82 (d, J=8.2 Hz, 2H, arom), 3.96 (t, J=5.6 Hz, 2H, CH$_2$O), 3.00 (m, 7H, 3 CH$_2$N, CHN), 2.69 (s, 6H, NCH$_3$), 2.53 (m, 2H, CH$_2$Ar), 2.02 (m, 2H, CH$_2$), 1.80 (m, 1H, CH), 1.67 (m, 8H, 4CH$_2$), 1.46 (m, 6H, 3CH$_2$).

B

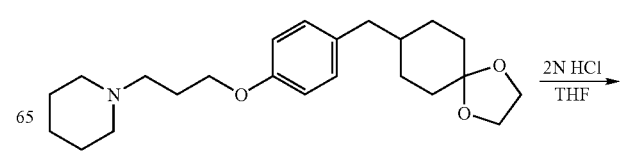

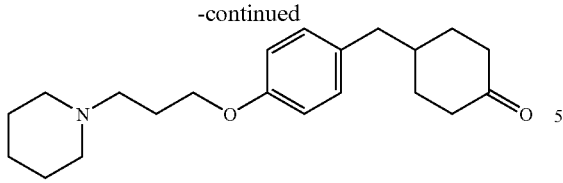

1-{3-[4-(4-oxocyclohex-1-yl)methylphenoxy]propyl}piperidine can be prepared as follows A suspension of potassium carbonate (369 mg) in a solution of 4-[4-(3-chloropropoxy)benzyl]cyclohexanone (250 mg) and piperidine (264 µL) in N,N-dimethylformamide (6 mL) is heated for three hours at a temperature close to 80° C., then for two days at a temperature close to 50° C. Solvent is evaporated and the residue partioned between ethyl acetate (10 mL) and water (10 mL). The organic phase is separated by decantation, washed with a saturated aqueous solution of sodium chloride, dried over magnesium sulfate, concentrated under reduced pressure and purified by column chromatography using a gradient dichloromethane/methanol/ammonia from 99/1/0.1 to 98/2/0.2 to give 270 mg of 1-{3-[4-(4-oxo-cyclohex-1-yl)methylphenoxy]propyl}piperidine.

Rf TLC (dichloromethane/methanol/ammonia 90/10/1)=0.74

C

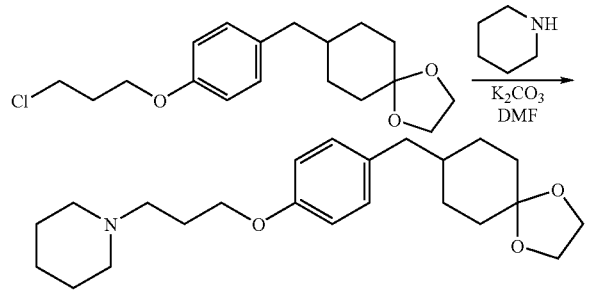

4-[4-(3-chloropropoxy)benzyl]cyclohexanone can be prepared as follows

A solution of 8-[4-(3-chloropropoxy)benzyl]-1,4-dioxas-piro[4.5]decane (630 mg) in a mixture of tetrahydrofuran (9.7 mL) and a 2N aqueous solution of hydrochloric acid (4.85 mL) is stirred for 20 h at room temperature, then concentrated under reduced pressure and diluted with ethyl acetate (10 mL) and alkalinized with an aqueous solution of sodium hydroxide. The organic phase is separated by decantation, washed with a saturated aqueous solution of sodium chloride, dried over magnesium sulfate and concentrated under reduced pressure to give 546 mg of 4-[4-(3-chloropropoxy)benzyl]cyclohexanone used without further purification.

Rf TLC (heptane/ethyl acetate 4/1)=0.38

D

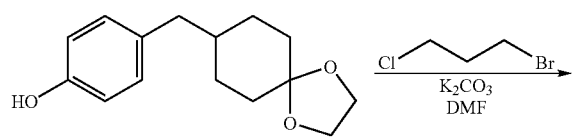

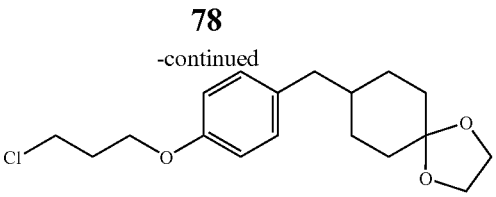

8-[4-(3-chloropropoxy)benzyl]-1,4-dioxaspiro[4.5]decane can be prepared as follows A suspension of potassium carbonate 3.92 g) in a solution of 8-(4-hydroxybenzyl)-1,4-dioxaspiro[4.5]decane (1.41 g) and 1-bromo-3-chloropropane (2.81 mL) in N,N-dimethylformamide (35 mL) is stirred for 20 h at room temperature. Diethyl oxide (210 mL) is added and the suspension is filtered. The filtrate is washed with water (twice 50 mL), dried over magnesium sulfate and concentrated under reduced pressure to give 1.635 g of 8-[4-(3-chloropropoxy)benzyl]-1,4-dioxaspiro[4.5]-decane used without further purification.

Rf TLC (heptane/ethyl acetate 4/1)=0.47.

E

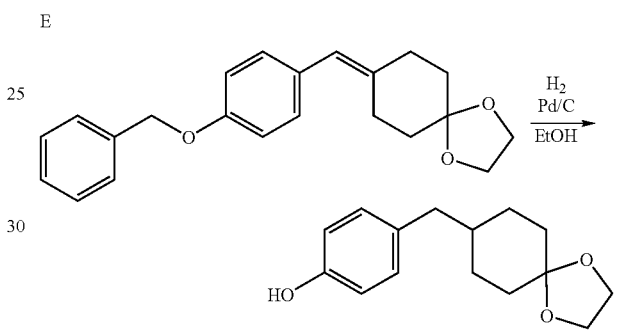

8-(4-hydroxybenzyl)-1,4-dioxaspiro[4.5]decane can be prepared as follows A suspension of 10% palladium on charcoal (139 mg) in a solution of 8-(4-benzyloxybenzylidene)-1,4-dioxaspiro[4.5]decane (1.93 g) in ethanol (50 mL) is shacked under dihydrogene (3 bar) for 24 h at room temperature, filtered over a clarcel pad and the filtrate concentrated under reduced pressure to give 1.418 g of 8-(4-hydroxyben-zyl)-1,4-dioxaspiro[4.5]decane as a beige solid.

Rf TLC (heptane/ethyl acetate 1/1)=0.62

F

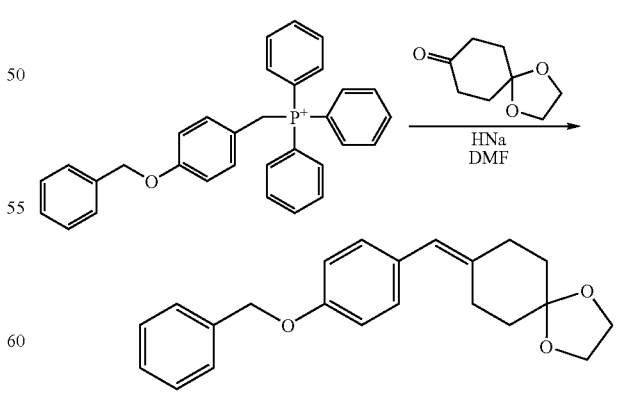

8-(4-benzyloxybenzylidene)-1,4-dioxaspiro[4.5]decane can be prepared as follows

To a suspension of sodium hydride (729 mg 60% in mineral oil) in N,N-dimethylformamide containing one drop of pentane is added (4-benzyloxybenzyl)triphenylphosphonium chloride (7.52 g). The mixture is stirred for 40 min, then 1,4-dioxaspiro[4.5]decan-8-one (2.37 g) is added. The mixture is stirred for one hour at room temperature, the suspension turning from red to green. The mixture is poured into ice (250 g) and extracted with ethyl acetate (4 times 100 mL). The organic extracts are pooled, washed with saturated aqueous solution of sodium chloride (3 times 50 mL), dried over magnesium sulfate, concentrated under reduced pressure and purified by column chromatography over silica gel using a gradient heptane/ethyl acetate from 90/10 to 60/40 to give 2.43 g of 8-(4-benzyloxybenzylidene)-1,4-dioxaspiro[4.5]decane as a colorless oil.

Rf TLC (heptane/ethyl acetate 1/1)=0.73

EXAMPLE 48

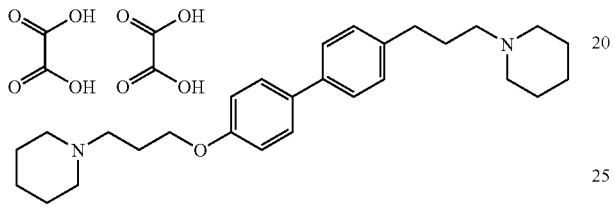

4-(3-{[4'-(3-piperidinopropyl)biphenyl-4-yl]oxy}propyl)piperidine, dioxalate

A suspension of 10% palladium on charcoal (70 mg) in a solution of (E)-1-(3-{[4'-(3-piperidinoprop-1-en-1-yl)biphenyl-4-yl]oxy}propyl)piperidine (0.2 g) in ethanol is stirred under an atmosphere of dihydrogene at room temperature for 20 h, filtered over a clarcel pad and concentrated under reduced pressure. The residue is purified by column chromatography over silica gel with a gradient dichloromethane/methanol/ammonia from 99/1/0.1 to 97/3/0.3 then with another chromatography over silica gel with dichloromethane/methanol/ammonia 99/1/0.1 as eluent. The crude base is converted to the dioxalate with oxalic acid in ethanol to give 37 mg of 4-(3-{[4'-(3-piperidinopropyl)biphenyl-4-yl]oxy}propyl)piperidine, dioxalate melting at 130° C.

1H NMR: oxalate (DMSO)

7.56 (m, 4H), 7.26 (d, J=8.1 Hz, 2H, arom), 6.98 (d, J=8.7 Hz, 2H, arom), 4.05 (t, J=5.8 Hz, 2H, CH$_2$O), 3.06 (m, 12H, 6 CH$_2$N), 2.61 (t, J=7.5 Hz, 2H, CH$_2$Ar), 2.09 (m, 2H, CH$_2$), 1.94 (m, 2H, CH$_2$), 1.60 (m, 8H, 4CH$_2$), 1.50 (m, 4H, 2 CH$_2$).

EXAMPLE 49

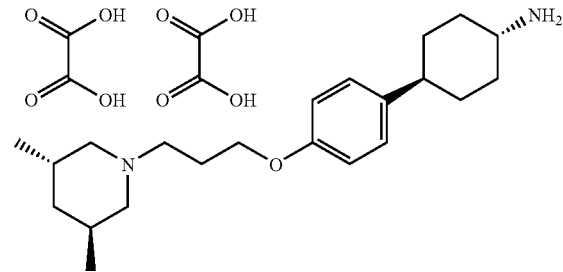

(3S,5S)-1-{3-[4-(trans-4-aminocyclohex-1-yl)phenoxy]propyl}-3,5-dimethylpiperidine, dioxalate

A

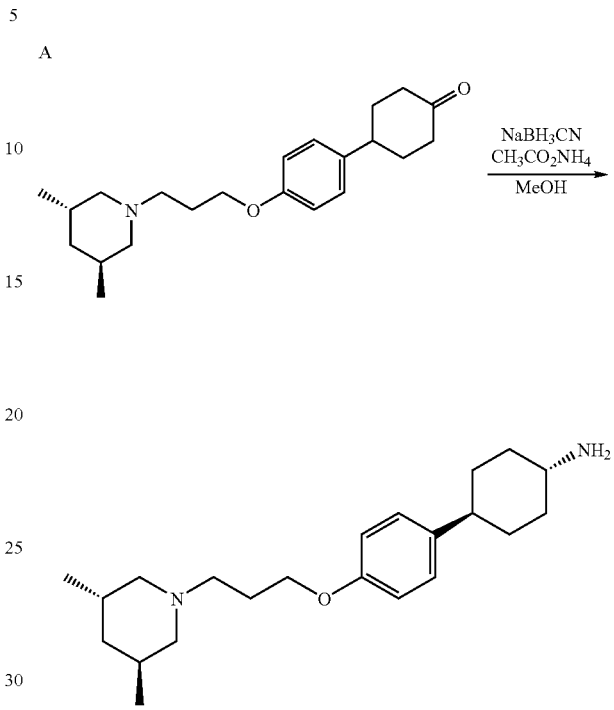

A mixture of (3S,5S)-1-{3-[4-(4-oxocyclohex-1-yl)phenoxy]propyl}-3,5-dimethylpiperidine (392 mg), ammonium acetate (745 mg) and sodium cyanoborohydride (364 mg) in methanol (15 mL) is stirred under reflux for two hours, then cooled to room temperature and quenched with a 3N aqueous solution of hydrochloric acid. Water (10 mL) is added and the mixture is made alkaline upon addition of 35% aqueous solution of sodium hydroxide, extracted with dichloromethane, dried over magnesium sulfate and concentrated under reduced pressure. Purification by column chromatography over silica gel with diethyl oxide/methanol/triethylamine 10/0.4/0.2 as eluent affords 65 mg of crude base that is converted to 60 mg of (3S,5S)-1-{3-[4-(trans-4-aminocyclohex-1-yl)phenoxy]-propyl}-3,5-dimethylpiperidine, dioxalate melting at 234° C.

1H NMR: oxalate (DMSO)

7.11 (d, J=8.3 Hz, 2H, arom), 6.80 (d, J=8.3 Hz, 2H, arom), 3.93 (t, J=5.7 Hz, 2H, CH$_2$O), 3.00 (m, 1H), 2.70 (m, 4H), 2.41 (m, 3H), 2.1-1.7 (m, 8H), 1.5-1.3 (m, 6H) 0.92 (2d, J=6.7 Hz, 6H, 2 CH$_3$).

B

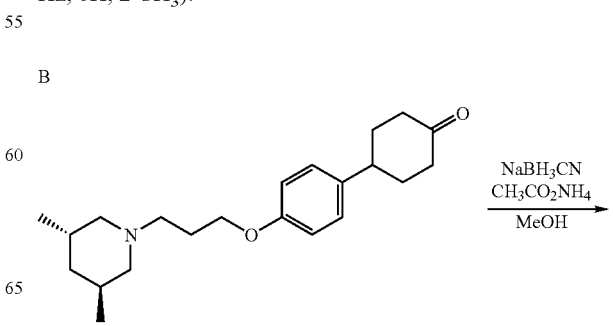

-continued

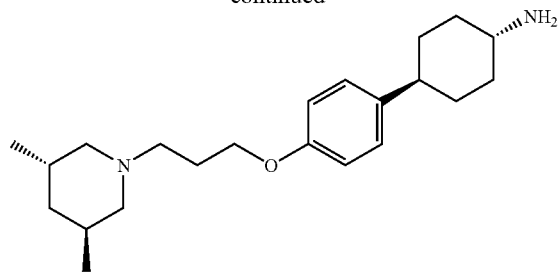

(3S,5S)-1-{3-[4-(4-oxocyclohex-1-yl)phenoxy]propyl}-3,5-dimethylpiperidine can be prepared as follows Following the procedure described in example 47§C, but starting from potassium carbonate (1.24 g), 4-[4-(3-chloropropoxy)phenyl]cyclohexanone (0.8 g), (3S,5S)-3,5-dimethylpiperidine hydrochloride (539 mg), a catalytic amount of potassium iodide and N,N-dimethylformamide (10 mL), affords 332 mg of (3S,5S)-3,5-dimethyl-1-{3-[4-(4-oxocyclohexyl)phenoxy]propyl}piperidine as a yellow oil used without further purification.

EXAMPLE 50

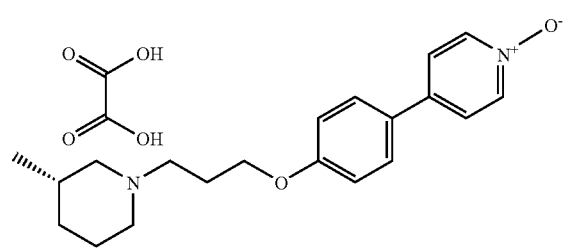

(3S)-4-{4-[3-(3-methylpiperidin-1-yl)propoxy]phenyl}pyridine 1-oxide, oxalate

A

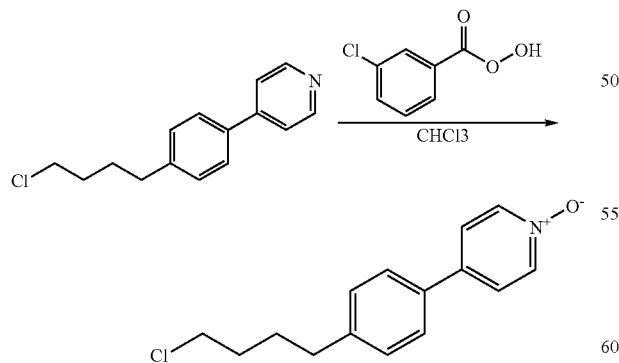

Following the procedure described in example 47§C, but starting from potassium carbonate (1.71 g), 4-[4-(3-chloropropoxy)phenyl]pyridine 1-oxide (1.09 g), (3S)-3-methylpiperidine mandelate (1.25 g) and N,N-dimethylformamide (20 mL), affords 19 mg of the crude base which is converted to the oxalate with oxalic acid to give 13 mg of (3S)-4-{4-[3-(3-methylpiperidin-1-yl)propoxy]-phenyl}pyridine 1-oxide, oxalate.

1H NMR: (CDCl3)
8.18 (d, J=7.22, 2H, arom), 7.46 (m, 4H, arom), 6.96 (d, J=8.7, 2H, arom), 4.05 (t, J=5.8 Hz, 2H, CH$_2$O), 3.03 (m, 2H, CH$_2$N), 2.67 (m, 2H, CH$_2$N), 2.2-1.8 (m, 9H), 0.86 (d, J=6.06 Hz, CH$_3$).

B

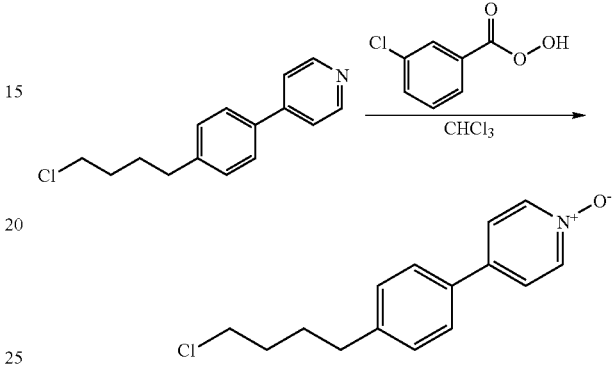

4-[4-(3-chloropropoxy)phenyl]pyridine 1-oxide can be prepared as follows:

A mixture of 4-[4-(3-chloropropoxy)phenyl]pyridine (1.22 g) and metachloroperbenzoic acid (1.82 g) in chloroform (25 mL) is stirred at room temperature for four hours, then concentrated under reduced pressure and purified by column chromatography over silica gel using a gradient dichloromethane/methanol from 100/0 to 95/5. Fractions containing the expected product are pooled and concentrated under reduced pressure to give 1.09 g of 4-[4-(3-chloropropoxy)phenyl]pyridine 1-oxide as a pale yellow solid used without further purification.

C 4-[4-(3-chloropropoxy)phenyl]pyridine can be prepared as follows:

Following the procedure described in example 24, but starting from 1-bromo-4-(3-chloropropoxy)benzene (2.5 g), potassium carbonate (4.14 g), 4-pyridylboronic acid (1.47 g) and palladium tetrakistriphenylphosphine (116 mg) in toluene (24 mL) affords 2.11 g of 4-[4-(3-chloropropoxy)phenyl] pyridine as a white solid.

EXAMPLE 51

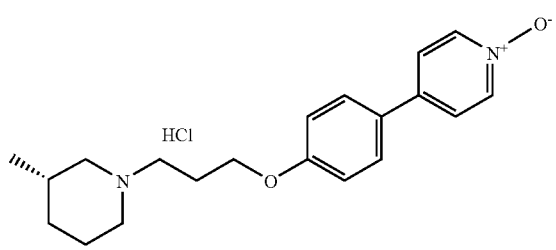

(3S)-4-{4-[3-(3-methylpiperidin-1-yl)propoxy]phenyl}pyridine 1-oxide, hydrochloride To a solution of 4-[4-(3-chloropropoxy)phenyl]pyridine 1-oxide (231 mg) and triethylamine (366 µL) in N,N-dimethylformamide (5 mL) are added potassium carbonate (363 mg) and (3S)-3-methylpiperidine mandelate (264 mg). The mixture is stirred at a temperature close to 60° C. for four hours. An additional amount of (3S)-3-methylpiperidine mandelate (100 mg) is added and heating is continued overnight. The suspension is filtered and the precipitate washed with ethyl acetate. The combined organic phases are concentrated under reduced pressure. The residue is purified twice by column chromatography over silica gel using a gradient dichloromethane/methanol/triethylamine from 100/0/0 to 95/5/0.1. Fractions containing the expected product are pooled and concentrated under reduced pressure to give 90 mg of the crude base which is converted to the hydrochloride with an ethereal solution of hydrogen chloride in ethanol to give 75 mg of (3S)-4-{4-[3-(3-methylpiperidin-1-yl)propoxy]phenyl}pyridine 1-oxide, hydrochloride melting at 74° C.

EXAMPLE 52

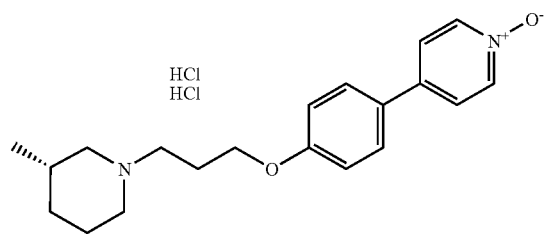

(3S)-4-{4-[3-(3-methylpiperidin-1-yl)propoxy]phenyl}pyridine 1-oxide, dihydrochloride The crude base is dissolved in ethanol. Addition of a 4M solution of hydrogen chloride in ethyl acetate affords (3S)-4-{4-[3-(3-methylpiperidin-1-yl)propoxy]-phenyl}pyridine 1-oxide, dihydrochloride melting at 193° C.

EXAMPLE 53

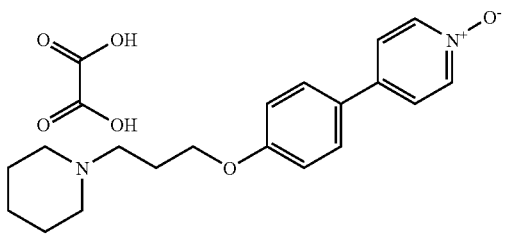

4-[4-(3-piperidinopropoxy)phenyl]pyridine 1-oxide, oxalate

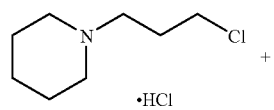

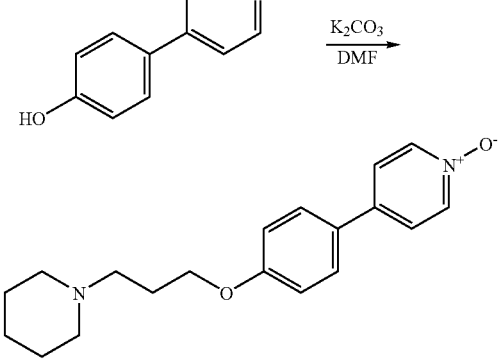

A A mixture of 4-(4-hydroxyphenyl)pyridine 1-oxide (250 mg), potassium carbonate (560 mg) and 1-(3-chloropropyl)piperidine, hydrochloride in N,N-dimethylformamide (10 mL) is heated at a temperature close to 65° C. overnight, then cooled back to room temperature and filtered. The filtrate is concentrated under reduced pressure and the residue purified by chromatography over silica gel (eluent dichloromethane/methanol from 100/0 to 90/10). Fraction containing the compound are pooled and concentrated under reduced pressure. Crude base is diluted with ethanol, oxalic acid (28 mg) is added and solvent removed under reduced pressure to give 40 mg of 4-[4-(3-piperidino-propoxy)phenyl]pyridine 1-oxide, oxalate as a viscous yellow product.

NMR (DMSO):

8.17 (d, 2H, Harom, J=7.0 Hz); 7.70 (d, 2H, Harom, J=8.7 Hz); 7.67 (d, 2H, Harom, J=7.0 Hz); 7.04 (d, 2H, Harom, J=8.7 Hz); 4.10 (t, 2H, CH$_2$O, J=5.9 Hz); 3.00-3.30 (m, 6H, 3 CH$_2$N); 2.15 (m, 2H, CH$_2$); 1.40-1.80 (m, 6H, 3CH$_2$).

B 4-(4-hydroxyphenyl)pyridine 1-oxide can be prepared as follows:

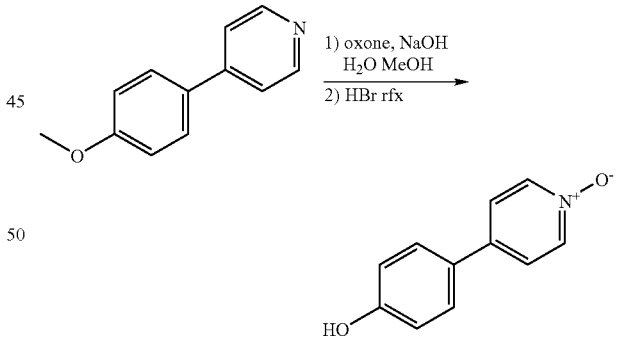

To a solution of oxone (166 g) in water (300 mL) and methanol (590 mL) is added portion wise 4-(4-methoxyphenyl)pyridine (55.6 g). Addition of a 5N aqueous solution of sodium hydroxide maintains pH around 5.5 for 6 hours. Precipitate is filtered and rinsed with methanol (250 mL). A 1M aqueous solution of sodium metabisulfite (60 mL) is added to the filtrate. The solution is stirred for 20 minutes, pH adjusted to around 10 with a 5N aqueous solution of sodium hydroxide and concentrated to a volume of approximately 300 mL. A 48% aqueous solution of hydrobromic acid is added and the solution heated under reflux for 3.5 hours. After cooling back to room temperature, a precipitate appears which is filtered and dried, dissolved in a 48% aqueous solution of hydrobromic acid and heated under reflux for 4.5 hours. On cooling, a precipitate appears which is filtered and dried to give 65 g of 4-(4-hydroxyphenyl)pyridine 1-oxide hydrobromide.

A second crop is filtered and purified over silica gel (eluent dichloromethane/methanol 100/0 to 90/10) to give 2 g of 4-(4-hydroxyphenyl)pyridine 1-oxide.

EXAMPLE 54

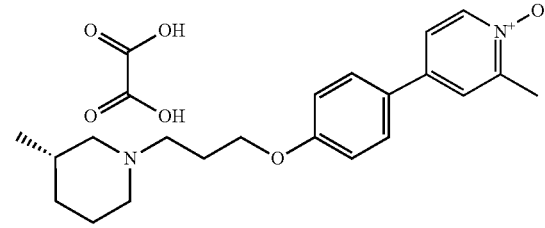

2-methyl-4-(4-{3-[(3S)-3-methylpiperidin-1-yl] propoxy}phenyl)pyridine 1-oxide, oxalate

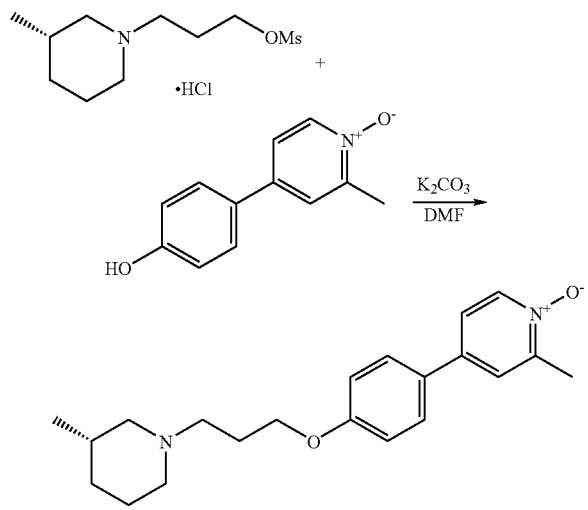

A A mixture of 4-(4-hydroxyphenyl)-2-methylpyridine 1-oxide (55 mg), potassium carbonate (187 mg) and (3S)-1-(3-methanesulfonyloxypropyl)-3-methylpiperidine hydrochloride in N,N-dimethylformamide (3 mL) is heated at a temperature close to 65° C. overnight and cooled back to room temperature. Water (5 mL) is added; the solution is washed with methylcyclohexane (twice 10 mL) and concentrated under reduced pressure. The residue is purified by chromatography over silica gel (eluent dichloromethane/methanol from 95/5 to 80/20). Fraction containing the expected product are pooled and concentrated under reduced pressure. The crude base is diluted in ethanol, oxalic acid (7 mg) is added and solvent is removed under reduced pressure to give 32 mg of (3S)-2-methyl-4-{4-[3-(3-methylpiperidin-1-yl)propoxy]phenyl}pyridine 1-oxide, oxalate as a brown crystalline material.

NMR (DMSO):

8.22 (d, 1H, Harom, J=6.9 Hz); 7.81 (s, 1H, Harom); 7.73 (d, 2H, Harom, J=8.7 Hz); 7.57 (dd, 1H, Harom, J=6.9 Hz+J=2.6 Hz); 7.03 (d, 2H, Harom, J=8.7 Hz); 4.09 (t, 2H, CH$_2$O); 2.70-3.60 (m, 6H, 3 CH$_2$N); 2.37 (s, 3H, CH$_3$); 2.15 (m, 2H, CH$_2$); 1.60-1.90 (m, 4H); 1.10 (m, 1H); 0.88 (d, 3H, CH$_3$).

B 4-(4-hydroxyphenyl)-2-methylpyridine 1-oxide can be obtained as follows

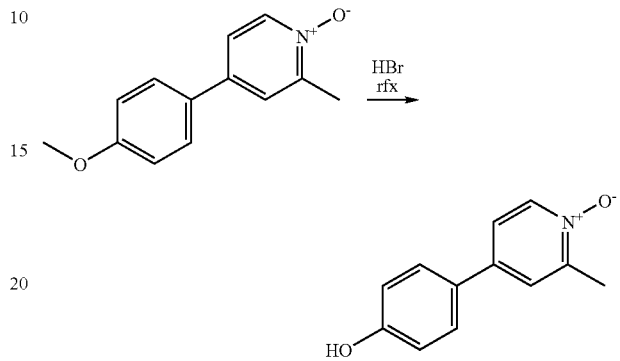

A solution of 4-(4-methoxyphenyl)-2-methylpyridine 1-oxide (384 mg) in a 48% aqueous solution of hydrobromic acid (2.08 mL) is heated under reflux for 4 hours. The mixture is allowed to cool back to room temperature, water and ethyl acetate are added and the two phases separated by decantation. The aqueous phase is concentrated under reduced pressure. The residue is dissolved in chloroform (4 mL); triethylamine (1 equivalent) is added followed by metachloroperbenzoic acid (1 equivalent). The mixture is stirred for two hours at room temperature; a few drops of methanol are added to dissolve the reactants and stirred again for one hour at room temperature. Concentration under reduced pressure affords 55 mg of 4-(4-hydroxyphenyl)-2-methylpyridine 1-oxide as a yellow oil used without further purification.

C 4-(4-methoxyphenyl)-2-methylpyridine 1-oxide can be obtained as follows

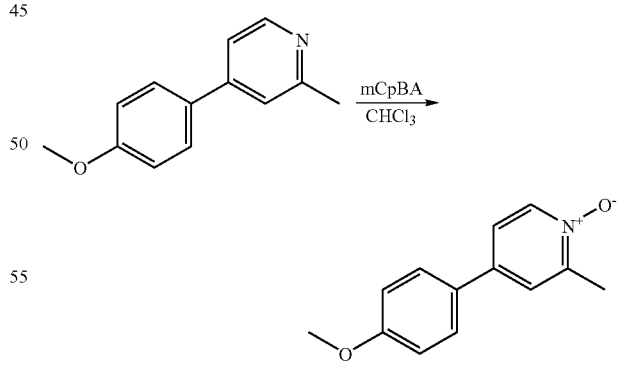

A mixture of 4-(4-methoxyphenyl)-2-methylpyridine (375 mg) and metachloroperbenzoic acid (70%, 695 mg) in chloroform is stirred at room temperature for two hours. Concentration and purification over silica gel (eluent dichloromethane/methanol from 100/0 to 90/10) affords 384 mg of 4-(4-methoxyphenyl)-2-methylpyridine 1-oxide as an orange oil used without further purification.

D 4-(4-methoxyphenyl)-2-methylpyridine can be obtained as follows

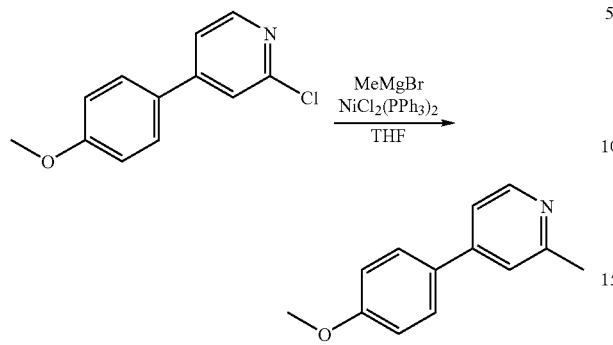

A mixture of 2-chloro-4-(4-methoxyphenyl)pyridine (660 mg) and bis(triphenyl-phosphine)nickeldichloride (200 mg) in anhydrous tetrahydrofuran (7.5 mL) is cooled to a temperature close to 0° C. A solution of methylmagnesiumbromide in tetrahydrofuran (2.6 M, 2 mL) is added slowly. The mixture is stirred at room temperature for two hours, concentrated under reduced pressure and dissolved in methyl tert-butyl ether (10 mL). Alkaloids are extracted with a 3N aqueous solution of hydrochloric acid (3 times 10 mL). Extracts are pooled, alkalinised and back extracted with methyl tert-butyl ether (3 times 20 mL) and dichloromethane (30 mL). Organic phases are dried over magnesium sulphate, concentrated under reduced pressure and purified over silica gel (eluent dichloromethane/methanol from 100/0 to 95/5). Fraction containing the expected product are pooled and concentrated under reduced pressure to give 385 mg of 4-(4-methoxyphenyl)-2-methylpyridine as a clear brown powder used without further purification.

E 2-chloro-4-(4-methoxyphenyl)pyridine can be obtained as follows

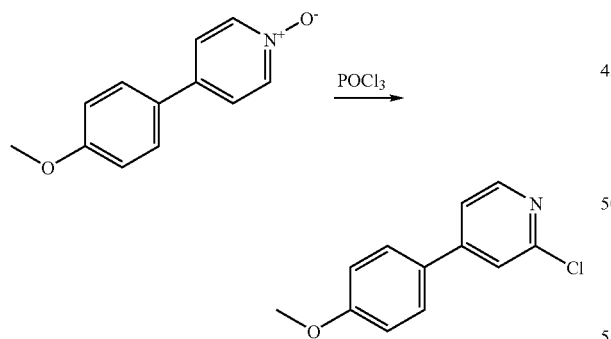

A mixture of 4-(4-methoxyphenyl)pyridine 1-oxide (1.68 g) and phosphorus oxychloride (15 mL) is heated under reflux for six hours and concentrated under reduced pressure. Toluene is added and the mixture concentrated under reduced pressure. The residue is dissolved in hot toluene (20 mL) and the organic phase washed with water (twice 10 mL) a saturated aqueous sodium hydrogenocarbonate solution (10 mL), dried over magnesium sulphate and concentrated under reduced pressure to give 1.45 g of 2-chloro-4-(4-methoxyphenyl)pyridine as an orange coloured crystalline material.

F 4-(4-methoxyphenyl)pyridine 1-oxide can be prepared as follows

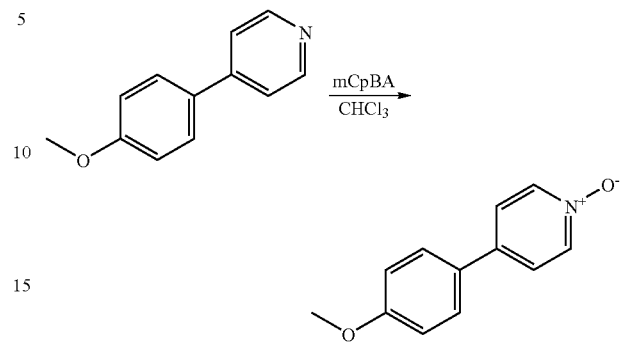

A solution of 4-(4-methoxyphenyl)pyridine (5.68 g) and metachloroperbenzoic acid (70%, 11.34 g) in chloroform is stirred for 2.5 hours at room temperature, concentrated under reduced pressure and purified by chromatography over silica gel (eluent dichloromethane/methanol from 100/0 to 90/10) to give 5.62 g of 4-(4-methoxyphenyl)pyridine 1-oxide used without further purification.

EXAMPLE 55

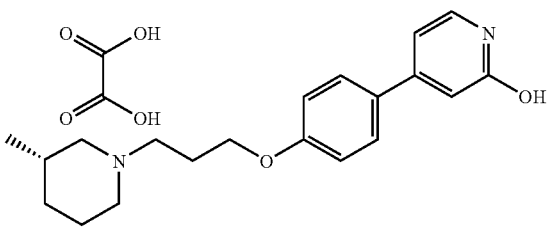

2-hydroxy-4-(4-{3-[(3S)-3-methylpiperidin-1-yl]propoxy}phenyl)pyridine, oxalate

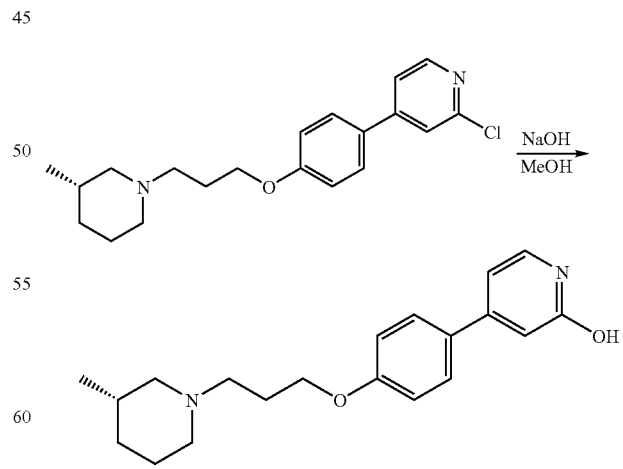

A A mixture of 2-chloro-4-(4-{3-[(3S)-3-methylpiperidin-1-yl]propoxy}phenyl)pyridine (345 mg), sodium hydroxide (288 mg) and methanol (1.55 mL) is heated overnight at a temperature close to 170° C. in a sealed tube. The mixture is cooled to a temperature close to 0° C. and neutralized with a cold concentrated aqueous hydrochloric solution. Methanol (1.3 mL) is added and the precipitate separated by filtration. The filtrate is concentrated under reduced pressure and purified by chromatography over silica gel (eluent dichloromethane/methanol from 100/0 to 80/20). Fraction containing the expected product are pooled and concentrated under reduced pressure. The crude base is dissolved in ethanol; oxalic acid (118 mg) is added followed by diethyl ether. The precipitate that appears is separated by filtration, washed with ethanol and dried under reduced pressure to give 110 mg of 2-hydroxy-4-(4-{3-[(3S)-3-methylpiperidin-1-yl]propoxy}phenyl)pyridine, oxalate as a white powder melting at 110° C.

NMR (DMSO):

10.7 (bs, 1H, NH); 7.68 (d, 2H, Harom, J=8.5 Hz); 7.60 (d, 1H, Harom, J=6.7 Hz); 7.04 (d, 2H, Harom, J=8.5 Hz); 6.75-6.79 (s+d, 2H, Harom, J=6.7 Hz); 4.10 (t, 2H, CH$_2$O, J=5.9 Hz); 2.50-3.40 (m, 6H, 3 CH$_2$N); 2.20 (m, 2H, CH$_2$); 1.60-2.10 (m, 4H); 1.00 (m, 1H); 0.86 (d, 3H, CH$_3$, J=6.5 Hz).

EXAMPLE 56

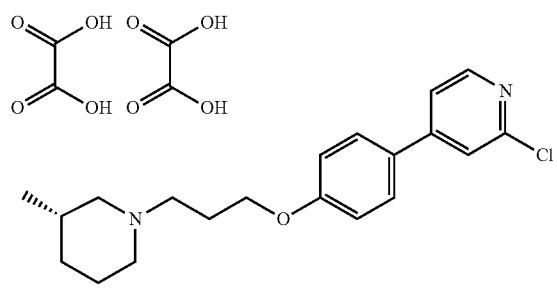

2-chloro-4-(4-{3-[(3S)-3-methylpiperidin-1-yl]propoxy}phenyl)pyridine, dioxalate

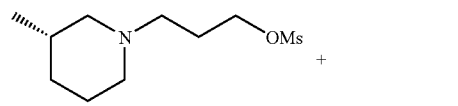
+
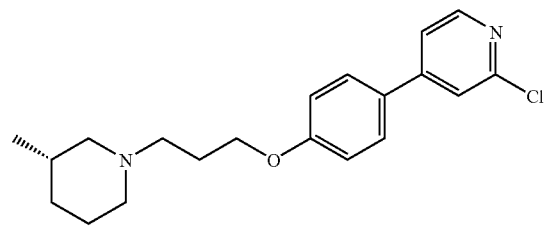

A To a mixture of 2-chloro-4-(4-hydroxyphenyl)pyridine hydrobromide (593 m g) and potassium carbonate (1.66 g) in N,N-dimethylformamide (15 mL) heated at a temperature close to 65° C. is added (3S)-1-(3-methane-sulfonyloxypropyl)-3-methylpiperidine hydrochloride (625 mg). The mixture is heated at a temperature close to 65° C. for six hours, allowed to cool back to room temperature and filtered. The precipitate is washed with N,N-dimethylformamide and the organic phases are concentrated under reduced pressure. The residue is purified by column chromatography over silica gel (eluent dichloromethane/methanol from 100/0 to 90/10) to afford 434 mg of 2-chloro-4-(4-{3-[(3S)-3-methylpiperidin-1-yl]propoxy}phenyl)pyridine as an orange oil. Conversion to the oxalate is performed by mixing the crude base (87 mg) and oxalic acid (46 mg) in a mixture of ethanol and diethyl ether. Filtration of the insoluble and drying under reduced pressure gives 82 mg of 2-chloro-4-(4-{3-[(3S)-3-methylpiperidin-1-yl]propoxy}phenyl)pyridine, dioxalate as an off white solid melting at 143° C.

B 2-chloro-4-(4-hydroxyphenyl)pyridine hydrobromide can be prepared as follows

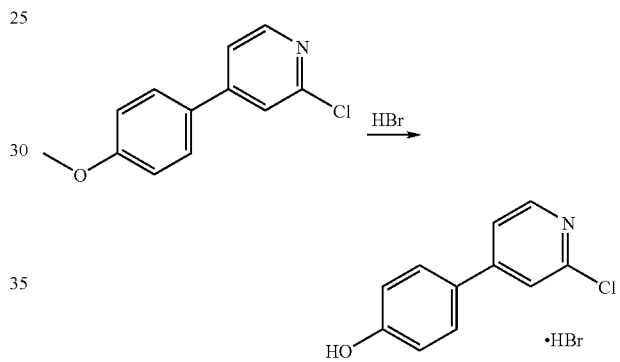

A mixture of 2-chloro-4-(4-methoxyphenyl)pyridine (4.6 g) and 48% aqueous hydrobromic acid solution is heated under reflux for 3.5 hours and allowed to cool back to room temperature. The precipitate that appears is separated by filtration, washed with water and dried under reduced pressure to give 4.9 g of 2-chloro-4-(4-hydroxyphenyl)pyridine hydrobromide as a yellow solid used without further purification.

EXAMPLE 57

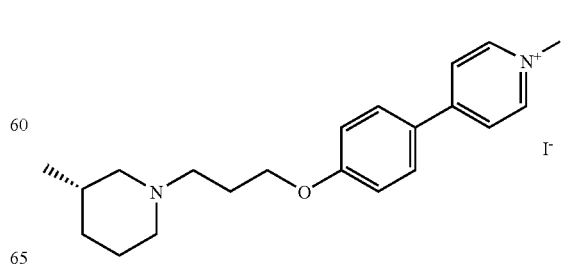

1-methyl-4-(4-{3-[(3S)-3-methylpiperidin-1-yl]
propoxy}phenyl)pyridinium, iodide

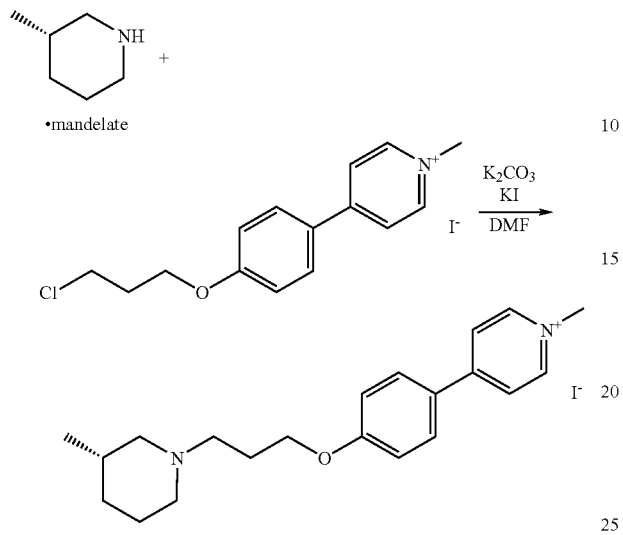

A  A mixture of 1-methyl-4-[4-(3-chloropropoxy)phenyl] pyridinium, iodide (442 mg), potassium carbonate (470 mg), (3S)-3-methylpiperidine mandelate (355 mg) and a catalytic amount of potassium iodide in N,N-dimethylformamide (5 mL) is heated for six hours at a temperature close to 100° C., allowed to cool back to room temperature and filtrated. The precipitate is rinsed with N,N-dimethylformamide and the filtrate concentrated under reduced pressure. The residue is purified twice by chromatography over silica gel (eluent dichloromethane/methanol from 98/2 to 90/10 for the first one, dichloromethane/methanol/ammonia from 95/5/1 to 90/10/1 for the second one) to give 60 mg of 1-methyl-4-(4-{3-[(3S)-3-methylpiperidin-1-yl]propoxy}phenyl)-pyridinium, iodide NMR (DMSO):
8.88 (d, 2H, Harom, J=6.6 Hz); 8.41 (d, 2H, Harom, J=6.6 Hz); 8.07 (d, 2H, Harom, J=8.5 Hz); 7.15 (d, 2H, Harom, J=8.5 Hz); 4.25 (s, 3H, CH$_3$N); 4.13 (t, 2H, CH$_2$O, J=5.9 Hz); 2.50-3.50 (m, 6H, 3 CH$_2$N); 2.00 (m, 2H, CH$_2$); 1.40-1.70 (m, 4H); 0.90 (m, 1H); 0.84 (d, 3H, CH$_3$, J=6.1 Hz).

B  1-methyl-4-(4-(3-chloropropoxy)phenyl]pyridinium, iodide can be obtained as follows

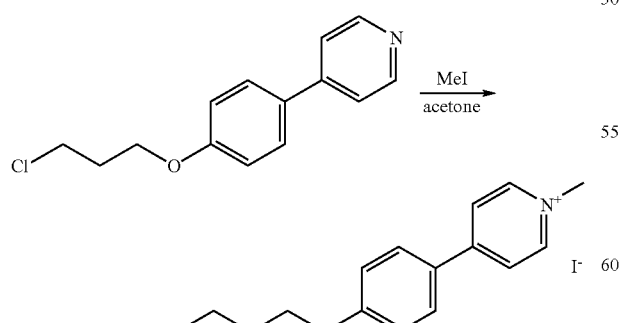

To a solution of 4-(4-(3-chloropropoxy)phenyl]pyridine (408 mg) in acetone (1 mL) is added iodomethane (0.206 mL). The solution is stirred at room temperature for one hour.

The precipitate that has appeared is separated by filtration, washed twice with diethyl ether and dried under reduced pressure to give 442 mg of 1-methyl-4-(4-(3-chloropropoxy) phenyl]pyridinium, iodide used without further purification.

C  4-(4-(3-chloropropoxy)phenyl]pyridine can be prepared as follows

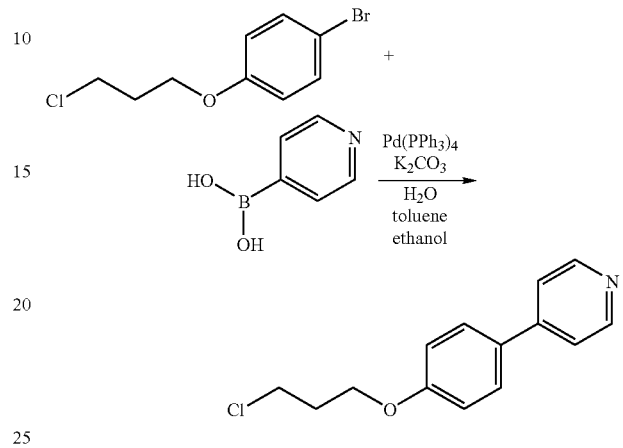

To a mixture of 1-bromo-4-(3-chloropropoxy)benzene (1.25 g) and tetrakistriphenylphosphinepalladium (58 mg) in toluene (12 mL) and potassium carbonate (2.07 g) in water (6 mL) is added pyridine-4-boronic acid (380 mg) dissolved in ethanol. The mixture is heated for five hours at a temperature close to 80° C. Solvents are removed under reduced pressure and the residue dissolved in ethyl acetate. The organic phase is washed with a 10% aqueous solution of potassium hydroxide, then with water, dried over magnesium sulfate, filtered and concentrated. The residue is purified by chromatography over silica gel (eluent dichloromethane/methanol from 100/0 to 95/5) to give 408 mg of 4-(4-(3-chloropropoxy)phenyl] pyridine as an ochre oil used without further purification.

EXAMPLE 58

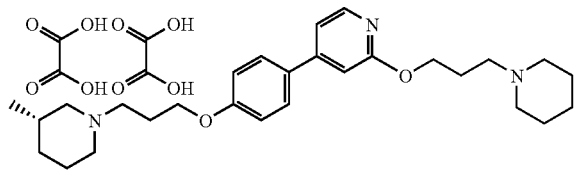

2-(3-piperidinopropoxy)-4-(4-{3-[(3S)-3-methylpiperidin-1-yl]propoxy}phenyl)-pyridine, dioxalate

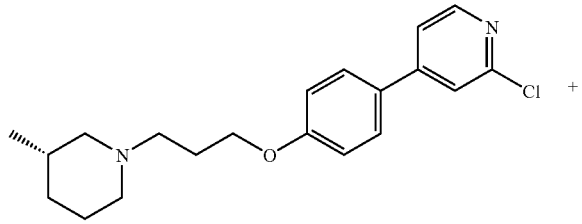

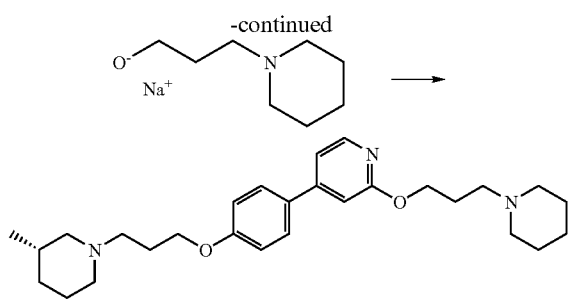

To 1-(3-hydroxypropyl)piperidine (287 mg) are successively added sodium (46 mg) and 2-chloro-4-(4-{3-[(3S)-3-methylpiperidin-1-yl]propoxy}phenyl)pyridine (345 mg). The mixture is heated overnight, cooled back to room temperature and dissolved in dichloromethane (20 mL). The organic phase is washed with water (20 mL), dried over magnesium sulphate, concentrated under reduced pressure and purified over silica gel (eluent (dichloromethane/methanol from 100/0 to 90/10). Fraction containing the expected product are pooled and concentrated under reduced pressure. The crude base is dissolved in ethanol, oxalic acid (32 mg) is added and the precipitate that appears separated by filtration and dried to give 70 mg of 2-(3-piperidinopropoxy)-4-(4-{3-[(3S)-3-methylpiperidin-1-yl]propoxy}phenyl)pyridine, dioxalate as a white solid melting at 122° C.

NMR (DMSO):

8.14 (d, 1H, Harom, J=5.4 Hz); 7.73 (d, 2H, Harom, J=8.7 Hz); 7.27 (dd, 1H, Harom, J=5.4 Hz+J=1.6 Hz); 7.02 (d, 2H, Harom, J=8.7 Hz); 7.01 (d, 1H, Harom, J=1.6 Hz); 4.31 (t, 2H, CH$_2$O, J=6.1 Hz); 4.07 (t, 2H, CH$_2$O, J=5.9 Hz); 2.50-3.40 (m, 12H, 6 CH$_2$N); 1.40-2.40 (m, 14H); 1.00 (m, 1H); 0.87 (d, 3H, CH$_3$, J=6.5 Hz).

EXAMPLE 59

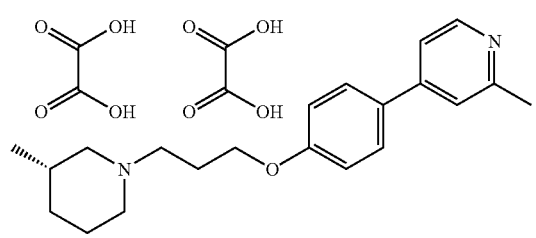

2-methyl-4-(4-{3-[(3S)-3-methylpiperidin-1-yl]propoxy}phenyl)pyridine, dioxalate A Following the procedure described in example 56A, but starting from 2-methyl-4-(4-hydroxyphenyl)pyridine hydrobromide (130 m g), potassium carbonate (415 g), (3S)-1-(3-methanesulfonyloxypropyl)-3-methylpiperidine hydrochloride (170 mg) and N,N-dimethylformamide (5 mL) gives 82 mg of 2-methyl-4-(4-{3-[(3S)-3-methylpiperidin-1-yl]propoxy}phenyl)pyridine, dioxalate as a pale yellow powder melting at 97° C.

B 2-methyl-4-(4-hydroxyphenyl)pyridine hydrobromide can be prepared as follows

Following the procedure described in example 56B, but starting from (4-methoxyphenyl)-2-methylpyridine (141 mg) and an aqueous solution of hydrobromic acid (48%, 0.85 mL) gives 130 mg of 2-methyl-4-(4-hydroxyphenyl)pyridine hydrobromide as a yellow powder used without further purification.

EXAMPLE 60

1-{3-[4-(4-hydroxycyclohexyl)phenoxy]propyl}piperidine, oxalate

To a solution of 1-{3-[4-(4-oxocyclohexyl)phenoxy]propyl}piperidine (250 mg) in methanol (3 mL) is added sodium borohydride (15 mg). The mixture is stirred for two days at room temperature, then concentrated under reduced pressure and purified by column chromatography on silica gel (eluent dichloromethane/methanol/ammonia from 99.5/0.5/0.05 to 99/1/0.1) to give 179 mg of crude base which is dissolved in ethanol (2 mL). A solution of oxalic acid (50 g) in ethanol (1 mL) is added. A white precipitate appears which is filtered, rinsed with diethyl ether and dried under reduced pressure to give 127 mg of 1-{3-[4-(4-hydroxycyclohexyl)phenoxy]propyl}piperidine as a white solid 1H NMR (DMSO): 7.10 (d, 2H, Harom, J=8.6 Hz); 6.80 (d, 2H, Harom, J=8.6 Hz); 3.96 (t, 2H, CH$_2$O); 3.40 (m, 1H, CHOH); 2.90-3.20 (m, 6H, 3 CH$_2$N); 2.40 (m, 1H, CH); 1.15-2.10 (m, 16H, 8CH$_2$).

EXAMPLE 61

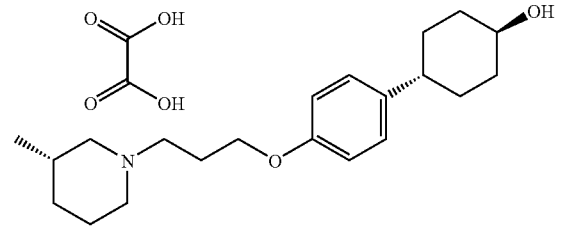

(3S)-1-{3-[trans-4-(4-hydroxycyclohexyl)phenoxy]propyl}-3-methylpiperidine, oxalate

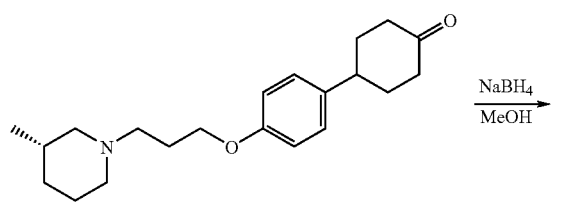

A To a solution of (3S)-1-{3-[4-(4-oxocyclohexyl)phenoxy]propyl}-3-methylpiperidine (170 mg) in methanol (5 mL) is added sodium borohydride (20 mg). The mixture is stirred for one hour at room temperature, and then concentrated under reduced pressure. The residue is partitioned between water (5 mL) and ethyl acetate (10 mL). The aqueous phase is extracted twice with ethyl acetate. The organic extracts are pooled, dried over magnesium sulfate, concentrated under reduced pressure to give 129 mg of crude base which is converted to the oxalate with oxalic acid (35 mg) in a mixture of ethanol and diethyl ether, giving 33 mg of (3S)-1-{3-[trans-4-(4-hydroxycyclohexyl)phenoxy]propyl}-3-methylpiperidine, oxalate as a white powder.

1H NMR (DMSO): 7.10 (d, 2H, Harom, J=8.4 Hz); 6.80 (d, 2H, Harom, J=8.4 Hz); 3.96 (t, 2H, $CH_2O$); 2.60-3.50 (m, 7H, CHOH+3$CH_2$N); 2.35 (m, 1H, CHφ); 0.95-2.15 (m, 15H, 7 $CH_2$+CHCH$_3$); 0.87 (d, 3H, $CH_3$, J=6.3 Hz).

B (3S)-1-{3-[4-(4-oxocyclohexyl)phenoxy]propyl}-3-methylpiperidine can be prepared as follows

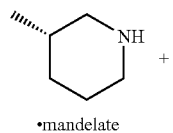

·mandelate

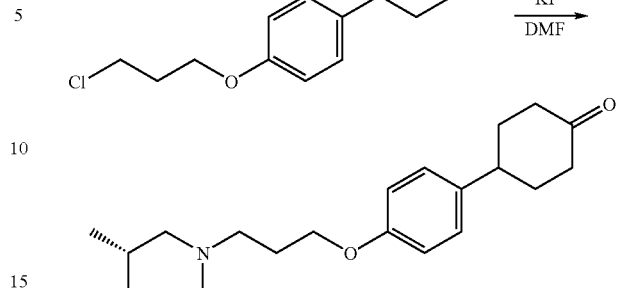

A mixture of (3S)-3-methylpiperidine mandelate (1.57 g), 4-[4-(3-chloropropoxy)phenyl]cyclohexanone (1.33 g), potassium carbonate (2.0 g) and a catalytic amount of potassium iodide in N,N-dimethylformamide (20 mL) is stirred overnight at a temperature close to 100° C., cooled back to room temperature and filtrated. The precipitate is rinsed with ethanol, the filtrate concentrated under reduced pressure and purified by chromatography over silica gel (eluent dichloromethane/methanol from 100/0 to 90/10). Fractions containing the expected product are pooled and concentrated under reduced pressure to give 1.04 g of (3S)-1-{3-[4-(4-oxocyclohexyl)phenoxy]propyl}-3-methylpiperidine as an orange coloured oil used without further purification.

EXAMPLE 62

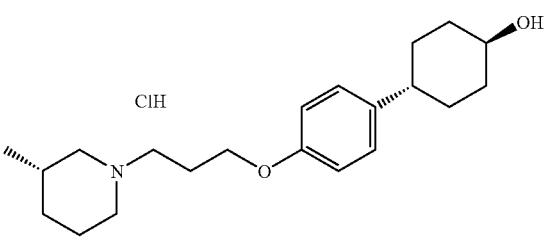

(3S)-1-{3-[4-(4-hydroxycyclohexyl)phenoxy]propyl}-3-methylpiperidine, hydrochloride The crude base is prepared as described in the preparation of the oxalate salt, but is purified by chromatography over silica gel (eluent dichloromethane/methanol from 100/0 to 90/10). Conversion into the hydrochloride is performed by adding a 4M solution of hydrochloric acid in ethyl acetate to a solution of the base in ethyl acetate/ethanol 2/1. The hydrochloride is recrystallized from ethyl acetate/ethanol 2/1 to give (3S)-1-{3-[4-(4-hydroxycyclohexyl)-phenoxy]propyl}-3-methylpiperidine, hydrochloride as a white powder melting at 173° C.

1H NMR (DMSO): 7.10 (d, 2H, Harom, J=8.5 Hz); 6.80 (d, 2H, Harom, J=8.5 Hz); 4.53 (d, 1H, CHOH, J=4.2 Hz); 3.98 (t, 2H, $CH_2O$, J=5.9 Hz); 2.60-3.50 (m, 6H, 3 $CH_2$N); 2.35 (m, 1H, CHφ); 0.90-2.20 (m, 15H, 7 $CH_2$+CHCH$_3$); 0.85 (d, 3H, $CH_3$, J=6.6 Hz).

EXAMPLE 63

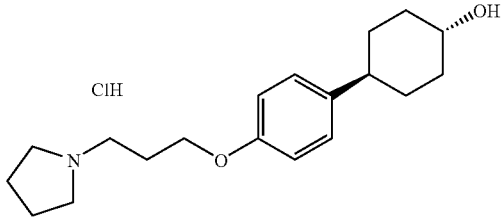

1-{3-[trans-4-(4-hydroxycyclohexyl)phenoxy]
propyl}pyrrolidine, hydrochloride

A Reduction of 1-{3-[4-(4-oxocyclohexyl)phenoxy]
propyl}pyrrolidine (456 mg) as described for (3S)-1-{3-[4-
(4-hydroxycyclohexyl)phenoxy]propyl}-3-methylpiperi-
dine, hydrochloride affords 120 mg of 1-{3-[trans-4-(4-
hydroxycyclo-hexyl)phenoxy]propyl}pyrrolidine,
hydrochloride as a white solid melting at 225° C.

1H NMR (DMSO): 10.6 (bs, 1H, OH); 7.10 (d, 2H, Harom, J=8.3 Hz); 6.80 (d, 2H, Harom, J=8.3 Hz); 4.53 (d, 1H, CHOH, J=3.9 Hz); 3.98 (t, 2H, CH$_2$O, J=5.9 Hz); 2.75-3.60 (m, 6H, 3 CH$_2$N); 2.35 (m, 1H, CHφ); 1.10-2.20 (m, 14H, 7CH$_2$).

B 1-{3-[4-(4-oxocyclohexyl)phenoxy]propyl}pyrrolidine
can be prepared as follows.

Following the procedure described in the preparation of (3S)-1-{3-[4-(4-oxocyclohexyl)phenoxy]propyl}-3-methylpiperidine, but starting from pyrrolidine (427 mg), 4-[4-(3-chloropropoxy)phenyl]cyclohexanone (1.33 g), potassium carbonate (1.38 g) and a catalytic amount of potassium iodide in acetonitrile (25 mL) affords (456 mg) of 1-{3-[4-(4-oxocyclohexyl)phenoxy]propyl}pyrrolidine as a yellow oil used without further purification.

EXAMPLE 64

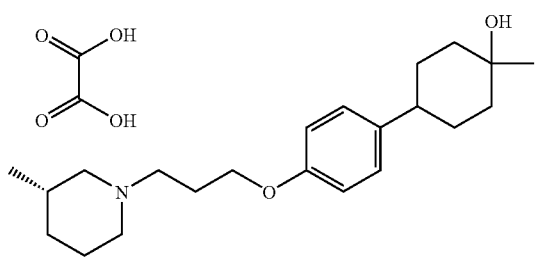

(3S)-1-{3-[4-(4-hydroxy-4-methylcyclohexyl)phenoxy]propyl}-3-methylpiperidine, oxalate

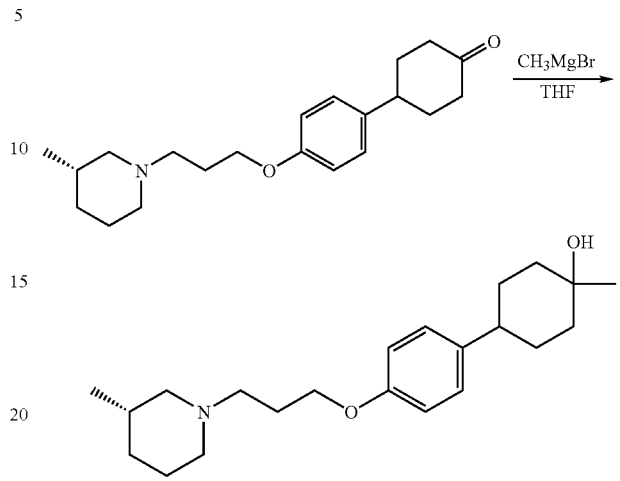

A solution of (3S)-1-{3-[4-(4-oxocyclohexyl)phenoxy]propyl}-3-methylpiperidine (657 mg) in tetrahydrofuran (4 mL) is cooled at a temperature close to 0° C. A solution of methylmagnesium bromide in tetrahydrofuran (22%, 1.6 mL) is added dropwise. The mixture is stirred for two hours at room temperature, and then quenched with a saturated aqueous solution of ammonium chloride. The aqueous phase is extracted with ethyl acetate. The combined extracts are washed with water, dried over magnesium sulfate and concentrated under reduced pressure. The residue is purified by chromatography over silica gel (eluent dichloromethane/methanol from 100/0 to 90/10). A second purification over silica gel (eluent petroleum ether/diethyl ether/triethylamine from 50/50/1 to 0/100/4) followed by salt formation with oxalic acid, affords (3S)-1-{3-[4-(4-hydroxy-4-methylcyclohexyl)phenoxy]propyl}-3-methylpiperidine, oxalate as a white powder.

1H NMR (DMSO): 7.08-7.15 (2d, 2H, Harom); 6.80 (d, 2H, Harom, J=8.5 Hz); 3.96 (t, 2H, CH$_2$O, J=5.9 Hz); 2.60-3.45 (m, 6H, 3 CH$_2$N); 2.35 (m, 1H, CHφ); 0.90-2.20 (m, 18H, 7 CH$_2$+CH$_3$+CHCH$_3$); 0.86 (d, 3H, CH$_3$, J=6.5 Hz).

EXAMPLE 65

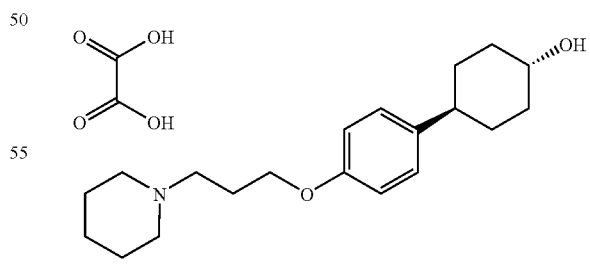

1-{3-[trans-4-(4-hydroxycyclohexyl)phenoxy]
propyl}piperidine, oxalate

Reduction of 1-{3-[-4-(4-oxocyclohexyl)phenoxy]propyl}piperidine (1.57 g) as described for (3S)-1-{3-[trans-4-(4-hydroxycyclohexyl)phenoxy]propyl}-3-methyl-piperidine gives 600 mg of 1-{3-[trans-4-(4-hydroxycyclohexyl)phenoxy]-propyl}piperidine, oxalate as a white powder melting at 182° C.

1H NMR (DMSO): 7.10 (d, 2H, Harom, J=8.4 Hz); 6.80 (d, 2H, Harom, J=8.4 Hz); 3.97 (t, 2H, CH$_2$O); 3.41 (m, 1H, CHOH); 2.95-3.20 (m, 6H, 3 CH$_2$N); 2.40 (m, 1H, CHφ); 1.15-2.10 (m, 16H, 8CH$_2$).

EXAMPLE 66

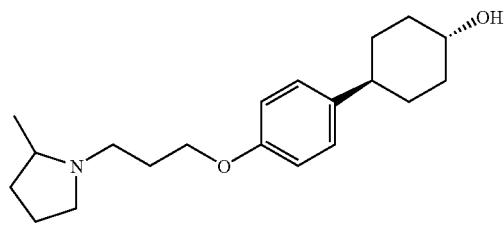

1-{3-[trans-4-(4-hydroxycyclohexyl)phenoxy]propyl}-2-methylpyrrolidine, oxalate

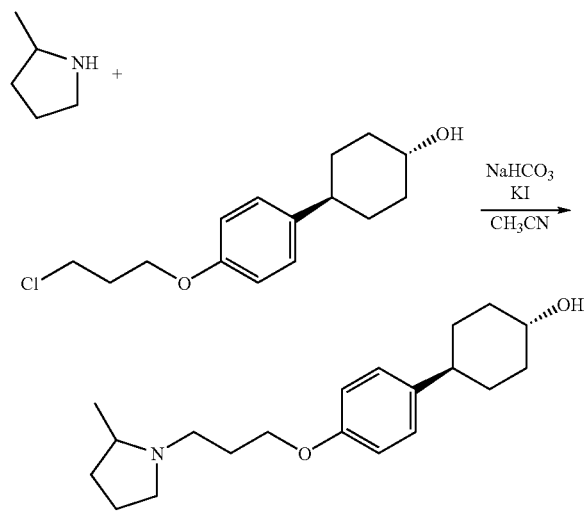

A A mixture of trans-4-[4-(3-chloropropoxy)phenyl]cyclohexanol (403 mg), sodium hydrogenocarbonate (252 mg) potassium iodide (10 mg) and 2-methylpyrrolidine (153 mg) in acetonitrile (10 mL) is heated for 24 hours under reflux, then concentrated under reduced pressure. The residue is dissolved in ethyl acetate (25 mL). The organic phase is washed with water (5 mL), dried over magnesium sulfate, concentrated under reduced pressure and purified by chromatography over silica gel (eluent dichloromethane/methanol from 98/2 to 90/10). Fractions containing the expected product are pooled and concentrated under reduced pressure to give 120 mg of 1-{3-[trans-4-(4-hydroxycyclohexyl)phenoxy]propyl}-2-methylpyrrolidine as a white solid melting at 80° C.

1H NMR of the free base (CDCl$_3$): 7.11 (d, 2H, Harom, J=8.6 Hz); 6.83 (d, 2H, Harom, J=8.6 Hz); 4.02 (t, 2H, CH$_2$O); 3.68 (m, 1H, CHN); 3.49 (m, 1H, CHN); 3.00 (m, 1H, CHN); 1.20-2.60 (m, 18H); 1.10 (d, 3H, CH$_3$, J=6.1 Hz).

B trans-4-[4-(3-chloropropoxy)phenyl]cyclohexanol can be prepared as follows.

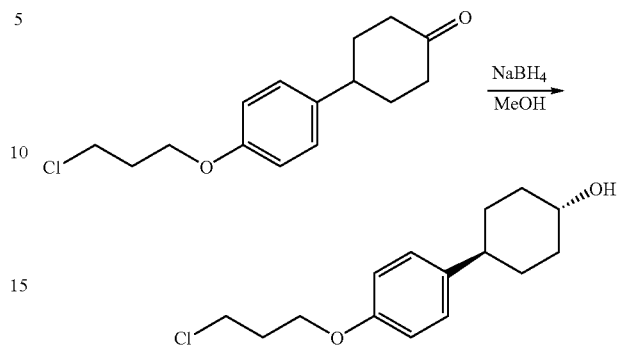

A solution of 4-[4-(3-chloropropoxy)phenyl]cyclohexanone (800 mg) in methanol (10 mL) is cooled to a temperature close to 0° C. Sodium borohydride (57 mg) is added and the mixture stirred for one hour at room temperature, then concentrated under reduced pressure. Water (15 mL) is added and the insoluble separated by filtration, rinsed with diethyl ether and dried under reduced pressure to give 550 mg of trans-4-[4-(3-chloropropoxy)phenyl]cyclohexanol as a white solid used without further purification.

EXAMPLE 67

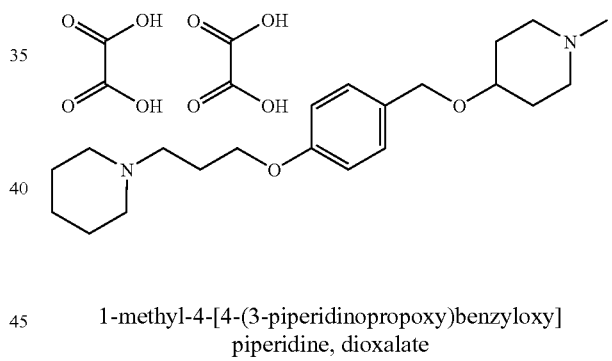

1-methyl-4-[4-(3-piperidinopropoxy)benzyloxy]piperidine, dioxalate

A A 60% suspension of sodium hydride in oil (168 mg) is degreased by pentane washings. A solution of 4-hydroxy-1-methylpiperidine (164.5 mg) in tetrahydrofuran (2 mL) is added. The mixture is stirred at room temperature for two hours, then a solution of 1-[3-(4-chloromethylphenoxy)propyl]piperidine (456.6 mg) in tetrahydrofuran (3 mL) is added. The mixture is stirred at room temperature for 16 hours, then hydrolyzed by addition of water and extracted with dichloromethane. The organic extracts are pooled, dried over magnesium sulphate and concentrated under reduced pressure. The residue is purified by chromatography over silica gel (eluent: dichloromethane/methanol/ammonia 80/20/0.5). Fractions containing the expected product are pooled and concentrated under reduced pressure to give 71 mg of the crude base which is converted to the hygroscopic dioxalate.

$^1$H NMR (DMSO): 7.24 (d, 2H, Harom., J=8.3 Hz); 6.88 (d, 2H, Harom., J=8.3 Hz); 4.39 (s, 2H, φCH$_2$O); 3.98 (t, 2H, CH$_2$O, J=5.9 Hz); 3.54 (m, 1H, CHO); 2.8-3.2 (m, 10H, 5 CH$_2$N); 2.60 (s, 3H, CH$_3$N); 1.73-2.07 (m, 6H, 3CH$_2$); 1.2-1.6 (m, 6H, 3CH$_2$).

B 1-[3-(4-chloromethylphenoxy)propyl]piperidine can be prepared as follows

To a solution of 1-[3-(4-hydroxymethylphenoxy)propyl] piperidine (5.617 g) in dichloromethane (50 mL), cooled at a temperature close to 0° C., is added dropwise thionyl chloride (3 mL). The mixture is stirred for 18 hours at room temperature and concentrated under reduced pressure. The residue is crystallized in diethyl ether to give 1-[3-(4-chloromethylphenoxy)propyl]piperidine as an off white solid used without further purification.

C 1-[3-(4-hydroxymethylphenoxy)propyl]piperidine can be prepared as follows

A mixture of 4-(3-chloropropoxy)benzyl alcohol (11.1 g), potassium carbonate (23.0 g), piperidine (6.57 mL) and N,N-dimethylformamide (130 mL) is heated at a temperature close to 100° C. for 5 h30, then cooled back to room temperature. Water (130 mL) is added and organics are extracted with dichloromethane. The combined extracts are pooled, dried over magnesium sulphate, purified by chromatography over silica gel (eluent: dichloromethane/methanol with trace amount of ammonia from 90/10 to 80/20) to give 5.62 g of 1-[3-(4-hydroxymethylphenoxy)-propyl]piperidine, hydrochloride as a white solid used without further purification.

D 4-(3-chloropropoxy)benzyl alcohol can be prepared as follows

To a solution of 4-(3-chloropropoxy)benzaldehyde (30 g) in methanol (250 mL), cooled at a temperature close to 0° C., is added portionwise sodium borohydride (7.72 g). The mixture is stirred for 4 hours, hydrolysed with a saturated aqueous solution of ammonium chloride and extracted with diethyl ether. The combined extracts are dried over magnesium sulphate, concentrated under reduced pressure and purified by chromatography over silica gel (eluent: dichloromethane/methanol from 100/0 to 95/5). Fractions containing the expected product are pooled and concentrated under reduced pressure to give 11.1 g of 4-(3-chloropropoxy)benzyl alcohol as a white solid used without further purification.

4-(3-chloropropoxy)benzaldehyde is described in U.S. Pat. No. 2,797,242 (1953 to Parke Davis)

EXAMPLE 68

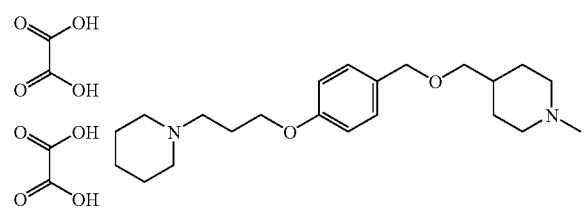

1-methyl-4-[4-(3-piperidinopropoxy)benzyloxymethyl]piperidine, dioxalate

A mixture of 4-hydroxymethyl-1-methylpiperidine (180.9 mg), potassium tert-butylate (4.56 mL of a 0.92M solution in tetrahydrofuran) and tetrahydrofuran (3 mL) is stirred for one hour at room temperature. A solution of 1-[3-(4-chloromethylphenoxy)propyl]piperidine (456.4 mg) in tetrahydrofuran (3 mL) is added. The mixture is stirred at room temperature for 65 hours, then hydrolyzed by addition of water and extracted with dichloromethane. The organic extracts are pooled, dired over magnesium sulphate and concentrated under reduced pressure. The residue is purified by chromatography over silica gel (eluent: dichloromethane/methanol/ammonia 95/5/0.5). Fractions containing the expected product are pooled and concentrated under reduced pressure to give 132 mg of the crude base which is converted to the dioxalate as a white powder melting at 151° C.

$^1$H NMR (DMSO): 7.21 (d, 2H, Harom., J=8.2 Hz); 6.88 (d, 2H, Harom., J=8.2 Hz); 4.35 (s, 2H, φCH$_2$O); 3.98 (t, 2H, CH$_2$O, J=6.1 Hz); 2.7-3.3 (m, 11H, CHO+5 CH$_2$N); 2.64 (s, 3H, CH$_3$N); 1.2-2.1 (m, 12H, 6CH$_2$).

EXAMPLE 69

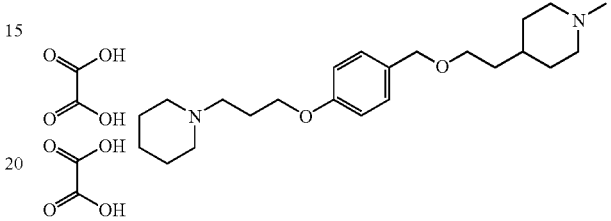

1-methyl-4-{2-[4-(3-piperidinopropoxy)benzyloxy]ethyl}piperidine, dioxalate

A mixture of 4-(2-hydroxyethyl)-1-methylpiperidine (200.5 mg), potassium tert-butylate (4.56 mL of a 0.92M solution in tetrahydrofuran) and tetrahydrofuran (3 mL) is stirred for one hour at room temperature. A solution of 1-[3-(4-chloromethylphenoxy)propyl]piperidine (456.4 mg) in tetrahydrofuran (3 mL) is added. The mixture is stirred at room temperature for 18 hours, then hydrolyzed by addition of water and extracted with dichloromethane. The organic extracts are pooled, dried over magnesium sulphate and concentrated under reduced pressure. The residue is purified by chromatography over silica gel (eluent: dichloromethane/methanol/ammonia from 951510.5 to 90/10/0.5). Fractions containing the expected product are pooled and concentrated under reduced pressure to give 168 mg of the crude base which is converted to the dioxalate as a white powder melting at 106° C.

$^1$H NMR (DMSO): 7.20 (d, 2H, Harom., J=8.3 Hz); 6.87 (d, 2H, Harom., J=8.3 Hz); 4.33 (s, 2H, φCH$_2$O); 3.98 (t, 2H, CH$_2$O, J=6.0 Hz); 3.42 (t, 2H, CH$_2$O, J=6.1 Hz); 2.7-3.3 (m, 10H, 5 CH$_2$N); 2.64 (s, 3H, CH$_3$N); 2.04 (m, 2H, CH$_2$); 1.2-1.8 (m, 13H, CH+6CH$_2$).

EXAMPLE 70

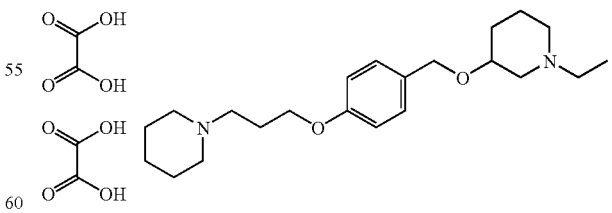

1-ethyl-3-[4-(3-piperidinopropoxy)benzyloxy]piperidine, dioxalate

A 60% suspension of sodium hydride in oil (168 mg) is degreased by pentane washings. A solution of 3-hydroxy-1- ethylpiperidine (185 mg) in tetrahydrofuran (2 mL) is added. The mixture is stirred at room temperature for two hours, then a solution of 1-[3-(4-chloromethylphenoxy)propyl]piperidine (456.6 mg) in tetrahydrofuran (3 mL) is added. The mixture is stirred at room temperature for 19 hours, potassium tert-butylate (5 mL of a 0.92M solution in tetrahydrofuran) is added. The mixture is stirred at room temperature for 24 hours, then hydrolyzed by addition of water and extracted with dichloromethane. The organic extracts are pooled, dried over magnesium sulphate and concentrated under reduced pressure. The residue is purified by chromatography over silica gel (eluent: dichloromethane/methanol/ammonia 90/10/0.5). Fractions containing the expected product are pooled and concentrated under reduced pressure to give 135 mg of the crude base which is converted to the dioxalate as a white powder melting at 178° C.

$^1$H NMR (DMSO): 7.25 (d, 2H, Harom., J=8.4 Hz); 6.88 (d, 2H, Harom., J=8.4 Hz); 4.45 (s, 2H, $\phi$CH$_2$O); 3.99 (t, 2H, CH$_2$O, J=5.9 Hz); 3.67 (m, 1H, CHO); 2.8-3.3 (m, 12H, 5CH$_2$N); 2.04 (m, 2H, CH$_2$); 1.3-1.9 (m, 10H, 3CH$_2$); 1.15 (t, 3H, CH$_3$).

EXAMPLE 71

H3 Binding

Membranes expressing human histamine H3 receptors were incubated 1 hour at room temperature in binding buffer containing 50 mM Na$_2$HPO$_4$/KH$_2$PO$_4$ pH 7.5 in a final volume of 200 μl. For binding experiments [$^{125}$I]iodoproxyfan (2000 Ci/mmol; Amersham Pharmacia Biotech) concentrations ranged between 20 and 40 pM. Non-specific binding was determined in the presence of 1 μM Imetit. The reaction was stopped by rapid filtration through GF/B filters (pre-soaked for 2 hours with 0.3% polyethyleneimine) followed by 3 ice cold binding buffer washes. The filter-bound radioactivity was measured in a liquid scintillation counter with 50 μl of scintillation fluid.

The hH$_3$ binding investigated by use of [$^{125}$I]iodoproxyfan gives a Kd=78±6 pM.

Representative affinities for the compounds of the invention are given in the table below:

| Example nb° | Ki (nM) |
|---|---|
| 1 | 2.9 |
| 3 | 1.1 |
| 7 | 0.74 |
| 8 | 0.82 |

| Example nb° | Ki (nM) |
|---|---|
| 17 | 0.43 |
| 18 isomer A | 0.3 |
| 18 isomer B | 0.21 |
| 24 | 3.5 |
| 28 | 0.53 |
| 29 | 0.88 |
| 32 | 0.22 |
| 35 | 0.1 |
| 41 | 0.13 |
| 54 | 0.4 |
| 58 | 0.061 |
| 62 | 0.554 |
| 66 | 0.83 |
| 69 | 1.19 |
| 70 | 0.35 |

EXAMPLE 72

Cytochrome Inhibition

Cytochromes P-450 (Cyps) Comprise a Superfamily of Hemoproteins that Play an important role in the metabolism of a wide variety of xenobiotics and endogenous compounds. Among the xenobiotic-metabolizing CYPs, five forms, CYP1A2, CYP2C9, CYP2C19, CYP2D6 and CYP3A4 appear to be the major CYP isoforms responsible for the oxidative metabolism of drugs or xenobiotics. Inhibition of CYP-mediated metabolism, often the mechanism for drug-drug interactions, can limit the use of a drug because of adverse clinical effects. The potential for CYP enzyme inhibition is routinely assessed by performing in vitro inhibition studies by measuring the rates of metabolism of a probe biotransformation in the presence and absence of test molecules.

The ability of drug in human to inhibit the catalytic activity of cytochrome P-450 isoforms was assayed using microtiter plate-based, fluorometric assays for the activities of the five human major CYP forms. Inhibition potential was determined in vitro after incubation of fluorescent model substrates over various incubation time with human recombinant cytochrome isoforms in the absence or in presence of increasing concentrations of test molecules (from 1 nM to 100 μM), in comparison with specific CYP isoform inhibitors. Data were expressed as quantitative inhibition parameters [inhibitor concentration that produces 50% inhibition (IC$_{50}$ value)].

Incubation of drug was carried out at 37° C.±0.5° C. under agitation in the presence of human recombinant cytochrome P-450 isoforms and a NADPH generating system. The incubation conditions for each cytochrome isoform were as follows:

| | Cytochrome P-450 Enzyme | | | | |
|---|---|---|---|---|---|
| | CYP1A2 | CYP2C9 | CYP2C19 | CYP2D6 | CYP3A4 |
| | NADPH Regenerating System | | | | |
| NADP+ | 1.3 mM | 1.3 mM | 1.3 mM | 8.2 μM | 1.3 mM |
| Glucose-6-Phosphate | 3.3 mM | 3.3 mM | 3.3 mM | 0.41 mM | 3.3 mM |
| Magnesium Chloride Hexahydrate | 3.3 mM | 3.3 mM | 3.3 mM | 0.41 mM | 3.3 mM |

-continued

| | Cytochrome P-450 Enzyme | | | | |
|---|---|---|---|---|---|
| | CYP1A2 | CYP2C9 | CYP2C19 | CYP2D6 | CYP3A4 |
| Glucose-6-Phosphate Dehydrogenase | 0.4 Units/mL | 0.4 Units/mL | 0.4 Units/mL | 0.4 Units/mL | 0.4 Units/mL |
| | | | Other Reagents | | |
| $KPO_4$ buffer pH 7.4 | 100 mM | 25 mM | 50 mM | 100 mM | 200 mM |
| Positive Control (highest concentration) | Furafylline 100 μM | Sulfaphenazole 10 μM | Nootkatone 100 μM | Quinidine 10 μM | Ketoconazole 10 μM |
| Substrate | CEC 5 μM | MFC 75 μM | O-MF 2 μM | AMMC 1.5 μM | BFC 50 μM |
| Enzyme: recombinant CYP | 0.5 pmol | 1.0 pmol | 1.0 pmol | 1.5 pmol | 1.0 pmol |

CEC: 7-ethoxy-3-cyanocoumarin
MFC: 7-Methoxy-4-(trifluoromethyl)-coumarin
O-MF: 3-O-methyl fluorescein
AMMC: 3-[2-(N,N-diethyl-N-methylamino)ethyl]-7-methoxy-4-methylcoumarin
BFC: 7-Benzyloxy-4-(trifluoromethyl)-coumarin Representative cytochrome inhibition (IC50, concentrations in μM for 50% inhibition) for the compounds of the invention are given in the table below:

| N° | CYP3A4 | CYP2D6 |
|---|---|---|
| 1 | 32 | >10 |
| 2 | >10 | >10 |
| 3 | 18 | 32 |
| 4 | >10 | >10 |
| 5 | 67 | >10 |
| 6 | >10 | >10 |
| 7 | 4 | 39 |
| 8 | 20 | >100 |
| 9 | 3 | 8 |
| 10 | 30 | 47 |
| 11 | 20 | 5 |
| 12 | 28 | >10 |
| 13 | 16 | 23 |
| 14 | >10 | >10 |
| 15 | 46 | >10 |
| 16 | 22 | >100 |
| 17 | >100 | >100 |
| 18 | 43 | >10 |
| 18 | 50 | >10 |
| 19 | 42 | >10 |
| 19 | 48 | >10 |
| 20 | 38 | >10 |
| 20 | 35 | >10 |
| 21 | >10 | >10 |
| 22 | 3 | 13 |
| 23 | 3 | 13 |
| 24 | >10 | >10 |
| 25 | >10 | >10 |
| 26 | 8 | 14 |
| 27 | >1 | >10 |
| 28 | 10 | 10 |
| 29 | >100 | 24 |
| 30 | 11 | 7 |
| 31 | 4 | 4 |
| 32 | 9 | 7 |
| 33 | 7 | 3 |
| 34 | 10 | 20 |
| 35 | 5 | 71 |
| 36 | 3 | >10 |
| 37 | 15 | >10 |
| 38 | 30 | >10 |
| 39 | 11 | 6 |
| 40 | 66 | >100 |
| 41 | >1 | >10 |

-continued

| N° | CYP3A4 | CYP2D6 |
|---|---|---|
| 41 | 13 | 14 |
| 42 | >10 | >10 |
| 43 | >10 | >1 |
| 44 | >1 | >10 |
| 45 | 5 | 79 |
| 46 | 12 | >100 |
| 47 | 37 | 107 |
| 48 | 2 | 2 |
| 49 | 27 | >10 |
| 51 | 72 | >100 |
| 53 | 57 | 64 |
| 54 | >1 | >10 |
| 55 | >10 | >10 |
| 56 | >1 | >10 |
| 57 | >10 | >10 |
| 58 | >10 | >10 |
| 59 | >10 | >10 |
| 60 | >10 | >10 |
| 61 | >10 | >10 |
| 62 | >10 | >10 |
| 63 | >10 | >10 |
| 64 | >10 | >10 |
| 65 | >10 | >10 |
| 66 | >10 | >10 |
| 67 | >10 | >10 |
| 68 | >10 | >10 |
| 69 | >10 | >10 |

EXAMPLE 73

Comparative Examples

Representative affinity and cytochrome inhibition (IC50, concentrations for 50% inhibition) for the compounds of WO 00/06254 are given in the table below.

| Example nb° | Ki (nM) | CYP3A4 | CYP2D6 |
|---|---|---|---|
| 59 | 6.9 | >1 μM | 1 μM |
| 74 | 4.5 | 1 μM | 1 μM |
| 111 | 14 | >1 μM | 1 μM |
| 117 | 2.4 | 13 μM | 0.059 μM |
| 161 | 0.53 | 52% @ 1 μM | 67% @ 1 μM |

It is apparent that the compounds of the invention surprisingly exhibit reduced cytochrome inhibition (higher IC50) and/or improved affinity (lower Ki).

The invention claimed is:

1. A compound of formula (I):

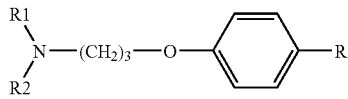

wherein R1 and R2 taken together with the nitrogen atom to which they are attached, form a mono or bicyclic saturated nitrogen-containing ring of formula:

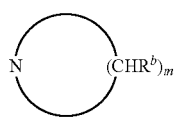

with m=4 or 5, each Rb is independently identical or different, and Rb is a hydrogen or a $C_1$-$C_4$ alkyl, or 2 Rb form together a bond so as to form a bicyclic ring, chosen from:

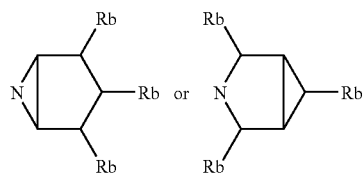

R is chosen from:
a) a pyridyl group, or a cycloalkyl, each optionally substituted with one or more of Halogen atom, C1-C4 alkyl, O—C1-C4 alkyl, OH, or NR3R4; and where the N atom within the pyridyl ring may be in the form of N-Oxide ($N^+$—$O^-$), or bicyclic aryl substituted with one or more of Halogen atom, C1-C4 alkyl, O—C1-C4 alkyl, OH, NR3R4, —$C_2$-$C_4$ alkenyl or —C2-C4 alkynyl, where alkyl, alkenyl or alkynyl is optionally substituted with a heterocycle, or NR3R4;

wherein R3, R4 are independently hydrogen, a straight or branched $C_1$-$C_4$ alkyl or an aryl group or taken together with the nitrogen atom to which they are attached form a saturated or partially unsaturated monocyclic or bicyclic heterocycle or heteroaryl optionally comprising one or more further heteroatoms and/or optionally substituted with one or more of Halogen atom, C1-C4 alkyl, O—C1-C4 alkyl or OH;

or their pharmaceutically acceptable salts, or their optical isomers, racemates, diastereomers or enantiomers.

2. Compound according to claim 1, wherein in a), where R is naphthyl, then at least one of Rb is a $C_1$-$C_4$ alkyl.

3. Compound according to claim 1, wherein R1 and R2 form together with the nitrogen atom to which they are attached a mono saturated nitrogen-containing ring of formula:

with m=4 or 5, each Rb is independently identical or different and is a hydrogen or a $C_1$-$C_4$ alkyl;

R is chosen from:
a) a pyridyl group, or cycloalkyl, each optionally substituted with one or more of Halogen atom, C1-C4 alkyl, O—C1-C4 alkyl, OH or NR3R4 and where the N atom within the pyridyl ring may be in the form of N-Oxide ($N^+$—$O^-$), or bicyclic aryl substituted with one or more of Halogen atom, C1-C4 alkyl, O—C1-C4 alkyl, OH, NR3R4, —C2-C4 alkenyl or —C2-C4 alkynyl, where alkyl, alkenyl or alkynyl is optionally substituted with a heterocycle, or NR3R4;

wherein R3, R4 are independently hydrogen, a straight or branched $C_1$-$C_4$ alkyl or an aryl group or taken together with the nitrogen atom to which they are attached form a saturated or partially unsaturated monocyclic or bicyclic heterocycle or heteroaryl optionally substituted with one or more of Halogen atom, C1-C4 alkyl, O—C1-C4 alkyl, or OH;

or their pharmaceutically acceptable salts, or their optical isomers, racemates, diastereomers or enantiomers.

4. Compound according to claim 1, wherein R1 and R2 form together with the nitrogen atom to which they are attached a mono saturated nitrogen-containing ring of formula:

with m=4 or 5, each Rb is independently identical or different is a hydrogen or a $C_1$-$C_4$ alkyl;

R is chosen from:
a) a pyridyl group, or cycloalkyl, each optionally substituted with one or more of halogen atom, C1-C4 alkyl, O—C1-C4 alkyl, OH, or NR3R4 and where the N atom within the pyridyl ring may be in the form of N-Oxide ($N^+$—$O^-$), or where alkyl, alkenyl or alkynyl is optionally substituted with a heterocycle or NR3R4 wherein R3, R4 are independently hydrogen, a straight or branched $C_1$-$C_4$ alkyl or an aryl group or taken together with the nitrogen atom to which they are attached form a saturated or partially unsaturated monocyclic or bicyclic heterocycle or heteroaryl optionally substituted with one or more of Halogen atom, C1-C4 alkyl, O—C1-C4 alkyl or OH;

or their pharmaceutically acceptable salts, or their optical isomers, racemates, diastereomers or enantiomers.

5. Compound according to claim 1, wherein R is chosen from:
a pyridyl group, where the N-atom is optionally in the form of N-Oxide ($N^+$—$O^-$), and said pyridyl being optionally substituted with one or more of halogen atom or C1-C4 alkyl;

where alkyl, alkenyl or alkynyl is optionally substituted with a heterocycle or NR3R4.

6. Compound according to claim 1 chosen from:
(3S,5S)-1-{3-[4-(trans-4-dimethylaminocyclohex-1-yl)phenoxy]propyl}-3,5-dimethylpiperidine,
1-{3-[4-(cis-4-dimethylaminocyclohex-1-yl)phenoxy]propyl}piperidine,
1-{3-[4-(trans-4-dimethylaminocyclohex-1-yl)phenoxy]propyl}piperidine,
1-{3-[4-(cis-4-tetramethylenaminocyclohex-1-yl)phenoxy]propyl}piperidine,
1-{3-[4-(trans-4-tetramethylenaminocyclohex-1-yl)phenoxy]-propyl}piperidine,
trans-1-{3-[4-(cis-4-dimethylaminocyclohex-1-yl)phenoxy]propyl}-3,5-dimethylpiperidine,
trans-1-{3-[4-(trans-4-dimethylaminocyclohex-1-yl)phenoxy]propyl}-3,5-dimethylpiperidine,
1-{[3-{4-(4-pyridyl)phenoxy]propyl}piperidine,
trans-3,5-dimethyl-1-{3-[4-(4-pyridyl)phenoxy]propyl}piperidine,
1-{3-[4-(3-pyridyl)phenoxy]propyl}piperidine,
(3S,5S)-1-{3-[4-(trans-4-dimethylaminocyclohex-1-yl)phenoxy]propyl}-3,5-dimethylpiperidine,
(3S)-1-{3-[4-(trans-4-dimethylaminocyclohex-1-yl)phenoxy]propyl}-3-methylpiperidine,
(3S)-3-methyl-1-{3-[4-(4-pyridyl)phenoxy]propyl}piperidine,
1-(3-{[4'-(piperidinomethyl)biphenyl-4-yl]oxy}propyl)piperidine,
(3S,5S)-1-{3-[4-(trans-4-morpholinocyclohex-1-yl)phenoxy]propyl}-3,5-dimethylpiperidine,
(3S)-1-{3-[4-(trans-4-morpholinocyclohex-1-yl)phenoxy]propyl}-3-methylpiperidine,
1-{3-[4-(trans-4-morpholinocyclohex-1-yl)phenoxy]propyl}piperidine,
1-{3-[4-(cis-4-morpholinocyclohex-1-yl)phenoxy]propyl}piperidine,dihydrochloride,
1-{3-[4-(trans-4-morpholinocyclohex-1-yl)phenoxy]propyl}piperidine,dihydrochloride,
(3S)-3-methyl-1-{3-[4-(cis-4-morpholinocyclohex-1-yl)phenoxy]propyl}piperidine,dihydrochloride,
(3S)-3-methyl-1-{3-[4-(trans-4-morpholinocyclohex-1-yl)phenoxy]propyl}piperidine,dihydrochloride,
(3S,5S)-1-{3-[4-(trans-4-aminocyclohex-1-yl)phenoxy]propyl}-3,5-dimethylpiperidine,
(3S)-4-{4-[3-(3-methylpiperidin-1-yl)propoxy]phenyl}pyridine 1-oxide,
4-[4-(3-piperidinopropoxy)phenyl]pyridine 1-oxide,
2-methyl-4-(4-{3-[(3S)-3-methylpiperidin-1-yl]propoxy}phenyl)pyridine 1-oxide,
2-hydroxy-4-(4-{3-[(3S)-3-methylpiperidin-1-yl]propoxy}phenyl)pyridine,
1-methyl-4-(4-{3-[(3S)-3-methylpiperidin-1-yl]propoxy}phenyl)pyridinium,
2-(3-piperidinopropoxy)-4-(4-{3-[(3S)-3-methylpiperidin-1-yl]propoxy}phenyl)pyridine,
2-methyl-4-(4-{3-[(3S)-3-methylpiperidin-1-yl]propoxy}phenyl)pyridine,
1-{3-[4-(4-hydroxycyclohexyl)phenoxy]propyl}piperidine,
(3S)-1-{3-[trans-4-(4-hydroxycyclohexyl)phenoxy]propyl}-3-methylpiperidine,
(3S)-1-{3-[4-(4-hydroxycyclohexyl)phenoxy]propyl}-3-methylpiperidine,
1-{3-[trans-4-(4-hydroxycyclohexyl)phenoxy]propyl}pyrrolidine,
(3S)-1-{3-[4-(4-hydroxy-4-methylcyclohexyl)phenoxy]propyl}-3-methylpiperidine,
1-{3-[trans-4-(4-hydroxycyclohexyl)phenoxy]propyl}pyrrolidine, or
1-{3-[trans-4-(4-hydroxycyclohexyl)phenoxy]propyl}-2-methylpyrrolidine, or their pharmaceutically acceptable salts, or their optical isomers, racemates, diastereomers or enantiomers.

7. Compound according to claim 1 chosen from:
(3S,5S)-1-{3-[4-(trans-4-dimethylaminocyclohex-1-yl)phenoxy]propyl}-3,5-dimethylpiperidine,
1-{3-[4-(cis-4-dimethylaminocyclohex-1-yl)phenoxy]propyl}piperidine,
1-{3-[4-(trans-4-dimethylaminocyclohex-1-yl)phenoxy]propyl}-piperidine,
1-{3-[4-(cis-4-tetramethylenaminocyclohex-1-yl)phenoxy]propyl}piperidine,
1-{3-[4-(trans-4-tetramethylenaminocyclohex-1-yl)phenoxy]propyl}-piperidine,
trans-1-{3-[4-(cis-4-dimethylaminocyclohex-1-yl)phenoxy]propyl}-3,5-dimethylpiperidine,
trans-1-{3-[4-(trans-4-dimethylaminocyclohex-1-yl)phenoxy]propyl}-3,5-dimethylpiperidine,
1-{[3-{4-(4-pyridyl)phenoxy]propyl}piperidine,
trans-3,5-dimethyl-1-{3-[4-(4-pyridyl)phenoxy]propyl}piperidine,
1-{3-[4-(3-pyridyl)phenoxy]propyl}piperidine,
(3S)-3-methyl-1-{3-[4-(4-pyridyl)phenoxy]propyl}piperidine,
1-{3-[4-(cis-4-morpholinocyclohex-1-yl)phenoxy]propyl}piperidine,
1-{3-[4-(trans-4-morpholinocyclohex-1-yl)phenoxy]propyl}piperidine,
(3S)-3-methyl-1-{3-[4-(cis-4-morpholinocyclohex-1-yl)phenoxy]propyl}piperidine,
(3S)-3-methyl-1-{3-[4-(trans-4-morpholinocyclohex-1-yl)phenoxy]propyl}piperidine,
(3S)-4-{4-[3-(3-methylpiperidine-1-yl)propoxy]phenyl}pyridine 1-oxide,
(3S)-1-{3-[trans-4-(4-hydroxycyclohexyl)phenoxy]propyl}-3-methylpiperidine, or
(3S)-1-{3-[4-(4-hydroxycyclohexyl)phenoxy]propyl}-3-methylpiperidine, or their pharmaceutically acceptable salts, or their optical isomers, racemates, diastereomers or enantiomers.

8. Compound according to claim 1 chosen from:
1-{3-[4-(cis-4-dimethylaminocyclohex-1-yl)phenoxy]propyl}piperidine,
1-{3-[4-(trans-4-dimethylaminocyclohex-1-yl)phenoxy]propyl}-piperidine,
1-{3-[4-(cis-4-tetramethylenaminocyclohex-1-yl)phenoxy]propyl}piperidine,
1-{3-[4-(trans-4-tetramethylenaminocyclohex-1-yl)phenoxy]propyl}-piperidine,
trans-1-{3-[4-(cis-4-dimethylaminocyclohex-1-yl)phenoxy]propyl}-3,5-dimethylpiperidine,
trans-1-{3-[4-(trans-4-dimethylaminocyclohex-1-yl)phenoxy]propyl}-3,5-dimethylpiperidine,
1-{[3-{4-(4-pyridyl)phenoxy]propyl}piperidine,
trans-3,5-dimethyl-1-{3-[4-(4-pyridyl)phenoxy]propyl}piperidine,
1-{3-[4-(3-pyridyl)phenoxy]propyl}piperidine,
trans-3,5-dimethyl-1-{3-[4-(pyrazol-3-yl)phenoxy]propyl}piperidine,
(3S)-3-methyl-1-{3-[4-(4-pyridyl)phenoxy]propyl}piperidine, 1-{3-[4-(cis-4-morpholinocyclohex-1-yl)phenoxy]
propyl}piperidine,
1-{3-[4-(trans-4-morpholinocyclohex-1-yl)phenoxy]
propyl}piperidine,
(3S)-3-methyl-1-{3-[4-(cis-4-morpholinocyclohex-1-yl)
phenoxy]propyl}piperidine,
(3S)-3-methyl-1-{3-[4-(trans-4-morpholinocyclohex-1-
yl)phenoxy]propyl}piperidine,
(3S)-4-{4-[3-(3-methylpiperidin-1-yl)propoxy]
phenyl}pyridine 1-oxide,
(3S)-1-{3-[trans-4-(4-hydroxycyclohexyl)phenoxy]pro-
pyl}-3-methylpiperidine,
(3S)-1-{3-[4-(4-hydroxycyclohexyl)phenoxy]propyl}-3-
methylpiperidine, or
or their pharmaceutically acceptable salts, or their optical
isomers, racemates, diastereomers or enantiomers.
  9. Compound according to claim 1 chosen from:
  (3S)-3-methyl-1-{3-[4-(4-pyridyl)phenoxy]
propyl}piperidine,dioxalate,
  (3S)-4-{4-[3-(3-methylpiperidin-1-yl)propoxy]
phenyl}pyridine 1-oxide, oxalate,
  (3S)-4-{4-[3-(3-methylpiperidin-1-yl)propoxy]
phenyl}pyridine 1-oxide, hydrochloride, or
  (3S)-4-{4-[3-(3-methylpiperidin-1-yl)propoxy]
phenyl}pyridine 1-oxide, dihydrochloride.
  10. Compound according to claim 3, wherein the aryl is naphthyl.
  11. A compound of formula (I):

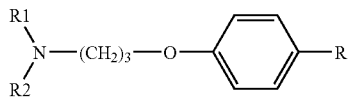

wherein R1 and R2 taken together with the nitrogen atom to which they are attached, form a mono or bicyclic saturated nitrogen-containing ring of formula:

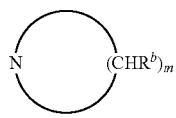

with m=4 or 5, each Rb is independently identical or different, and Rb is a hydrogen or a $C_1$-$C_4$ alkyl, or 2 Rb form together a bond so as to form a bicyclic ring, chosen from:

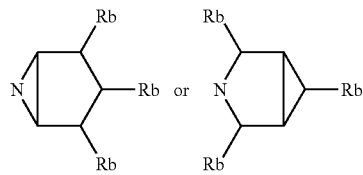

R is chosen from:
a pyridyl group, where the pyridyl may be in the form of N-Oxide ($N^+$—$O^-$),
or their pharmaceutically acceptable salts, or their optical isomers, racemates, diastereomers or enantiomers.
  12. A pharmaceutical composition comprising a compound of formula (I') with a pharmaceutically acceptable excipient or carrier, wherein said formula (I') is:

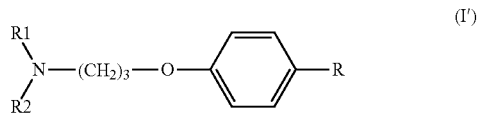

wherein R1 and R2 taken together with the nitrogen atom to which they are attached, form a mono or bicyclic saturated nitrogen-containing ring of formula:

with m=4 or 5, each Rb is independently identical or different, and Rb is a hydrogen or a $C_1$-$C_4$ alkyl, or 2 Rb form together a bond so as to form a bicyclic ring, chosen from:

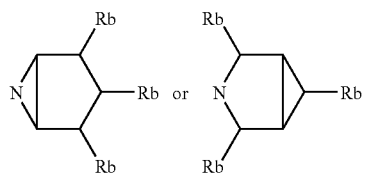

R is chosen from:
a) a pyridyl group, or a cycloalkyl, each optionally substituted with one or more of Halogen atom, C1-C4 alkyl, O—C1-C4 alkyl, OH or NR3R4 and where the N atom within the pyridyl ring may be in the form of N-Oxide ($N^+$—$O^-$), or
  bicyclic aryl substituted with one or more of Halogen atom, C1-C4 alkyl, O—C1-C4 alkyl, OH, NR3R4, —C2-C4, alkenyl or —C2-C4 alkynyl,
  where alkyl, alkenyl or alkynyl is optionally substituted with a heterocycle, or NR3R4;
  wherein R3, R4 are independently hydrogen, a straight or branched $C_1$-$C_4$ alkyl or an aryl group or taken together with the nitrogen atom to which they are attached form a saturated or partially unsaturated monocyclic or bicyclic heterocycle or heteroaryl optionally substituted with one or more of Halogen atom, C1-C4 alkyl, O—C1-C4 alkyl, or OH;
  or their pharmaceutically acceptable salts, or their optical isomers, racemates, diastereomers or enantiomers.

\* \* \* \* \*